(12) United States Patent
Peyman

(10) Patent No.: US 10,206,569 B1
(45) Date of Patent: *Feb. 19, 2019

(54) CORNEAL INTRAOCULAR PRESSURE SENSOR AND A SURGICAL METHOD USING THE SAME

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/653,053

(22) Filed: Jul. 18, 2017

Related U.S. Application Data

(63) Continuation-in-part of application No. 15/631,219, filed on Jun. 23, 2017, which is a continuation-in-part
(Continued)

(51) Int. Cl.
*A61B 3/16* (2006.01)
*A61F 9/008* (2006.01)
(Continued)

(52) U.S. Cl.
CPC ............. *A61B 3/16* (2013.01); *A61B 5/076* (2013.01); *A61F 2/142* (2013.01); *A61F 9/0081* (2013.01);
(Continued)

(58) Field of Classification Search
CPC .... A61F 9/007; A61F 9/0709; A61F 9/00736; A61F 9/00781; A61F 9/0079;
(Continued)

(56) References Cited

U.S. PATENT DOCUMENTS 3,760,807 A 9/1973 Neefe
4,563,779 A 1/1986 Kelman
(Continued)

FOREIGN PATENT DOCUMENTS

WO 89/04153 A1 5/1989
WO 92/16172 A1 10/1992
(Continued)

OTHER PUBLICATIONS

J. I. Barraquer, "Keratomileusis and Keratophakia for the Correction of Congenital Hypermetropia and Aphakia", Bulletins et Memories de la Societe Francaise D'Ophthalmologie, vol. 95, pp. 380-390 (1984).
(Continued)

*Primary Examiner* — Paul B Prebilic
(74) *Attorney, Agent, or Firm* — The Law Office of Patrick F. O'Reilly III, LLC

(57) ABSTRACT

A method of implanting a corneal intraocular pressure sensor in an eye of a patient is disclosed herein. The method includes forming a pocket in the cornea of the eye so as to gain access to tissue surrounding the pocket; applying a photosensitizer so that the photosensitizer permeates at least a portion of the tissue surrounding the pocket, the photosensitizer facilitating cross-linking of the tissue surrounding the pocket; irradiating the cornea so as to activate cross-linkers in the portion of the tissue surrounding the pocket, and thereby stiffen a wall of the pocket and kill cells in the portion of the tissue surrounding the pocket; and inserting an intracorneal implant comprising a pressure sensor into the pocket, the pressure sensor of the intracorneal implant configured to measure the intraocular pressure of the eye of the patient. A corneal intraocular pressure sensor is also disclosed herein.

22 Claims, 28 Drawing Sheets

Related U.S. Application Data of application No. 15/285,375, filed on Oct. 4, 2016, now Pat. No. 9,744,029, which is a continuation-in-part of application No. 15/230,445, filed on Aug. 7, 2016, now Pat. No. 9,937,033, which is a continuation-in-part of application No. 14/709,801, filed on May 12, 2015, now Pat. No. 9,427,355.

(60) Provisional application No. 62/363,382, filed on Jul. 18, 2016, provisional application No. 62/360,439, filed on Jul. 10, 2016, provisional application No. 62/360,281, filed on Jul. 8, 2016, provisional application No. 62/353,632, filed on Jun. 23, 2016, provisional application No. 62/065,714, filed on Oct. 19, 2014, provisional application No. 61/991,785, filed on May 12, 2014.

(51) Int. Cl.
| | | |
|---|---|---|
| *A61M 19/00* | (2006.01) | |
| *A61N 5/02* | (2006.01) | |
| *A61N 5/06* | (2006.01) | |
| *A61B 5/07* | (2006.01) | |
| *A61F 2/14* | (2006.01) | |

(52) U.S. Cl.
CPC ............ *A61M 19/00* (2013.01); *A61N 5/022* (2013.01); *A61N 5/062* (2013.01); *A61B 2560/063* (2013.01); *A61B 2562/0247* (2013.01); *A61N 2005/063* (2013.01); *A61N 2005/0661* (2013.01)

(58) Field of Classification Search
CPC .. A61F 9/008; A61F 9/00821–9/00834; A61F 2009/00872; A61F 2009/00885; A61F 2009/00891; A61F 2009/00893; A61F 2/142; A61F 2/145; A61F 2/1451; A61F 2/1453; A61F 2210/008; A61F 2210/0085; A61F 2240/00–2240/004; A61F 2250/0091; A61F 2250/0012
See application file for complete search history.

(56) References Cited

U.S. PATENT DOCUMENTS

| | | | |
|---|---|---|---|
| 4,665,913 A | 5/1987 | L'Esperance, Jr. | |
| 4,718,418 A | 1/1988 | L'Esperance, Jr. | |
| 4,793,344 A * | 12/1988 | Cumming | A61F 2/14 606/1 |
| 4,799,931 A | 1/1989 | Lindstrom | |
| 4,840,175 A | 6/1989 | Peyman | |
| 4,903,695 A | 2/1990 | Warner et al. | |
| 4,994,058 A | 2/1991 | Raven et al. | |
| 5,171,318 A | 12/1992 | Gibson et al. | |
| 5,336,261 A | 8/1994 | Barrett et al. | |
| 5,552,452 A | 9/1996 | Khadem | |
| 5,702,441 A | 12/1997 | Zhou | |
| 5,964,748 A | 10/1999 | Peyman | |
| 6,110,166 A | 8/2000 | Juhasz | |
| 6,180,687 B1 | 1/2001 | Hammer | |
| 6,197,019 B1 | 3/2001 | Peyman | |
| 6,537,545 B1 | 3/2003 | Karageozian et al. | |
| 6,551,307 B2 | 4/2003 | Peyman | |
| 7,001,374 B2 | 2/2006 | Peyman | |
| 7,004,902 B2 | 2/2006 | Luce | |
| 7,044,945 B2 | 5/2006 | Sand | |
| 9,301,925 B2 | 4/2016 | Xu et al. | |
| 9,370,446 B2 | 6/2016 | Peyman | |
| 9,814,567 B2 | 11/2017 | Peyman | |
| 2001/0027314 A1 | 10/2001 | Peyman | |
| 2002/0006394 A1 | 1/2002 | Redmond et al. | |
| 2002/0071856 A1 | 6/2002 | Dillingham | |
| 2003/0035843 A1 | 2/2003 | Livesey et al. | |
| 2004/0029855 A1 | 2/2004 | Klaveness et al. | |
| 2005/0246018 A1 | 11/2005 | Grubbs | |
| 2006/0135477 A1 | 6/2006 | Haitjema | |
| 2007/0135754 A1 | 6/2007 | Akiyama et al. | |
| 2007/0142908 A1 | 6/2007 | Xu | |
| 2007/0255404 A1 | 11/2007 | Pinchuk | |
| 2009/0171305 A1 | 7/2009 | El Hage | |
| 2009/0196903 A1 * | 8/2009 | Kliman | A61F 9/0017 424/423 |
| 2009/0208577 A1 | 8/2009 | Xu et al. | |
| 2010/0198348 A1 | 8/2010 | Hiles et al. | |
| 2010/0210996 A1 * | 8/2010 | Peyman | A61F 7/007 604/20 |
| 2010/0215717 A1 | 8/2010 | Soker et al. | |
| 2011/0034912 A1 * | 2/2011 | de Graff | A61B 1/05 606/21 |
| 2011/0076734 A1 | 3/2011 | Zhou et al. | |
| 2011/0152219 A1 | 6/2011 | Stagni et al. | |
| 2011/0166650 A1 | 7/2011 | Busin | |
| 2011/0208300 A1 | 8/2011 | de Juan, Jr. et al. | |
| 2011/0250688 A1 | 10/2011 | Hasan | |
| 2012/0035527 A1 * | 2/2012 | Tearney | A61L 27/3604 604/20 |
| 2012/0203161 A1 | 8/2012 | Herekar | |
| 2012/0226351 A1 | 9/2012 | Peyman | |
| 2016/0022495 A1 | 1/2016 | Feingold | |
| 2016/0331868 A1 | 11/2016 | Grubbs et al. | |
| 2017/0007395 A1 | 1/2017 | Peyman | |
| 2018/0177587 A1 * | 6/2018 | Anderson | A61F 9/013 |

FOREIGN PATENT DOCUMENTS

| | | |
|---|---|---|
| WO | 01/58495 A2 | 8/2001 |
| WO | 2008/055118 A2 | 5/2008 |

OTHER PUBLICATIONS

Wollensak et al., "Riboflavin/Ultraviolet-A—induced Collagen Crosslinking for the Treatment of Keratoconus", American Journal of Ophthalmology, vol. 135, pp. 620-627 (2003).

M. A. Bamashmus, M. F. Saleh, M. A. Awadalla, "Reasons for Not Performing Keratorefractive Surgery in Patients Seeking Refractive Surgery in a Hospital-Based Cohort in Yemen", Middle East Afr J Ophthalmol, Oct.-Dec. 2010; 17(4): pp. 349-353.

Goins et al., "Photodynamic biologic tissue glue to enhance corneal wound healing after radial keratotomy" (Nov. 1997), Journal of Cataract and Refractive Surgery, vol. 23, Issue 9, pp. 1331-1338. (Abstract only).

First office action on the merits (Non-Final Rejection) in U.S. Appl. No. 14/709,801, dated Jan. 11, 2016.

Second office action on the merits (Final Rejection) in U.S. Appl. No. 14/709,801, dated May 4, 2016.

Notice of Allowance in U.S. Appl. No. 14/709,801, dated Jul. 19, 2016.

First office action on the merits (Non-Final Rejection) in U.S. Appl. No. 15/230,445, dated Jul. 11, 2017.

Notice of Allowance in U.S. Appl. No. 15/230,445, dated Dec. 4, 2017.

* cited by examiner

FIG. 30
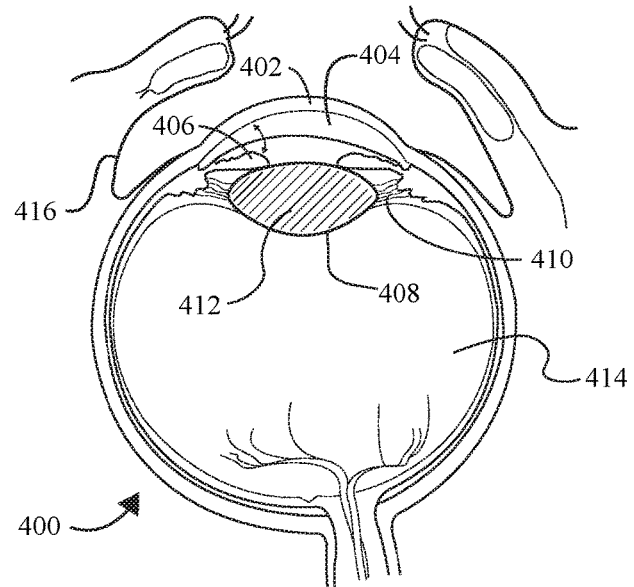
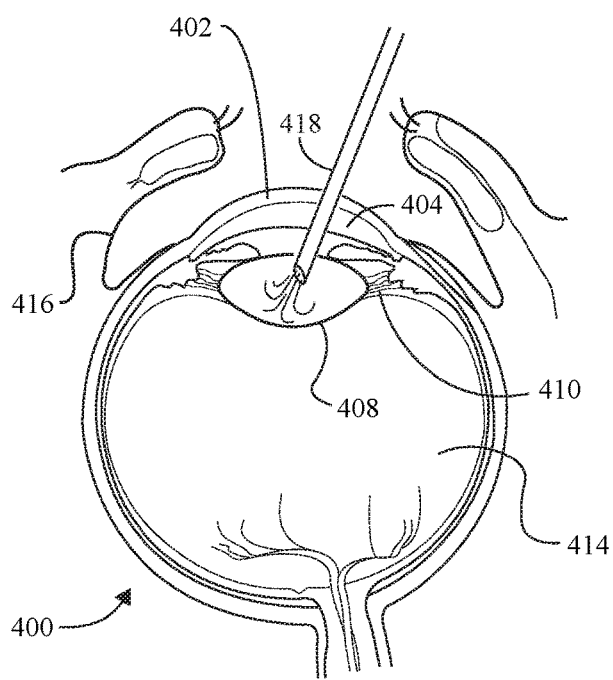
FIG. 31

Detail "A"

Detail "B"

Detail "C"

CORNEAL INTRAOCULAR PRESSURE SENSOR AND A SURGICAL METHOD USING THE SAME

CROSS-REFERENCE TO RELATED APPLICATIONS

This patent application claims priority to U.S. Provisional Patent Application No. 62/363,382, entitled "Corneal Intraocular Pressure Sensor And A Surgical Method Using The Same", filed on Jul. 18, 2016, and is a continuation-in-part of application Ser. No. 15/631,219, entitled "Method of Prevention of Capsular Opacification and Fibrosis After Cataract Extraction and/or Prevention of Fibrosis Around a Shunt or Stent After Glaucoma Surgery", filed Jun. 23, 2017, which claims priority to U.S. Provisional Patent Application No. 62/353,632, entitled "Method of Prevention of Capsular Opacification and Fibrosis After Cataract Extraction and/or Prevention of Fibrosis Around a Shunt or Stent After Glaucoma Surgery", filed on Jun. 23, 2016, and Ser. No. 15/631,219 is a continuation-in-part of application Ser. No. 15/285,375, entitled "Method of Preventing Capsular Opacification and Fibrosis Utilizing an Accommodative Intraocular Lens Implant", filed Oct. 4, 2016, now U.S. Pat. No. 9,744,029, which claims priority to U.S. Provisional Patent Application No. 62/360,439, entitled "Method of Preventing Capsular Opacification and Fibrosis with the Creation of an Accommodative Intraocular Lens", filed on Jul. 10, 2016, and Ser. No. 15/285,375 is a continuation-in-part of application Ser. No. 15/230,445, entitled "Corneal Lenslet Implantation With A Cross-Linked Cornea", filed Aug. 7, 2016, now U.S. Pat. No. 9,937,033, which claims priority to U.S. Provisional Patent Application No. 62/360,281, entitled "Method of Altering the Refractive Properties of an Eye", filed on Jul. 8, 2016, and Ser. No. 15/230,445 is a continuation-in-part of application Ser. No. 14/709,801, entitled "Corneal Transplantation With A Cross-Linked Cornea", filed May 12, 2015, now U.S. Pat. No. 9,427,355, which claims priority to U.S. Provisional Patent Application No. 61/991,785, entitled "Corneal Transplantation With A Cross-Linked Cornea", filed on May 12, 2014, and to U.S. Provisional Patent Application No. 62/065,714, entitled "Corneal Transplantation With A Cross-Linked Cornea", filed on Oct. 19, 2014, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to cataract and glaucoma surgical methods, and to sensors for measuring the intraocular pressure of an eye. More particularly, the invention relates to a corneal intraocular pressure sensor and a surgical method that utilizes the corneal intraocular pressure sensor.

2. Background

Corneal scarring is a major cause of blindness, especially in developing countries. There are various causes for corneal scarring, which include: bacterial infections, viral infections, fungal infections, parasitic infections, genetic corneal problems, Fuch's dystrophy, and other corneal dystrophies. A corneal transplant is often required if the corneal scarring is extensive, and cannot be corrected by other means. However, there can be major complications associated with a corneal transplant, such as corneal graft rejection wherein the transplanted cornea is rejected by the patient's immune system.

A normal emmetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emmetropic eye, or a cornea or lens having a refractive power stronger than that of the cornea and lens of an emmetropic eye. This stronger refractive power causes the far point to be projected in front of the retina.

Conversely, a hypermetropic or hyperopic eye has an axial length shorter than that of a normal emmetropic eye, or a lens or cornea having a refractive power less than that of a lens and cornea of an emmetropic eye. This lesser refractive power causes the far point to be focused behind the retina.

An eye suffering from astigmatism has a defect in the lens or shape of the cornea converting an image of the point of light to a line. Therefore, an astigmatic eye is incapable of sharply focusing images on the retina.

While laser surgical techniques, such as laser-assisted in situ keratomileusis (LASIK) and photorefractive keratectomy (PRK) are known for correcting refractive errors of the eye, these laser surgical techniques have complications, such as post-operative pain and dry eye. Also, these laser surgical techniques cannot be safely used on patients with corneas having certain biomechanical properties. For example, corneal ectasia may occur if these laser surgical techniques are applied to patients having thin corneas (e.g., corneas with thicknesses that are less than 500 microns).

Therefore, what is needed is a method for corneal transplantation that reduces the likelihood that the implanted cornea will be rejected by the patient. Moreover, a method is needed for corneal transplantation that is capable of preserving the clarity of the transplanted cornea. Furthermore, there is a need for a method of corneal transplantation that reduces the likelihood that the transplanted cornea will be invaded by migrating cells. Also, what is needed is a method for corneal lenslet implantation for modifying the cornea to better correct ametropic conditions. In addition, a method is needed for corneal lenslet implantation that prevents a lens implant from moving around inside the cornea once implanted so that the lens implant remains centered about the visual axis of the eye.

Moreover, many cataract patients experience complications following their cataract surgery. For example, opacification of the lens capsule affects about 80-90% of the eyes after cataract surgery because of proliferation of the remaining cells in the lens capsule. This post-surgery opacification requires a laser disruption of the posterior capsule for the patient to see.

Also, conventional monofocal intraocular lenses do not permit accommodation. As such, patients with monofocal intraocular lenses typically require reading glasses after cataract surgery.

Therefore, it is apparent that a need also exists for treatment of cell proliferation of the lens capsule after cataract extraction, and for an accommodative intraocular lens implant that enables the cataract patient to see both far and near objects without the need for supplemental lenses, such as reading glasses.

Furthermore, cataract patients who additionally have glaucoma pose difficult challenges for the treating ophthalmologist. When glaucoma is associated with a cataract in the same patient, the two surgeries must often be performed at the same time. However, unfortunately, both conditions can have their own complications. For example, as mentioned above, opacification of the lens capsule affects about 80-90% of the eyes after cataract surgery because of proliferation of the remaining cells in the lens capsule. This post-surgery opacification requires a laser disruption of the posterior capsule for the patient to see. Similarly, after glaucoma surgery, the connecting hole from the eye to the subconjunctival space may become plugged by fibrous proliferation occurring after surgery in an attempt to reject the shunt after the surgery or even a shunt in place, as a response of the surgical procedure creating a hole in the eye wall to drain the intraocular fluid.

Therefore, it is apparent that a need further exists for treatment of cell proliferation of the lens capsule after cataract extraction, and for treatment of fibrous cell proliferation after glaucoma surgery with or without a drainage tube.

Glaucoma is a disease that affects the eye and is considered one of the major causes of blindness in the world. There are many forms of glaucoma, having different pathogenesis. Among these are open angle glaucoma (OAG) where the anterior chamber located between the cornea and the iris is open, closed angle glaucoma where the anterior chamber angle is closed, and secondary glaucoma caused by different etiologies, but often an inflammatory process proceeds its occurrence. The glaucoma can be congenital or acquired, and some have genetic predisposition. Regardless of its pathogenesis, the hallmark of the disease is mostly an increased intraocular pressure (IOP), except for in the low tension glaucoma where the IOP appears to be normal, but the patient has the other symptoms of glaucoma. The other characteristic findings in glaucoma eyes are the cupping of the optic nerve head, and the loss of the nerve fiber layer of the retina and ganglion cells of the retina. These can lead to, or can also be considered a consequence of a degenerative process affecting potentially the retinal ganglion cells and an imbalance of the IOP and intracranial pressure leading to gradual loss of the visual field that can be constricted with time or completely lost resulting in blindness.

There are many treatment modalities in managing the disease processes. Since the IOP is, in most cases, elevated beyond a normal level of 10-20 mmHg, routine checking of the IOP including potentially a 24-hour or more measuring of these values during the day and night is needed to find out if there are any pressure variations during the course of the day, especially during sleep where the IOP generally is raised. These pressure variations can obviously compromise the retinal nerves and circulation, even if the pressure is within a normal range of 10-20 mmHg, such as in patients with low tension glaucoma. Thus far, the measurement of the IOP has been sporadic because it is limited by a patient's visit to the doctor's office.

The treatment for glaucoma has been mostly medicinal, that is by applying antiglaucoma medication(s) as eye drops to reduce the intraocular pressure. If the IOP cannot be controlled, either by laser surgery of the angle or ciliary body processes where the fluid is produced, then alternatively, one tries to drain the intraocular fluid to outside of the eye through a stent or shunt opening with one end in the anterior chamber and the other end located in the subconjunctival space or connecting the intraocular fluid via a shunt tube from the inside the eye to the choroidal space. In some situations, the surgeon makes a small hole in the eye wall connecting the anterior chamber fluid or aqueous directly to the subconjunctival space. There are a number of variations of this surgery having the same goal of reducing the IOP to a normal level. The glaucoma can also be associated with a cataract and not seldom requires doing the two surgeries at the same time. However, unfortunately both conditions can have their own complications (e.g., opacification of the lens capsule after cataract surgery affecting about 80-90% percent of the eyes because of proliferation of the remaining cells in the lens capsule, and requiring a laser disruption of the posterior capsule for the patient to see). Similarly, after glaucoma surgery, the connecting hole from the eye to the subconjunctival space can become plugged by fibrous proliferation occurring after surgery with or without a shunt tubing.

Recently, efforts have been made experimentally to measure the intraocular pressure via a contact lens positioned on the surface of the cornea for a duration of 24 hours with a pressure sensor and transmit the information wirelessly to a receiver mounted on an eye glass frame. The disadvantage of this contact lens system is that the system provides the measurement of the IOP indirectly from the eye cavity and depends on how the corneal curvature is deformed in response to the IOP. Also, the contact lens can be worn only for a short time because, otherwise it can interfere with the corneal oxygenation that happens mostly from the outside air and nutrition of the cornea that is, in part, supplied by the tear film that is compromised by placement of a static contact lens on the cornea. The chances of a corneal abrasion is increased by the described shortcomings, and for the patient, the placement and removal of the contact lens is particularly difficult in elderly patients.

Another recent effort has implanted such a system inside the lens capsule of the eye, by removing the natural crystalline lens, but leaving the lens capsule intact so that the device can be positioned inside the lens capsule and measure the IOP, and then transmit it outside the eye to a receiver. Because the system disposed in the lens capsule requires a battery to operate, the eventual need to replace the battery necessitates another surgical procedure to be performed later. Also, the initial surgical procedure has its own serious complications, and often is not justified when one is dealing with young patients or children. In addition, this process creates capsular opacification, it deprives the patient from the use of his or her natural lens, and can have the lifelong potential complication of inflammation that aggravates the existing glaucoma itself.

Therefore, it is apparent that a need further exists for an intraocular pressure measurement device and a method using the same that eliminates the shortcomings of the aforedescribed procedures.

BRIEF SUMMARY OF EMBODIMENTS OF THE INVENTION

Accordingly, the present invention is directed to a corneal intraocular pressure sensor and a surgical method using the same that substantially obviates one or more problems resulting from the limitations and deficiencies of the related art.

In accordance with one or more embodiments of the present invention, there is provided a method of implanting a corneal intraocular pressure sensor in an eye of a patient. The method includes the steps of: (i) forming a pocket in the cornea of the eye so as to gain access to tissue surrounding the pocket; (ii) after the pocket in the cornea has been formed, applying a photosensitizer so that the photosensitizer permeates at least a portion of the tissue surrounding the pocket, the photosensitizer facilitating cross-linking of the tissue surrounding the pocket; (iii) irradiating the cornea so as to activate cross-linkers in the portion of the tissue surrounding the pocket, and thereby stiffen a wall of the pocket and kill cells in the portion of the tissue surrounding the pocket; and (iv) before or after the portion of the tissue surrounding the pocket has been stiffened and is devoid of cellular elements by the activation of the cross-linkers, inserting an intracorneal implant comprising a pressure sensor into the pocket, the pressure sensor of the intracorneal implant configured to measure the intraocular pressure of the eye of the patient.

In a further embodiment of the present invention, the step of forming a pocket in the cornea of the eye further comprises cutting out a three-dimensional portion of stromal tissue from the cornea of the eye using a femtosecond laser; and removing the three-dimensional cut portion of the cornea using forceps so as to create a three-dimensional pocket for receiving the intracorneal implant so that the intracorneal implant does not exert any pressure on the stromal tissue of the cornea, the three-dimensional pocket being formed in a peripheral portion of the cornea between the cornea and the anterior sclera of the eye In yet a further embodiment, the method further comprises the step of, prior to forming the pocket in the cornea of the eye, bleaching out any peripheral conjunctival capillaries that are present with a low dose of a vasoconstrictive medication and/or a low dose of hyaluronic acid in a fluid in order to make the corneal limbus area transparent prior to applying the femtosecond laser.

In still a further embodiment, the three-dimensional pocket formed in the peripheral portion of the cornea extends between 1 degree and 360 degrees around the corneal periphery, and the three-dimensional pocket is located at predetermined distance from the Bowman's membrane of the cornea of the eye, and the three-dimensional pocket has a width between approximately 1 millimeters and approximately 4 millimeters, inclusive.

In yet a further embodiment, the step of forming a pocket in the cornea of the eye further comprises forming one or two incisions in the stromal tissue of the cornea of the eye using a femtosecond laser; and using a curved probe to separate a remaining corneal adhesion between walls of the incisions so as to create a three-dimensional pocket for the application of the photosensitizer.

In still a further embodiment, the step of applying the photosensitizer comprises injecting the photosensitizer inside the three-dimensional pocket using a needle such that the photosensitizer penetrates at least 20 microns beyond a wall of the three-dimensional pocket in the stromal tissue of the cornea, the photosensitizer comprising riboflavin.

In yet a further embodiment, the method further comprises the step of injecting 0.01 milliliters to 0.1 milliliters of a 0.02 to 2% concentration lidocaine or bupivacaine solution alone or together with the photosensitizer so as to anesthetize the cornea for between 10 to 15 hours, thereby eliminating a pain sensation or discomfort during the surgical procedure.

In still a further embodiment, the step of applying the photosensitizer comprises applying the photosensitizer in drop form to the epithelium or denuded epithelium of the cornea, the photosensitizer comprising riboflavin at a concentration of 1-2% in a physiological solution that additionally includes dextran, hyaluronic acid, or chondroitin sulfate; the step of irradiating the cornea so as to activate cross-linkers in the portion of the tissue surrounding the pocket comprises irradiating the cornea with ultraviolet light from outside the cornea; and the method further comprises the step of waiting for a period of 3 to 4 weeks after cross-linking prior to inserting the intracorneal implant comprising the pressure sensor into the pocket.

In yet a further embodiment, the step of creating a pocket in the cornea of the eye further comprises forming a circular-shaped pocket, a semi-circular-shaped pocket, a C-shaped pocket, a doughnut-shaped pocket, or a rectangular-shaped pocket in the cornea of the eye, and removing the tissue inside the circular-shaped pocket, the semi-circular-shaped pocket, the C-shaped pocket, the doughnut-shaped pocket, or the rectangular-shaped pocket.

In still a further embodiment, the step of irradiating the cornea so as to activate cross-linkers in the portion of the tissue surrounding the pocket comprises irradiating the cornea with ultraviolet light, another wavelength of light, microwaves, or combinations thereof.

In yet a further embodiment, the step of irradiating the cornea so as to activate cross-linkers in the portion of the tissue surrounding the pocket comprises inserting a fiber optic into the pocket and irradiating the cornea with light emitted from the fiber optic so as to activate the cross-linkers in the portion of the tissue surrounding the pocket.

In still a further embodiment, the step of irradiating the cornea so as to activate cross-linkers in the portion of the tissue surrounding the pocket comprises irradiating the cornea from outside the eye.

In yet a further embodiment, the method further comprises the step of, prior to the insertion of the intracorneal implant into the pocket, injecting a predetermined amount of hyaluronic acid or a viscous biocompatible material into the pocket so as to simplify the insertion of the intracorneal implant in the pocket.

In still a further embodiment, the intracorneal implant further comprises a needle and the pressure sensor of the intracorneal implant comprises a capacitor; and the method further comprises the step of penetrating a posterior portion of the cornea using the needle, an open end of the needle opening into the anterior chamber of the eye so as to measure the intraocular pressure of the eye without obstructing vision through the central cornea of the eye.

In yet a further embodiment, the needle of the intracorneal implant is a 23-34 gauge needle with the pressure sensor disposed inside the needle; and wherein the needle is disposed generally perpendicularly with respect to a body portion of the intracorneal implant and the needle has a length that is less than 500 microns and a diameter that is less than 200 microns.

In still a further embodiment, the intracorneal implant further comprises an antenna; and the method further comprises the step of transmitting intraocular pressure data acquired by the pressure sensor wirelessly to a remote receiver located outside of the eye.

In yet a further embodiment, the remote receiver is located on an eyeglass frame of the patient; and the method further comprises the step of continuously receiving the intraocular pressure data transmitted by the antenna of the intracorneal implant at the remote receiver during a period of time selected from the group consisting of weeks, months, and years.

In still a further embodiment, the method further comprises the step of, after receiving the intraocular pressure data at the remote receiver, further transmitting the intraocular pressure data to a remote computing device for processing and analyzing the intraocular pressure data.

In yet a further embodiment, the method further comprises, prior to inserting the intracorneal implant with the pressure sensor into the pocket, the steps of coating an outer surface of the intracorneal implant with an organic polymer configured to absorb the photosensitizer; immersing the intracorneal implant in a biocompatible solution comprising the photosensitizer so that the photosensitizer is able to diffuse out of the organic polymer coating of the intracorneal implant after the intracorneal implant is inserted into the pocket; and after the intracorneal implant is inserted into the pocket, irradiating the cornea so as to activate cross-linkers in the portion of the tissue surrounding the pocket, and thereby stiffen a wall of the pocket and kill cells in the portion of the tissue surrounding the pocket.

In still a further embodiment, the method further comprises the step of, after the implantation of the intracorneal implant, applying the photosensitizer one or more additional times inside the space between the intracorneal implant and the surrounding corneal tissue by injecting the photosensitizer inside the space between the intracorneal implant and the surrounding corneal tissue using a 33 gauge needle, and irradiating the cornea one or more additional times with ultraviolet radiation to cross-link the tissue surrounding the intracorneal implant so as to prevent encapsulation of the intracorneal implant and cellular migration towards the intracorneal implant.

In yet a further embodiment, the intracorneal implant further comprises an antenna, a radio frequency generator, and a needle containing the pressure sensor; and the step of inserting the intracorneal implant into the pocket further comprises placing the antenna of the intracorneal implant into the cross-linked pocket; placing the radio frequency generator and the pressure sensor into the cross-linked pocket; connecting the radio frequency generator and the pressure sensor to the antenna; and pushing the needle with the pressure sensor into the anterior chamber of the eye so that the pressure sensor is capable of measuring the intraocular pressure directly in a continuous manner.

In still a further embodiment, the method further comprises the steps of taking a first measurement of the intraocular pressure of the eye of the patient using the pressure sensor of the intracorneal implant disposed in the cross-linked pocket at a periphery of the cornea; taking a second measurement of the intraocular pressure of the eye using a Goldmann applanation tonometer placed on a central portion of the outer cornea surface; and comparing the first measurement of the intraocular pressure determined using the pressure sensor of the intracorneal implant to the second measurement of the intraocular pressure determined using the Goldmann applanation tonometer in order to validate the accuracy of the pressure sensor of the intracorneal implant.

In accordance with one or more other embodiments of the present invention, there is provided a corneal intraocular pressure sensor that includes a pressure sensor configured to measure an intraocular pressure of an eye and to output a signal based on the measured intraocular pressure of the eye, the pressure sensor configured to be implanted in a cornea of the eye, and the pressure sensor comprising a capacitor; a needle configured to penetrate a posterior portion of the cornea of the eye, the needle configured to open into the anterior chamber of the eye so as to measure the intraocular pressure of the eye without obstructing vision through the central cornea; a processor operatively coupled to the pressure sensor, the processor configured to generate intraocular pressure data based upon the signal outputted by the pressure sensor; and a transmitter device operatively coupled to the processor, the transmitter device configured to transmit the intraocular pressure data generated by the processor to a remote receiver located outside of the eye, the transmitter device configured to be implanted in the cornea of the eye, the transmitter device further comprising a radio frequency generator and an antenna operatively coupled to the radio frequency generator, the antenna configured to wirelessly transmit the intraocular pressure data acquired by the pressure sensor to the remote receiver located outside of the eye.

In a further embodiment of the present invention, the remote receiver is located on an eyeglass frame of the patient, and wherein the remote receiver is configured to continuously receive the intraocular pressure data transmitted by the antenna of the corneal intraocular pressure sensor during a period of time selected from the group consisting of weeks, months, and years.

In yet a further embodiment, the pressure sensor, processor, and transmitter device are provided with a coating on outer surfaces thereof, the coating comprising an organic polymer configured to absorb a photosensitizer.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 30 is a side cross-sectional view illustrating an eye with a cataract, according to yet another embodiment of the invention;

FIG. 31 is another side cross-sectional view of the eye of FIG. 30, which illustrates the application of a photosensitizer to a posterior portion of the capsular bag of the eye after the cataract has been removed;

Throughout the figures, the same elements are always denoted using the same reference characters so that, as a general rule, they will only be described once.

DETAILED DESCRIPTION OF EMBODIMENTS OF THE INVENTION

A first illustrative embodiment of a corneal transplant procedure with a cross-linked cornea is shown in FIGS. 1A-1D. The corneal transplant procedure illustrated in FIGS. 1A-1D involves full corneal replacement of the scarred or diseased cornea by the donor cornea. In other words, FIGS. 1A-1D illustrate a penetrating keratoplasty procedure wherein the full thickness of the scarred or diseased cornea is replaced with a cross-linked donor cornea (i.e., a full-thickness corneal transplant).

Figure 1A:
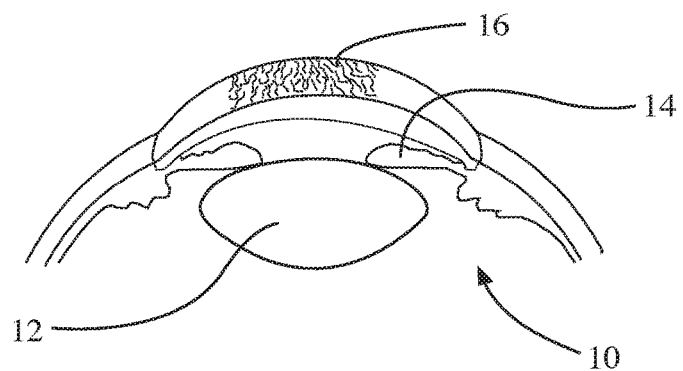
FIG. 1A is a partial side cross-sectional view of an eye having a scarred cornea, wherein substantially the entire thickness of the cornea is scarred.

Referring initially to FIG. 1A, it can be seen that substantially the entire thickness of the cornea 16 of the eye 10 is scarred and/or diseased (i.e., scarred, diseased, or scarred and diseased). FIG. 1A also illustrates the lens 12 and iris 14 of the eye 10, which are located posteriorly of the cornea 16. In this embodiment, it is necessary to replace substantially the entire thickness of the cornea 16 with a donor cornea.

Figure 1B:
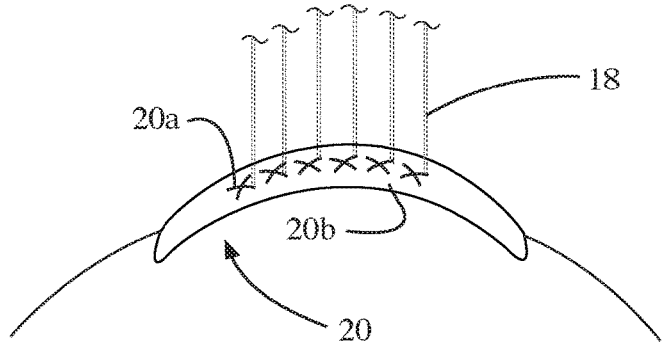
FIG. 1B is a partial side cross-sectional view of a donor cornea undergoing cross-linking.

In FIG. 1B, the cross-linking 18 of the clear donor cornea 20 is diagrammatically illustrated. As depicted in FIG. 1B, only the front portion 20a of the donor cornea 20 is cross-linked. That is, the cross-linking does not extend all the way to the rear portion 20b of the donor cornea 20. It is to be understood that the cross-linking 18 of the donor cornea 20 may also be done after implanting the donor cornea into the eye of the patient, rather than before implantation as shown in the illustrative example of FIGS. 1A-1D. Also, it is to be understood that all or just a part of the donor cornea 20 may be cross-linked.

In the illustrative embodiments described herein (i.e., as depicted in FIGS. 1A-1D, 2A-2C, and 3A-3C), the cross-linking of the clear donor cornea may comprise the steps of: (i) applying a photosensitizer to the donor cornea, the photosensitizer facilitating cross-linking of the donor cornea; and (ii) irradiating the donor cornea with ultraviolet light so as to activate cross-linkers in the donor cornea and thereby strengthen the donor cornea. The photosensitizer may comprise riboflavin or a solution comprising a liquid suspension having nanoparticles of riboflavin. The cross-linker may have between about 0.1% Riboflavin to about 100% Riboflavin or any other suitable range or specific percentage therein. The ultraviolet radiation or rays used to irradiate the donor cornea may be between about 370 nanometers and about 380 nanometers (or between 370 nanometers and 380 nanometers). The radiation is preferably about 3 mW or more as needed and emanates from a laser source at about a 3 cm distance from the donor cornea for about 30 minutes or less. The time of the exposure can vary depending on the light intensity, focus, and the concentration of riboflavin. However, the ultraviolet radiation can be applied at any suitable distance, time or wavelength. Preferably, cross-linking the donor cornea does not significantly change the refractive power of the donor cornea; however, if desired, cross-linking can change the refractive power of the donor cornea to any suitable degree.

In addition to Riboflavin, other suitable cross linking agents are low carbon carbohydrates, such as pentose sugar (e.g., ribose) or hexose sugar (e.g., glucose), or complex carbohydrates. Other crosslinking agents may include Transaminidases, transglutaminases or a naturally-derived cross-linker named malic acid derivative (MAD) concentrations higher than 30 mM, commercially available cross-linkers such as 1-ethyl-3-(3('-dimethylaminopropyl) carbodiimide (EDC), or ethyl-3(3-dimethylamino) propyl carbodiimide (EDC), etc. The cross-linking may also be done postoperatively by the application of other crosslinking agents, such as Triglycidylamine (TGA) synthesized via reacting epichlorhydrin and a carbodiimide, or the oxidized glycogen hexoses. The ribose, glucose and similar agents may penetrate the cornea easily using drops, gel, or the slow release mechanisms, nanoparticle, microspares, liposome sets. In addition, the crosslinkers may be delivered with Mucoadhesives.

In one or more embodiments, all or part of the donor cornea is cross-linked. Also, in one or more embodiments, a very high concentration of Riboflavin may be used because the in vitro cross-linking process may be stopped whenever needed prior to the transplantation of the donor cornea in the host eye. In addition, the power of the ultraviolet (UV) laser may also be increased so as to cross-link the tissue of the donor cornea faster. The use of a high concentration of Riboflavin, and the increasing of the ultraviolet (UV) laser power, are not possible during an in vivo cross-linking procedure because the aim of such an in vivo procedure is to protect the cells of the host cornea. Also, the in vivo process cannot be controlled as efficiently as in the vitro crosslinking of the corneal transplant.

In one or more embodiments, the donor cornea may be extracted from a human cadaver, or the cornea may be reconstructed as known in tissue engineering in vitro and three-dimensionally (3D) printed. Cross-linking of a culture-grown cornea eliminates the cellular structure inside the cornea. If needed again, the healthy corneal endothelium of the patient may be grown in vitro for these tissues by placing them on the concave surface of the cornea and encouraging their growth under laboratory control conditions prior to the transplantation.

In the embodiments where the donor cornea is tissue culture grown, the cornea may be formed from mesenchymal fibroblast stem cells, embryonic stem cells, or cells derived from epithelial stem cells extracted from the same patient, or a mixture of these cells. Using known tissue culture techniques, the cells may produce a transparent corneal stroma. This culture-grown corneal stroma will not have a corneal epithelium or a corneal endothelium. Thus, it eliminates the complexity of developing a full thickness cornea in the tissue culture. This stromal transplant may be used as a lamellar or partial thickness replacement of the existing host cornea. This transplant may also be used to augment or add to the thickness of the host cornea. This transparent corneal stroma may be transplanted either prior to, or after being cross-linked using various cross-linking methods.

In one or more embodiments, the cross-linked donor cornea may be sized and precisely cut with a femtosecond laser to the desired shape and curvature to replace the removed host cornea so that the refractive errors of the recipient are also automatically corrected with the cross-linked cornea.

Figure 1C:
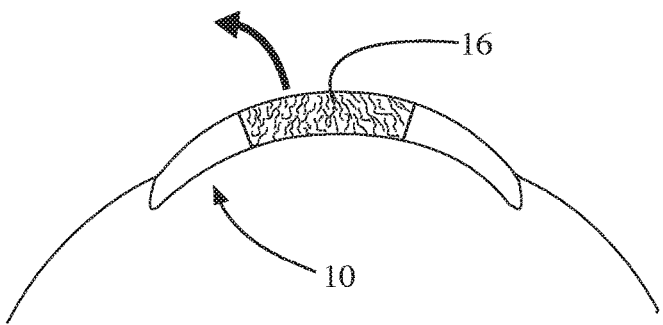
FIG. 1C is a partial side cross-sectional view of the eye of FIG. 1A, wherein the scarred cornea is shown being removed.

Now, referring to FIG. 1C, it can be seen that the scarred and/or diseased cornea 16 is shown being removed from the eye 10. The scarred and/or diseased cornea 16 may be removed from the eye 10 by using various suitable means, such as mechanical means or cutting using a laser. When mechanical means are used to remove the scarred and/or diseased cornea 16 from the eye 10, the scarred and/or diseased cornea 16 may initially be cut away or dissected from the remainder of the eye 10 using a sharp mechanical instrument (e.g., a surgical micro-knife, a needle, a sharp spatula, a pair of micro-scissors), and then subsequently removed or extracted with a pair of micro-forceps. When laser cutting is used to remove the scarred and/or diseased cornea 16 from the eye 10, the scarred and/or diseased cornea 16 may be cut away using a suitable laser, such as a femtosecond laser. Also, in some embodiments, the mechanical means for cutting and extraction (e.g., the surgical micro-knife and/or pair of micro-scissors) may be used in combination with the laser means (e.g., the femtosecond laser).

In one or more embodiments, the donor cornea may be shaped and cut with the femtosecond laser prior to the cross-linking thereof so as to replace part or all of the recipient cornea which is cut with the femtosecond laser. In these one or more embodiments, the entire donor and host cornea together may be cross-linked with Riboflavin and UV radiation. These procedures may also be performed on a culture-grown transplant cornea.

Figure 1D:
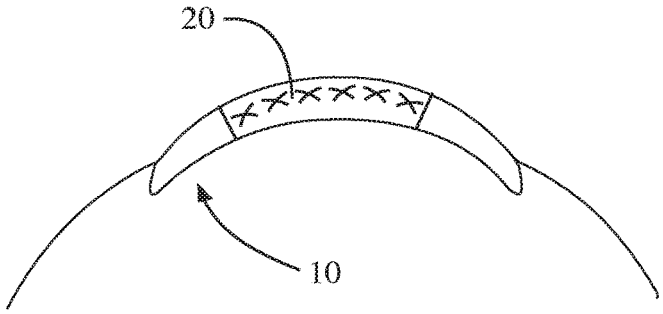
FIG. 1D is a partial side cross-sectional view of the eye of FIG. 1A, wherein the cross-linked donor cornea is shown being implanted in the location previously occupied by the scarred cornea.

Then, as shown in FIG. 1D, after the scarred and/or diseased cornea 16 has been removed from the eye 10, the cross-linked donor cornea 20 is implanted into the eye 10 of the patient in the location previously occupied by the scarred and/or diseased cornea 16. After implantation of the cross-linked donor cornea 20, sutures or a suitable adhesive may be utilized to secure the cross-linked donor cornea 20 in place on the eye 10. When sutures are used for holding the donor cornea 20 in place, the sutures may comprise nylon sutures, steel sutures, or another suitable type of non-absorbable suture. When the cornea 16 is subsequently ablated after the implantation of the donor cornea, as will be described hereinafter, additional sutures may be required after ablation.

In one or more embodiments, a biodegradable adhesive is used in a corneal transplantation procedure with the cross-linked donor cornea 20 described above, or with a non-cross-linked corneal transplant. In these one or more embodiments, the biodegradable adhesive obviates the need for a suture in the corneal transplant procedure. Sutures generally distort the surface of the cornea and can produce an optically unacceptable corneal surface. Also, the use of the biodegradable adhesive obviates the need for glues requiring exothermic energy. Glues that use an exothermic effect, such as Fibronectin, need thermal energy to activate their adhesive properties. This thermal energy, such as that delivered by a high-powered laser, produces sufficient heat to coagulate the Fibronectin and the tissue that it contacts. Any thermal effect on the cornea produces: (i) corneal opacity, (ii) tissue contraction, and (iii) distortion of the optical surface of the cornea. The tissue adhesion created by these glues, including Fibronectin or fibrinogen, is flimsy and cannot withstand the intraocular pressure of the eye.

In fact, sutures are superior to these types of adhesives because the wound becomes immediately strong with sutures, thereby supporting the normal intraocular pressure of between 18 and 35 mmHg. In contrast to the use of a suture in which distortion that is caused by suture placement can be managed by cutting and removing the suture, the distortion caused by the coagulated corneal tissue cannot be corrected.

Other glues, such as cyanoacrylate, become immediately solid after coming into contact with the tissue or water. These glues produce a rock-hard polymer, the shape of which cannot be controlled after administration. Also, the surface of the polymer created by these glues is not smooth. Thus, the eyelid will rub on this uneven surface, and the uneven surface scratches the undersurface of the eyelid when the eyelid moves over it. In addition, the cyanoacrylate is not biodegradable or biocompatible. As such, it causes an inflammatory response if applied to the tissue, thereby causing undesirable cell migration and vascularization of the cornea.

Thus, by using a biocompatible and absorbable acrylate or other biodegradable glues that do not need exothermic energy for the process of adhesion (i.e., like fibronectin or fibrinogen), one is able to maintain the integrity of the smooth corneal surface. In one or more embodiments, the biocompatible and biodegradable adhesive may be painted only at the edges of the transplant prior to placing it in the host or diseased cornea. In these embodiments, the biocompatible and biodegradable adhesive only comes into contact with the host tissue at the desired predetermined surface to create a strong adhesion. The adhesion may last a few hours to several months depending on the composition of the molecule chosen and the concentration of the active component.

Other suitable biodegradable adhesives or glues that may be used in conjunction with the transplant include combinations of gallic acid, gallic tannic acid, Chitosan, gelatin, polyphenyl compound, Tannic Acid (N-isopropylacrylamide (PNIPAM), and/or Poly(N-vinylpyrrolidone) with polyethylene glycol (PEG). That is, polyethylene glycol (PEG) may be mixed with any one or plurality of gallic acid, gallic tannic acid, Chitosan, gelatin, polyphenyl compound, Tannic Acid (N-isopropylacrylamide (PNIPAM), and Poly(N-vinylpyrrolidone), so as to form a molecular glue. These adhesives are suitable for the use on the cornea because they create a tight wound that prevents leakage from the corneal wound and maintain the normal intraocular pressure shortly after their application and also do not distort the wound by causing traction on the tissue.

In addition, other suitable biodegradable adhesives or glues, which may need an external source of energy, that are able to be used in conjunction with the transplant include combinations of riboflavin, lactoflavin, gallic acid, gallic tannic acid, Chitosan, gelatin, polyphenyl compound, Tannic Acid (N-isopropylacrylamide (PNIPAM), dopamine, and/or Poly(N-vinylpyrrolidone) with polyethylene glycol (PEG). That is, polyethylene glycol (PEG) may be mixed with any one or plurality of riboflavin, lactoflavin, tannic acid, dopamine, gallic tannic acid, Chitosan, gelatin, polyphenyl compound, Tannic Acid (N-isopropylacrylamide (PNIPAM), and Poly(N-vinylpyrrolidone), so as to form a molecular glue. These adhesives are also suitable for the use on the cornea because they create a tight wound that prevents leakage from the corneal wound and maintain the normal intraocular pressure shortly after their application and also do not distort the wound by causing traction on the tissue.

In one or more embodiments, the donor cornea may be temporarily sutured to the host cornea by only a few single sutures to the host cornea. Then, the sutures may be removed immediately after donor cornea is fixed to the host cornea with a suitable adhesive.

Figure 2A:
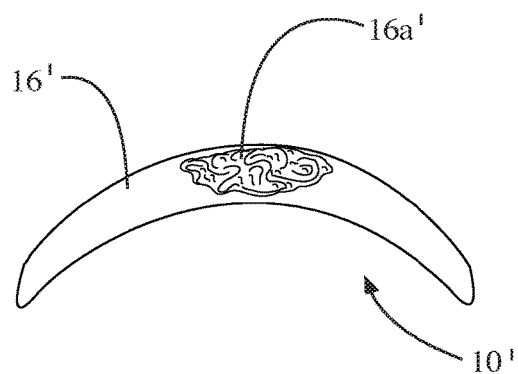
FIG. 2A is a partial side cross-sectional view of an eye having internal corneal scar tissue.
Figure 2B:
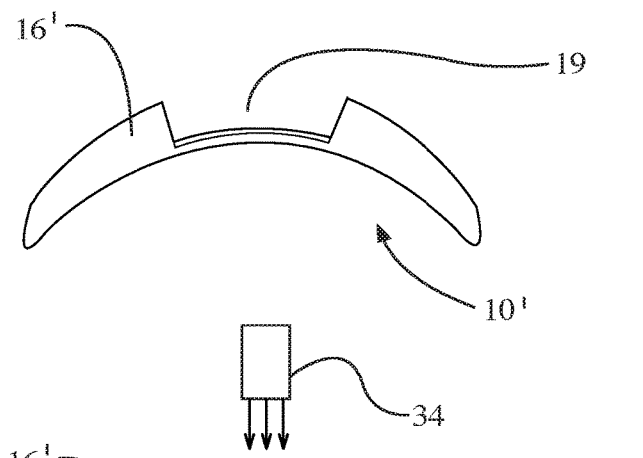
FIG. 2B is a partial side cross-sectional view of the eye of FIG. 2A, wherein the scarred corneal tissue has been externally removed from the eye.
Figure 2C:
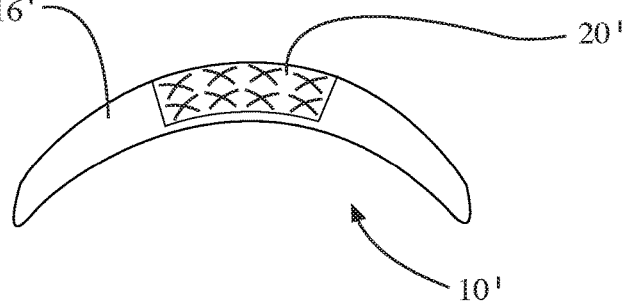
FIG. 2C is a partial side cross-sectional view of the eye of FIG. 2A, wherein a cross-linked donor cornea is shown being implanted in the location previously occupied by the scarred corneal tissue.

A second illustrative embodiment of a corneal transplant procedure with a cross-linked cornea is shown in FIGS. 2A-2C. Unlike the first embodiment described above, the corneal transplant procedure illustrated in FIGS. 2A-2C does not involve full corneal replacement of the scarred or diseased cornea by the donor cornea. Rather, FIGS. 2A-2C illustrate a lamellar keratoplasty procedure wherein only a portion of the cornea 16' of the eye 10' contains scarred and/or diseased tissue (i.e., a full-thickness corneal section is not removed). In the procedure of FIGS. 2A-2C, an internal scarred and/or diseased portion 16a' of the cornea 16' is externally removed from the eye 10' of a patient.

Referring initially to FIG. 2A, it can be seen that only an internal portion 16a' of the cornea 16' is scarred and/or diseased. As such, in this embodiment, it is not necessary to replace the entire thickness of the cornea 16 with a donor cornea as was described above in conjunction with FIGS. 1A-1D, but rather just a portion of the cornea 16'.

Next, referring to FIG. 2B, it can be seen that the scarred and/or diseased portion 16a' has been externally removed from the cornea 16' of the eye 10' such that the cornea 16' comprises a cavity 19 disposed therein for receiving the donor cornea. Because an external approach was utilized for removing the scarred and/or diseased portion 16a' of the cornea 16', the cavity 19 comprises a notch-like void in the outside or anterior surface of the cornea 16'. As described above for the first embodiment, the scarred and/or diseased corneal portion 16a' may be removed from the remainder of the cornea 16' using various suitable means, such as mechanical means or the laser cutting means (e.g., femtosecond laser) described above.

Finally, as shown in FIG. 2C, after the scarred and/or diseased portion 16a' has been removed from the remainder of the cornea 16' of the eye 10', the cross-linked donor cornea or cross-linked donor corneal portion 20' is implanted into the eye 10' of the patient in the location previously occupied by the scarred and/or diseased corneal portion 16a'. As described above, after implantation of the cross-linked donor corneal portion 20' into the eye 10', sutures or a suitable adhesive (e.g., the biocompatible and biodegradable adhesive described above) may be utilized to secure the cross-linked donor corneal portion 20' in place on the host cornea of the eye 10'.

After the cross-linked donor corneal portion 20' is implanted into the eye 10' of the patient, a portion of the cornea 16' may be ablated so as to change the refractive properties of the eye (e.g., to give the patient perfect or near perfect refraction). The ablation of the portion of the cornea 16' may be performed using a suitable laser 34, such as an excimer laser. The ablation by the laser causes the ablated tissue to essentially evaporate into the air. Also, the ablation of the portion of the cornea 16' may be done intrastromally, as with LASIK (laser-assisted in situ keratomileusis), or on the surface of the cornea, as with PRK (photorefractive keratectomy). The ablation may be performed a predetermined time period after the corneal transplantation so as to enable the wound healing process of the recipient's cornea to be completed. It is to be understood that the ablation, which follows the corneal transplantation, may be performed in conjunction with any of the embodiments described herein.

It is also to be understood that, in some alternative embodiments, the ablation may be performed prior to the transplantation of the donor cornea, rather than after the transplantation of the donor cornea. For example, in one or more alternative embodiments, a lenticle may be precisely cut in the tissue of a culture-grown stroma of a donor cornea by using a femtosecond laser so that when implanted into the host cornea, it corrects the residual host eye's refractive error.

Figure 3A:
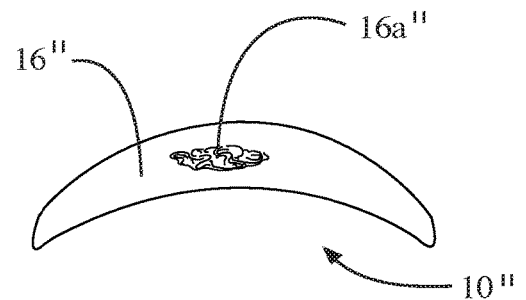
FIG. 3A is a partial side cross-sectional view of an eye having internal corneal scar tissue.
Figure 3B:
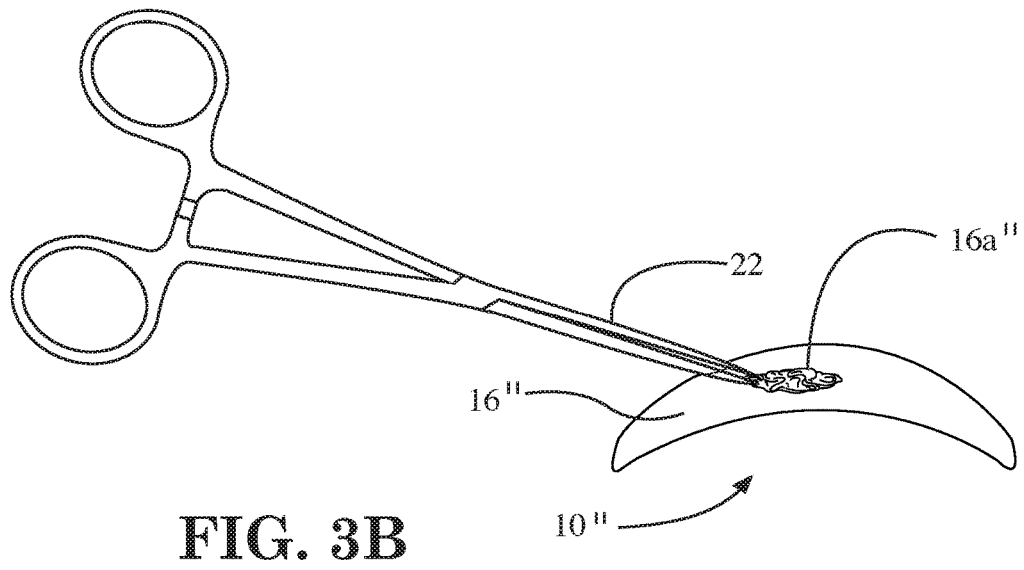
FIG. 3B is a partial side cross-sectional view of the eye of FIG. 3A, wherein the scarred corneal tissue is shown being internally removed from the eye.
Figure 3C:
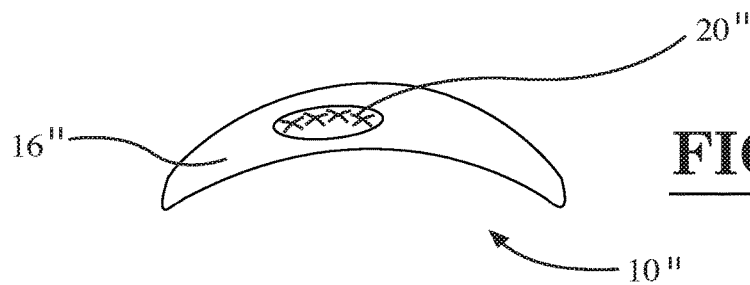
FIG. 3C is a partial side cross-sectional view of the eye of FIG. 3A, wherein a cross-linked donor cornea is shown being implanted in the location previously occupied by the scarred corneal tissue.

A third illustrative embodiment of a corneal transplant procedure with a cross-linked cornea is shown in FIGS. 3A-3C. Like the second embodiment described above, the corneal transplant procedure illustrated in FIGS. 3A-3C only involves replacing a scarred and/or diseased portion 16a" of the cornea 16" with a donor corneal portion. Thus, similar to the second embodiment explained above, FIGS. 3A-3C illustrate a lamellar keratoplasty procedure wherein only a portion of the cornea 16" of the eye 10" contains scarred and/or diseased tissue (i.e., a full-thickness corneal section is not removed). Although, in the procedure of FIGS. 3A-3C, an internal scarred and/or diseased portion 16a" of the cornea 16" is internally removed from the eye 10" of a patient, rather than being externally removed as in the second embodiment of FIGS. 2A-2C.

Referring initially to FIG. 3A, it can be seen that only an internal portion 16a" of the cornea 16" of the eye 10" is scarred and/or diseased. As such, in this embodiment, like the preceding second embodiment, it is not necessary to replace the entire thickness of the cornea 16" with a donor cornea, but rather just a portion of the cornea 16".

Next, referring to FIG. 3B, it can be seen that the scarred and/or diseased portion 16a" is being internally removed from the remainder of the cornea 16" using a pair of forceps 22 (i.e., mechanical means of removal are illustrated in FIG. 3B). Advantageously, because an internal approach is being utilized for removing the scarred and/or diseased portion 16a" of the cornea 16", the cornea 16" will not comprise the notch-like cavity 19 disposed in the outside or anterior surface of the cornea, which was described in conjunction with the preceding second embodiment. As described above for the first and second embodiments, the scarred and/or diseased corneal portion 16a" may be removed from the remainder of the cornea 16" using other suitable alternative means, such as laser cutting techniques (e.g., using a femtosecond laser). Advantageously, the femtosecond laser is capable of cutting inside the tissue without involving the surface of the tissue. The cut part of the tissue can then be removed by other means (e.g., micro-forceps).

Finally, as shown in FIG. 3C, after the scarred and/or diseased corneal portion 16a" has been removed from the remainder of the cornea 16" of the eye 10", the cross-linked donor cornea or cross-linked donor corneal portion 20" is implanted into the eye 10" of the patient in the location previously occupied by the scarred and/or diseased corneal portion 16a". After implantation of the cross-linked donor corneal portion 20", sutures or a suitable adhesive (e.g., the biocompatible and biodegradable adhesive described above) may be utilized to secure the cross-linked donor corneal portion 20" in place on the host cornea of the eye 10". Advantageously, the cross-linked donor corneal portion 20", which is strengthened by the cross-linking performed thereon, reinforces the cornea 16" and greatly reduces the likelihood of corneal graft rejection.

It is to be understood that the scarred and/or diseased corneal portion 16a" that is removed from the cornea 16" may also be replaced with stroma stem cells or mesenchymal stem cells, which can be contained in a medium, and then injected in the internal cavity previously occupied by the scarred and/or diseased corneal tissue 16a".

In one or more embodiments, mesenchymal stem cells also may be injected inside the donor cornea before or after transplantation. In addition, in one or more embodiments, daily drops of a Rho Kinase inhibitor may be added to the host eye after the surgery. The use of a medication, such as a Rho Kinase inhibitor, with the stem cells will encourage stem cell proliferation.

A fourth illustrative embodiment of a corneal transplant procedure with a cross-linked cornea is shown in FIGS. 4A-4E. Like the second and third embodiments described above, the corneal transplant procedure illustrated in FIGS. 4A-4E only involves replacing a scarred and/or diseased portion 16a'" of the cornea 16'" with a donor corneal portion. Thus, similar to the second and third embodiments explained above, FIGS. 4A-4E illustrate a lamellar keratoplasty procedure wherein only a portion of the cornea 16'" of the eye 10'" contains scarred and/or diseased tissue (i.e., a full-thickness corneal section is not removed). Although, in the procedure of FIGS. 4A-4E, a different-shaped scarred and/or diseased portion 16a'" of the cornea 16'" is removed.

Figure 4A:
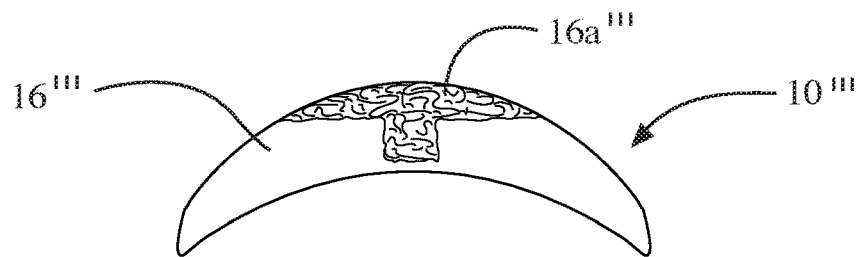
FIG. 4A is a partial side cross-sectional view of an eye having a T-shaped corneal scar and/or diseased tissue portion.

Referring initially to FIG. 4A, it can be seen that only a portion 16a" 'of the cornea 16"' having a T-shape or "top hut" shape is scarred and/or diseased. As such, in this embodiment, it is not necessary to replace the entire thickness of the cornea 16'" with a donor cornea as was described above in conjunction with FIGS. 1A-1D, but rather just a portion 16a'" of the cornea 16". In this illustrative embodiment, the back side of the cornea 16'" is maintained (see e.g., FIG. 4D).

Figure 4B:
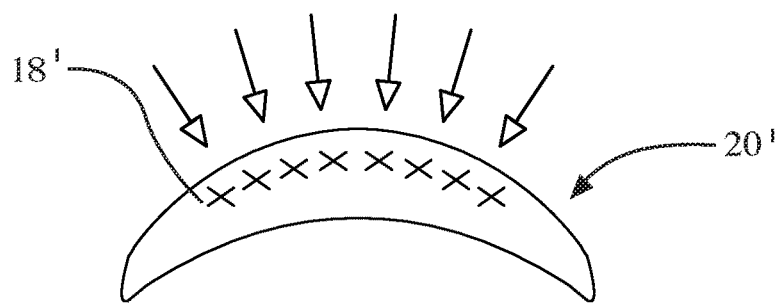
FIG. 4B is another partial side cross-sectional view of a donor cornea undergoing cross-linking.
Figure 4C:
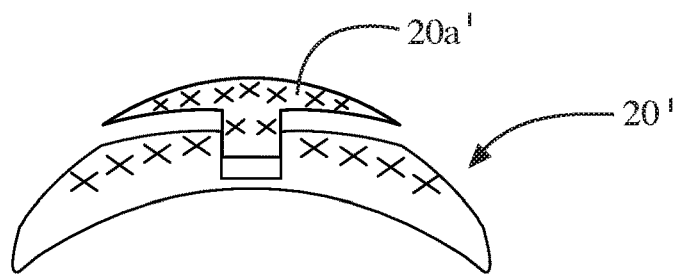
FIG. 4C is a partial side cross-sectional view illustrating a T-shaped portion of the cross-linked donor cornea being cut out from a remainder of the donor cornea.
Figure 5A:
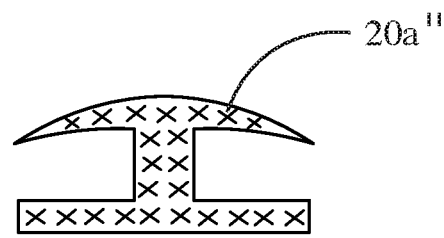
FIG. 5A illustrates an alternative configuration for the cross-linked donor cornea implant, wherein the donor cornea implant has a dumbbell shape.
Figure 5B:
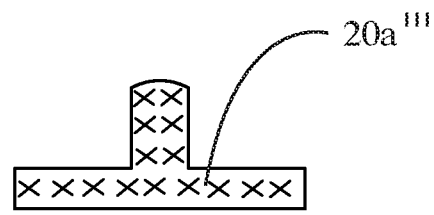
FIG. 5B illustrates another alternative configuration for the cross-linked donor cornea implant, wherein the donor cornea implant has a reversed or upside down T-shape.

In FIG. 4B, the cross-linking 18' of the clear donor cornea 20' is diagrammatically illustrated. As mentioned above, it is to be understood that all or just a part of the donor cornea 20' may be cross-linked. Then, in FIG. 4C, it can be seen that a portion 20a' of the clear donor cornea 20', which has a T-shape or "top hut" shape that matches the shape of the scarred and/or diseased portion 16a'" of the cornea 16'", is cut out from the remainder of the clear donor cornea 20' such that it has the necessary shape. In one or more embodiments, the portion 20a' may be cut from the clear donor cornea 20' and appropriately shaped using a femtosecond laser. As shown in FIGS. 5A and 5B, other suitably shaped cross-linked corneal portions may be cut from the clear donor cornea 20', such as a dumbbell-shaped corneal portion 20a" (see FIG. 5A) or a corneal portion 20a''' having a reversed T-shape or "reversed top hut" shape (see FIG. 5B), in order to accommodate correspondingly shaped scarred and/or diseased areas in the host cornea.

Figure 4D:
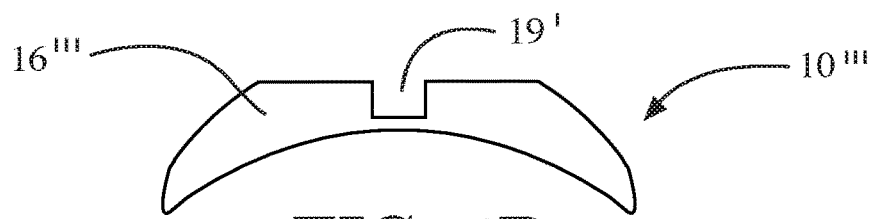
FIG. 4D is a partial side cross-sectional view of the eye of FIG. 4A, wherein the T-shaped scarred and/or diseased portion of corneal tissue has been removed from the eye.

Next, referring to FIG. 4D, it can be seen that the scarred and/or diseased portion 16a''' having the T-shape or "top hut" shape has been removed from the cornea 16''' of the eye 10''' such that the cornea 16''' comprises a cavity 19' disposed therein for receiving the donor cornea. As described above for the first three embodiments, the scarred and/or diseased corneal portion 16a''' may be removed from the remainder of the cornea 16''' using various suitable means, such as mechanical means or the laser cutting means (e.g., femtosecond laser) described above.

Figure 4E:
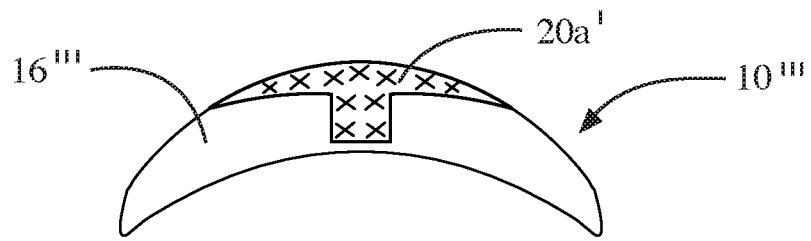
FIG. 4E is a partial side cross-sectional view of the eye of FIG. 4A, wherein the cross-linked T-shaped donor cornea portion is shown being implanted in the location previously occupied by the scarred and/or diseased corneal tissue portion.

Finally, as shown in FIG. 4E, after the scarred and/or diseased portion 16a''' has been removed from the remainder of the cornea 16''' of the eye 10''', the cross-linked donor corneal portion 20a' is implanted into the eye 10''' of the patient in the location previously occupied by the scarred and/or diseased corneal portion 16a'''. Because the shape of the transplant corresponds to that of the removed portion 16a''' of the cornea 16''', the transplant sits comfortably in its position in the host cornea. As described above, after implantation of the cross-linked donor corneal portion 20a' into the eye 10''', sutures or a suitable adhesive (e.g., the biocompatible and biodegradable adhesive described above) may be utilized to secure the cross-linked donor corneal portion 20a' in place on the host cornea 16''' of the eye 10". For example, if a biocompatible and biodegradable adhesive is used to secure the cross-linked donor corneal portion 20a' in place in the cornea 16''' of the eye 10''', the edges of the donor corneal portion 20a' are coated with the biocompatible and biodegradable adhesive so as to give the transplant a reliable stability. In this case, it is desirable to have the attachment of the transplant maintained by the biocompatible and biodegradable adhesive for a period of months (i.e., it is desirable for the transplant to be secured in place by the biocompatible and biodegradable adhesive for as long as possible).

An illustrative embodiment of a corneal lenslet implantation procedure with a cross-linked cornea is shown in FIGS. 6A-6C and 7A-7C. Similar to the second, third, and fourth embodiments described above, FIGS. 6A-6C and 7A-7C illustrate a lamellar keratoplasty procedure wherein only a portion of the cornea 16'''' of the host eye 10'''' is removed during the procedure (i.e., a full-thickness corneal section is not removed). Although, the procedure of FIGS. 6A-6C and 7A-7C differs in several important respects from the abovedescribed procedures. In this embodiment, the corneal transplant is cross-linked in vitro. Then, using a femtosecond laser or an excimer laser, the surgeon carves out or ablates a three-dimensional (3D) corneal cross-linked augment from the donor cornea 20''' that exactly compensates for the refractive error of the recipient of the transplant. That is, the corneal cross-linked augment or inlay may be cut to the desired shape using a femtosecond laser, or the inlay may be shaped in vitro using an excimer laser prior to its implantation in the cornea 16'''' of the host eye 10''''. After making an internal pocket 28 in the recipient cornea 16'''' of the host eye 10'''' with a femtosecond laser, the cross-linked transplant is folded and implanted in a predetermined fashion inside the host's corneal pocket 28 to provide stability to the eye 10'''' having keratoconus, keratoglobus, a thin cornea or abnormal corneal curvature, thereby preventing future corneal ectasia in this eye 10'''' and correcting its refractive errors. Advantageously, the procedure of this embodiment comprises a lamellar cross-linked corneal transplantation, which additionally results in simultaneous correction of the refractive error of the eye 10'''' of the patient. As used herein, the term "lenslet" refers to a lens implant configured to be implanted in a cornea of an eye. The lens implant may be formed from an organic material, a synthetic material, or a combination of organic and synthetic materials.

Figure 6A:
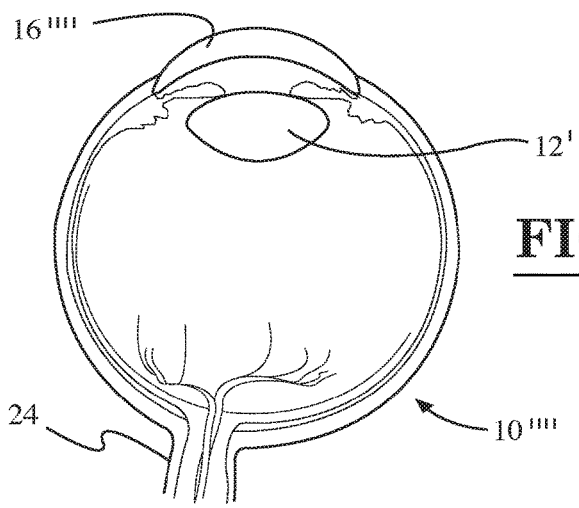
FIG. 6A is a side cross-sectional view of a host eye prior to an transplant procedure.
Figure 6B:
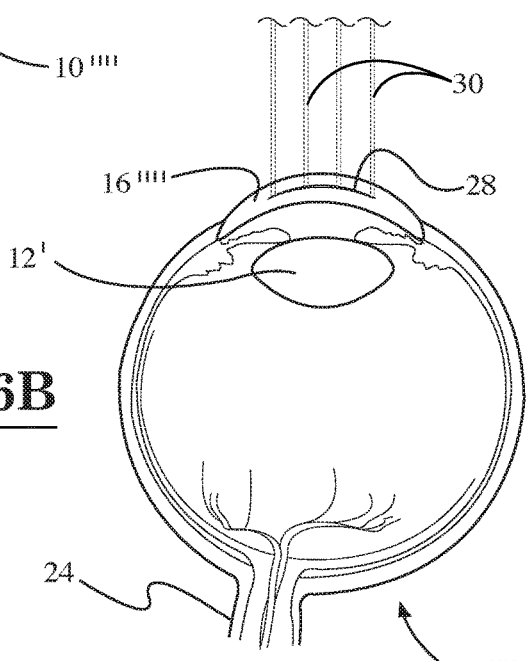
FIG. 6B is another side cross-sectional view of the host eye of FIG. 6A, which illustrates a creation of a corneal pocket therein.

Now, with reference to FIGS. 6A-6C and 7A-7C, the illustrative embodiment will be described in further detail. The host eye 10'''' with lens 12', cornea 16'''', and optic nerve 24 is shown in FIG. 6A, while the donor cornea 20''' is depicted in FIG. 7A. The donor cornea 20''' of FIG. 7A may be a cross-linked cornea of a cadaver or a tissue culture-grown cornea that has been cross-linked. Turning to FIG. 6B, it can be seen that an internal corneal pocket 28 is created in the cornea 16'''' of the host eye 10'''' (e.g., by using a suitable laser, which is indicated diagrammatically in FIG. 6B by lines 30).

Figure 7A:
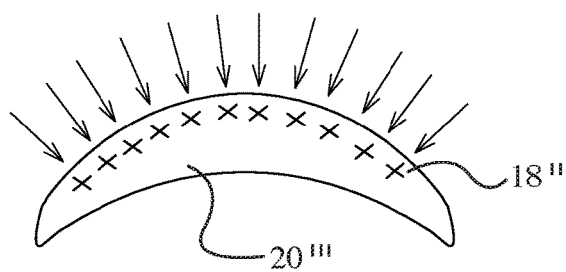
FIG. 7A is a partial side cross-sectional view of a donor cornea being cross-linked prior to being shaped for use in a transplant procedure.
Figure 7B:
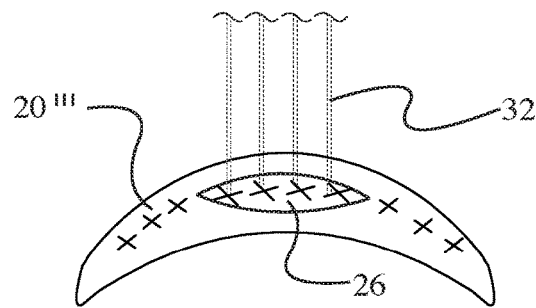
FIG. 7B is another partial side cross-sectional view of the donor cornea of FIG. 7A, which illustrates the cutting of a cross-linked lamellar lenslet from a remainder of the cross-lined donor cornea.
Figure 7C:
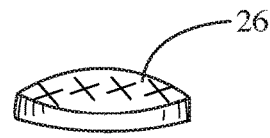
FIG. 7C is a side cross-sectional view of the cross-linked lamellar lenslet after it has been appropriately shaped and removed from the donor cornea of FIGS. 7A and 7B.

In FIG. 7A, the cross-linking 18" of the donor cornea 20''' is diagrammatically illustrated. As mentioned in the preceding embodiments, it is to be understood that all or just a part of the donor cornea 20''' may be cross-linked. Then, after the donor cornea 20''' of FIG. 7A has been cross-linked (e.g., by using a photosensitizer in the form of riboflavin and UV radiation as described above), it can be seen that a cross-linked lamellar lenslet 26 is cut out from the remainder of the donor cornea 20''' (e.g., by using a suitable laser, which is indicated diagrammatically in FIG. 7B by lines 32) such that it has the necessary shape for implantation into the host eye 10''. As explained above, the cross-linked lamellar lenslet 26 may be cut from the donor cornea 20''' and appropriately shaped using a femtosecond laser or an excimer laser. The cross-linked lamellar lenslet 26 is capable of being prepared to any requisite shape using either the femtosecond laser or the excimer laser. FIG. 7C illustrates the shaped cross-linked lamellar lenslet 26 after it has been removed from the remainder of the donor cornea 20".

Figure 6C:
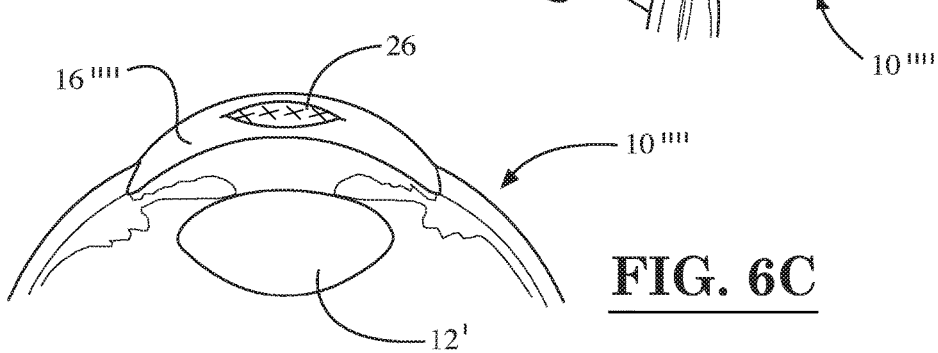
FIG. 6C is another side cross-sectional view of the host eye of FIG. 6A, which illustrates an implantation of the cross-linked lamellar lenslet into the host eye.

Finally, as shown in FIG. 6C, the cross-linked lamellar lenslet 26 is implanted into the cornea 16" of the host eye 10'''' of the patient in the location where the pocket 28 was previously formed. Because the shape of the transplant corresponds to that of the pocket 28 formed in the eye 10", the transplant sits comfortably in its position in the host cornea 16". As described above, after implantation of the cross-linked lamellar lenslet 26 into the eye 10'''', the refractive errors of the eye 10" have been corrected because the cross-linked lamellar lenslet 26 has been appropriately shaped to compensate for the specific refractive errors of the host eye 10" prior to its implantation into the eye 10". In addition, as explained above, the implantation of the cross-linked lamellar lenslet 26 provides additional stability to an eye having keratoconus, keratoglobus, a thin cornea, or abnormal corneal curvature.

Another illustrative embodiment of a corneal lenslet implantation procedure with a cross-linked cornea is shown in FIGS. 8-14. In general, the procedure illustrated in these figures involves forming a two-dimensional cut into a cornea of an eye; creating a three-dimensional pocket in the cornea of the eye, cross-linking the interior stroma, and inserting a lenslet or lens implant into the three-dimensional pocket after the internal stromal tissue has been cross-linked.

Figure 8:
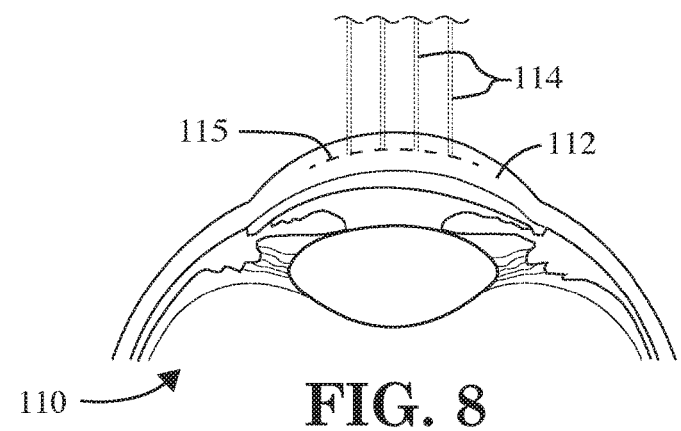
FIG. 8 is a partial side cross-sectional view illustrating the formation of a two-dimensional cut into a cornea of an eye, according to another embodiment of the invention.

Initially, in FIG. 8, the forming of a two-dimensional cut 115 into the cornea 112 of the eye 110 is diagrammatically illustrated. In particular, as shown in the illustrative embodiment of FIG. 8, the two-dimensional cut 115 is formed by making an intrastromal incision in the cornea 112 of the eye 110 using a femtosecond laser (i.e., the incision is cut in the cornea 112 using the laser beam(s) 114 emitted from the femtosecond laser). Alternatively, the two-dimensional cut 115 may be formed in the cornea 112 of the eye 110 using a knife.

Figure 9:
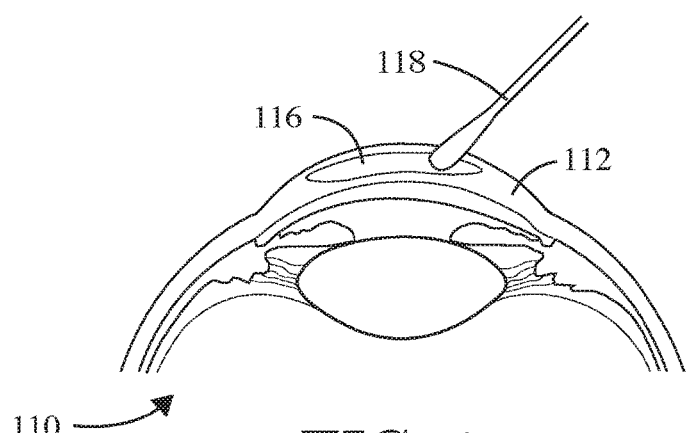
FIG. 9 is another partial side cross-sectional view of the eye of FIG. 8, which illustrates the creation of a three-dimensional pocket in the cornea of the eye.

Then, in FIG. 9, the forming of a three-dimensional corneal pocket 116 in the cornea 112 of the eye 110 is diagrammatically illustrated. In particular, as shown in the illustrative embodiment of FIG. 9, the three-dimensional corneal pocket 116 is formed by using a spatula 118. The formation of the intracorneal pocket 116 in the cornea 112 of the eye 110 allows one to gain access to the tissue surrounding the pocket 116 (i.e., the interior stromal tissue surrounding the pocket 116).

Turning again to FIGS. 8 and 9, in the illustrative embodiment, the corneal pocket 116 formed in the cornea 112 of the eye 110 may be in the form of an intrastromal corneal pocket cut into the corneal stroma. A femtosecond laser may be used to form a 2-dimensional cut into the cornea 112, which is then opened with a spatula 118 to create a 3-dimensional pocket 116. In one embodiment, a piece of the cornea 112 or a cornea which has a scar tissue is first cut with the femtosecond laser. Then, the cavity is cross-linked before filling it with an implant or inlay 128 to replace the lost tissue with a clear flexible inlay or implant 128 (see FIG. 12).

In one embodiment, a three-dimensional (3D) uniform circular, oval, or squared-shaped corneal pocket 116 is cut with a femtosecond laser and the tissue inside the pocket is removed to produce a three-dimensional (3D) pocket 116 to be cross-linked with riboflavin and implanted with a prepared implant.

Figure 10:
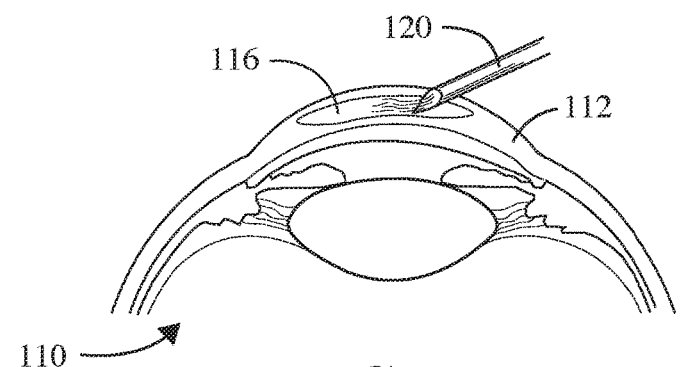
FIG. 10 is yet another partial side cross-sectional view of the eye of FIG. 8, which illustrates the injection of a photosensitizer into the three-dimensional pocket in the cornea of the eye.

After the pocket 116 is formed using the spatula 118, a photosensitizer is applied inside the three-dimensional pocket 116 so that the photosensitizer permeates the tissue surrounding the pocket 116 (see FIG. 10). The photosensitizer facilitates the cross-linking of the tissue surrounding the pocket 116. In the illustrative embodiment, the photosensitizer is injected with a needle 120 inside the stromal pocket 116 without lifting the anterior corneal stroma so as to cover the internal surface of the corneal pocket 116. In one or more embodiments, the photosensitizer or cross-linker that is injected through the needle 120 inside the stromal pocket comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 116 may be aspirated through the needle 120 until all, or substantially all, of the excess portion of the photosensitizer is removed from the pocket 116 (i.e., the excess cross-linker may be aspirated through the same needle so that the pocket 116 may be completely emptied or substantially emptied).

Figure 11A:
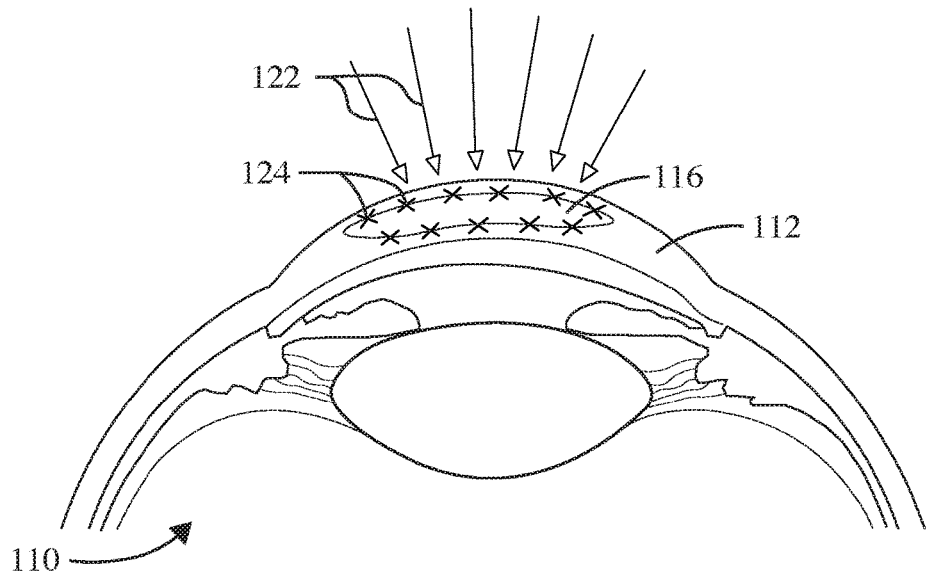
FIG. 11A is still another partial side cross-sectional view of the eye of FIG. 8, which illustrates the irradiation of the stromal tissue surrounding the three-dimensional pocket of the eye using ultraviolet radiation delivered from outside of the cornea.

Next, turning to the illustrative embodiment of FIG. 11A, shortly after the photosensitizer is applied inside the pocket 116, the cornea 112 of the eye 110 is irradiated from the outside using ultraviolet (UV) radiation 122 so as to activate cross-linkers in the portion of the tissue surrounding the three-dimensional pocket 116, and thereby stiffen the cornea 112, prevent corneal ectasia of the cornea 112, and kill cells in the portion of the tissue surrounding the pocket 116. In the illustrative embodiment, the ultraviolet light used to irradiate the cornea 112 may have a wavelength between about 370 nanometers and about 380 nanometers (or between 370 nanometers and 380 nanometers). Also, in the illustrative embodiment, only a predetermined anterior stromal portion 124 of the cornea 112 to which the photosensitizer was applied is cross-linked (i.e., the surrounding wall of the corneal pocket 116), thereby leaving an anterior portion of the cornea 112 and a posterior stromal portion of the cornea 112 uncross-linked. That is, in the illustrative embodiment, the entire corneal area inside the cornea 112 exposed to the cross-linker is selectively cross-linked, thereby leaving the anterior part of the cornea 112 and the posterior part of the stroma uncross-linked. The portion of the cornea 112 without the cross-linker is not cross-linked when exposed to the UV radiation. In an alternative embodiment, the cornea 112 may be irradiated using wavelengths of light other than UV light as an alternative to, or in addition to being irradiated using the ultraviolet (UV) radiation 122 depicted in FIG. 11A. Also, microwave radiation may be used synergistically or additively to correct non-invasively the remaining refractive error(s) of the cornea.

Figure 11B:
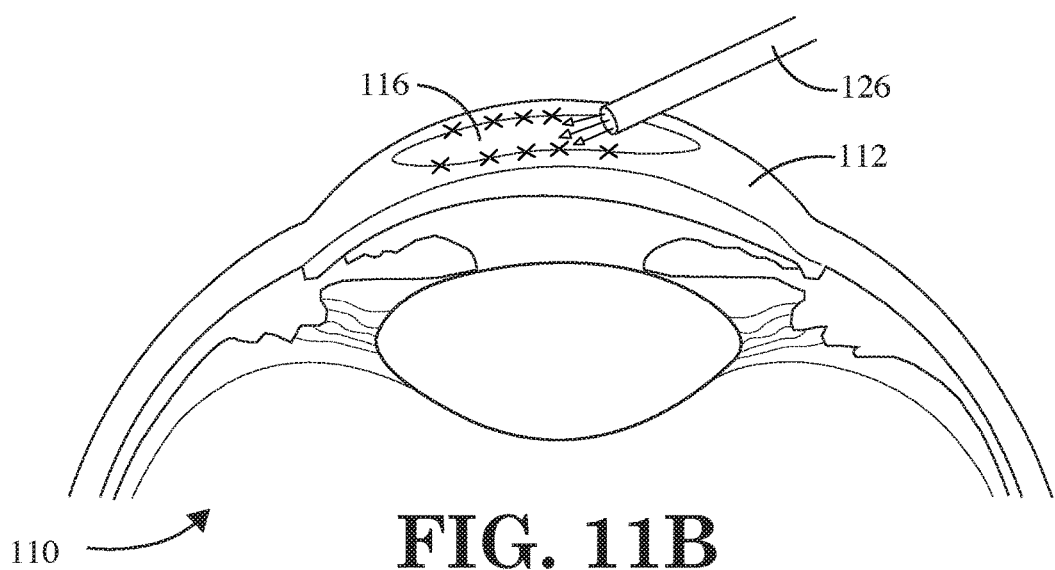
FIG. 11B is yet another partial side cross-sectional view of the eye of FIG. 8, which illustrates the irradiation of the stromal tissue surrounding the three-dimensional pocket of the eye using a fiber optic delivering ultraviolet radiation inside the three-dimensional pocket, according to an alternative embodiment of the invention.

Alternatively, as shown in FIG. 11B, a fiber optic 126 may be inserted into the corneal pocket 116 so as to apply the ultraviolet radiation and activate the photosensitizer in the wall of the corneal pocket 116. When the fiber optic 126 is used to irradiate the wall of the pocket 116, the ultraviolet radiation is applied internally, rather than externally as depicted in FIG. 11A.

Figure 12:
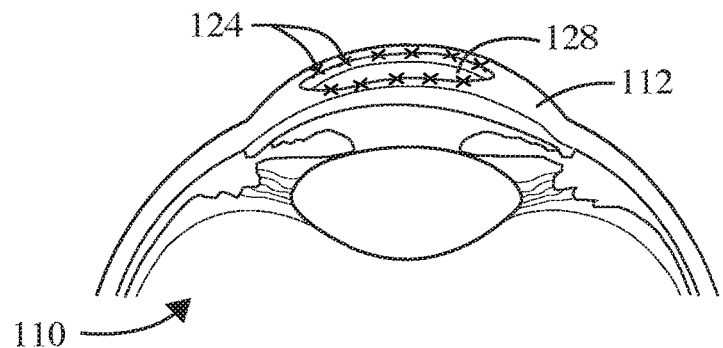
FIG. 12 is still another partial side cross-sectional view of the eye of FIG. 8, which illustrates a lens implant inserted into the pocket so as to change the refractive properties of the eye.

Now, with reference to FIG. 12, it can be seen that, after the wall of the corneal pocket 116 has been stiffened and is devoid of cellular elements by the activation of the cross-linkers, a lens implant 128 is inserted into the corneal pocket 116 in order to change the refractive properties of the eye. In particular, in the illustrated embodiment, the lens implant 128 is inserted through a small incision, and into the corneal pocket 116, using forceps or microforceps. In one or more embodiments, the lens implant 128 that is inserted inside the pocket 116 in the cornea 112 is flexible and porous. Also, in one or more embodiments, the lens implant 128 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymetacrylate, hydrogel, or a combination thereof. The surface of the lens implant 128 may have the appropriate shape to reshape the cornea 112 or the dioptric power to nullify the remaining spheric or astigmatic error of the eye. More particularly, in one or more embodiments, the lens implant 128 may have one of: (i) a concave surface to correct myopic refractive errors (i.e., a minus lens for correcting nearsightedness), (ii) a convex surface to correct hyperopic refractive errors (i.e., a plus lens for correcting farsightedness), or (iii) a toric shape to correct astigmatic refractive errors.

In the illustrative embodiment, the irradiation of the cornea 112 using the ultraviolet (UV) radiation 122 only activates cross-linkers in the portion of the stromal tissue surrounding the three-dimensional pocket 116, and only kills the cells in the portion of the tissue surrounding the pocket 116, so as to leave only a thin layer of cross-linked collagen to prevent an immune response and rejection of the lens implant 128 and/or encapsulation by fibrocytes, while preventing post-operative dry eye formation. In addition to preventing encapsulation of the lens implant 128 by fibrocytes, the cross-linking of the stromal tissue surrounding the pocket 116 also advantageously prevents corneal haze formation around the lens implant 128. That is, the cross-linking of the stromal tissue surrounding the lens implant 128 prevents formation of myofibroblast from surrounding keratocytes, which then convert gradually to fibrocytes that appear as a haze, and then white encapsulation inside the cornea, thereby causing light scattering in front of the patient's eye.

Figure 13:
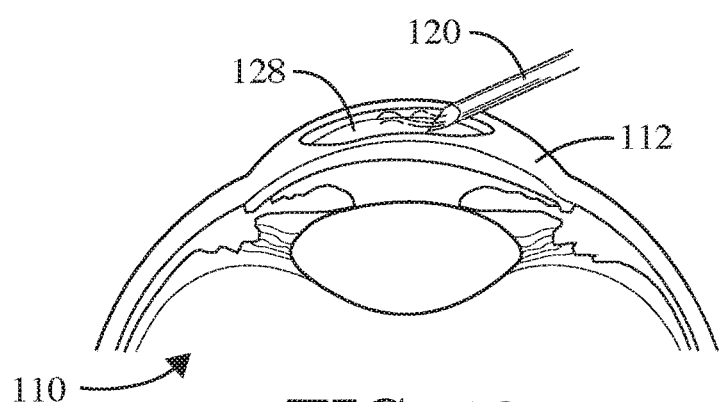
FIG. 13 is yet another partial side cross-sectional view of the eye of FIG. 8, which illustrates the reinjection of a photosensitizer into the three-dimensional pocket with the lens implant disposed therein so that the cross-linking procedure may be repeated.
Figure 14:
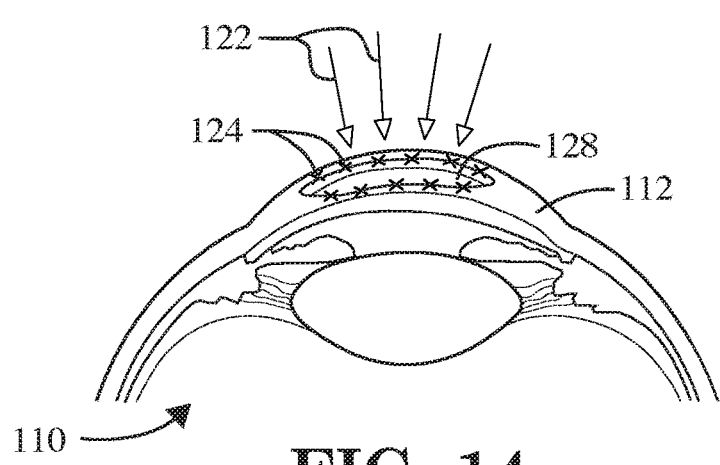
FIG. 14 is still another partial side cross-sectional view of the eye of FIG. 8, which illustrates the re-irradiation of the stromal tissue surrounding the three-dimensional pocket of the eye during the repetition of the cross-linking procedure.

As shown in FIGS. 13 and 14, the crosslinking procedure described above may be repeated after the lens implant 128 is implanted so as to prevent any cellular invasion in the area surrounding the implant 128. Initially, with reference to FIG. 13, the photosensitizer is reinjected inside the space between the lens implant 128 and the surrounding corneal tissue using a needle 120. In one or more embodiments, the needle 120 for injecting the photosensitizer may comprise a 30-32 gauge needle. Then, after the reinjection of the cross-linker, the cornea 112 is re-irradiated with ultraviolet radiation 122 to cross-link the tissue surrounding the lens implant 128 so as to prevent cellular migration towards the lens implant 128 (see FIG. 14).

In one or more embodiments, the lens implant or inlay 128 may be prepared ahead of time with known techniques, wherein the inlay 128 may be coated with a biocompatible material, such as collagen, elastin, polyethylene glycol, biotin, streptavidin, etc., or a combination thereof. The inlay 128 and the coating may be cross-linked with a photosensitizer or cross-linker, such as riboflavin, prior to being implanted into the pocket 116 in the cornea 112 of the eye.

In another embodiment, the lens implant or inlay 128 may be silicone, methacrylate, hydroxyethylmethacrylate (HEMA), or any other biocompatible transparent material, or a mixture thereof. The lens implant or inlay 128 also may be coated with materials, such as collagen or elastin, and may have a desired thickness of from 2 microns to 70 microns or more.

In yet another embodiment, the lens implant or inlay 128 is formed from an eye bank cornea, or a cross-linked eye bank cornea, etc. In general, there is a tremendous paucity of normal cadaver corneas for total or partial implants, such as for a corneal transplant of a corneal inlay. Because all the cellular elements are killed during the crosslinking of the corneal inlay, and because the corneal collagen is cross-linked and denatured, the remaining collagenous elements are not immunogenic when implanted inside the body or in the cornea of a patient. Advantageously, the prior cross-linking of the organic material, such as in the cadaver cornea, permits transplantation of the corneal inlay from an animal or human cornea or any species of animal to another animal or human for the first time without inciting a cellular or humoral response by the body, which rejects the inlay. Thus, cross-linking transparent cadaveric tissue for corneal transplantation, or as an inlay to modify of the refractive power of the eye, is highly beneficial to many patients who are on the waiting list for a corneal surgery. In addition, the surgery may be planned ahead of time without necessitating the urgency of the surgery when a fresh cadaver eye becomes available. In one or more embodiments, the collagens may be driven from the animal cornea, and cross-linked. Also, in one or more embodiments, the implant or inlay 128 may be made of cross-linked animal cornea or human cornea that is cut using a femtosecond laser to any desired shape and size, and then ablated with an excimer laser or cut with a femtosecond laser to a have a desired refractive power.

Figure 15:
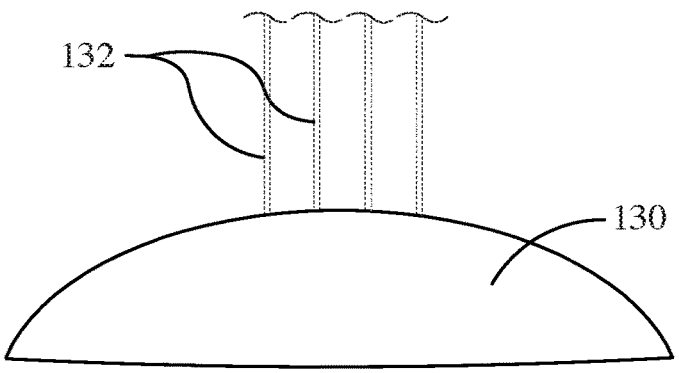
FIG. 15 is a side cross-sectional view illustrating the creation of a lens implant from an organic block of polymer using a excimer laser.
Figure 16:
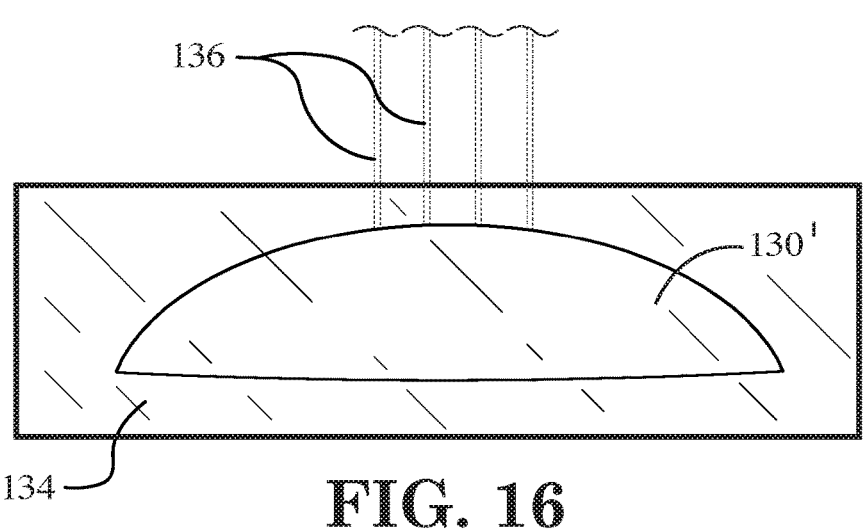
FIG. 16 is a side cross-sectional view illustrating the cutting of a lens implant from an organic block of polymer using a femtosecond laser.

For example, as shown in FIG. 15, the lens implant or inlay 130 may be formed from an organic block of a polymer (e.g., donor cornea) by cutting the lens implant 130 using an excimer laser (e.g., by using the laser beam(s) 132 emitted from the excimer laser). Alternatively, referring to FIG. 16, the lens implant or inlay 130' may be formed from an organic block 134 of a polymer (e.g., donor cornea) by cutting the lens implant 130' from the block 134 using a femtosecond laser or a computerized femto-system (e.g., by using the laser beam(s) 136 emitted from the femtosecond laser).

Figure 17:
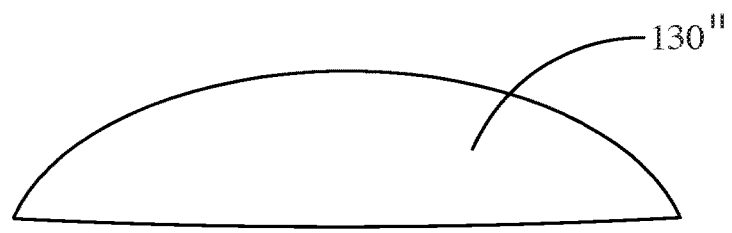
FIG. 17 is a side cross-sectional view illustrating a lens implant that has been formed using a three-dimensional printing technique or a molding technique.

In still another embodiment, as depicted in FIG. 17, the lens implant or inlay 130" is made using three-dimensional (3D) printing technology or a molding technique in order to form the lens implant or inlay 130" into the desired shape, size or thickness. The transparent material of the 3D-printed implant or inlay 130" may be coated with one or more biocompatible polymers and cross-linked prior to the implantation.

In yet another embodiment, after the implantation of an intraocular lens, the remaining refractive error of the eye may be corrected by the implantation of a lens implant or inlay 128 in the cross-linked pocket 116 of the cornea 112, thereby eliminating the need for entering the eye cavity to replace the original intraocular lens.

In still another embodiment, the remaining refractive error of the eye is corrected after an intraocular lens implantation by placing an inlay 128 on the surface of the cornea 112 of the patient while the shape of the cornea 112 is corrected with an excimer laser and wavefront optimized technology so that the patient is provided instant input on its effect on his or her vision. In this embodiment, an inlay similar to a contact lens is placed on the cornea 112 that, after correction, matches the desired refractive correction of the eye, and then, subsequently, the inlay 128 is implanted inside the cross-linked corneal pocket 116.

In yet another embodiment, the implant or inlay 128 may be ablated with an excimer laser for implantation in the cross-linked pocket 116, or after cross-linking the exposed corneal stroma in LASIK surgery.

In still another embodiment, a small amount of hyaluronic acid or a viscous fluid is injected into the pocket 116 prior to the implantation of the implant or inlay 128 so as to simplify the insertion of the implant or inlay 128 in the corneal pocket 116.

In yet another embodiment, the implant or inlay 128 is prepared having four marking holes of 0.1-2 millimeter (mm) in diameter in the inlay periphery at an equally sized distances so that the implant 128 may be rotated with a hook, if desired, after the implantation as needed to match the axis of an astigmatic error of the eye during the surgery as measured simultaneously with a wavefront technology system, such as an Optiwave Refractive Analysis (ORA) system or Holos® system, which are commercially available for measurement of astigmatism or its axis.

In still another embodiment, the implant or inlay 128 is located on the visual axis and may provide 1 to 3 times magnification for patients whose macula is affected by a disease process needing magnifying glasses for reading, such as in age-related macular degeneration, macular edema, degenerative diseases of the retina, etc. Because these eyes cannot be used normally for reading without external magnifier glasses, providing magnification by a corneal implant to one eye assists the patients in being able to read with one eye and navigate the familiar environment with their other eye.

In yet another embodiment, a part of the corneal stroma is removed from the eye of the patient, and its surface is corrected with an excimer laser to a desired refraction. Then, the removed part of the corneal stroma is cross-linked, and implanted back into the corneal pocket so as to correct the refractive power of the cornea.

In still another embodiment, the surface of the cornea 112 is treated after surgery in all cases daily with an anti-inflammatory agent, such as steroids, nonsteriodal anti-inflammatory drugs (NSAIDs), immune-suppressants, such as cyclosporine A or mycophenolic acid, anti-proliferative agents, antimetabolite agents, or anti-inflammatory agents (e.g., steroids, NSAIDS, or antibiotics etc.) to prevent inflammatory processes after the corneal surgery, inlay implantation or crosslinking, while stabilizing the integrity of the implant 128 and preventing future cell growth in the organic implant or the adjacent acellular corneal tissue. In this embodiment, the medication is injected in the corneal pocket 116 along with the implantation or the implant 128 is dipped in the medication first, and then implanted in the cross-linked corneal pocket 116.

In yet another embodiment, a cross-linked corneal inlay is placed over the cross-linked corneal stroma after a LASIK incision, and is abated to the desired size with an excimer laser using a topography guided ablation. By means of this procedure, the refractive power of the eye is corrected, while simultaneously providing stability to an eye prone to conceal ectasia postoperatively after a LASIK surgery. Then, the LASIK flap is placed back over the implant.

Figure 18:
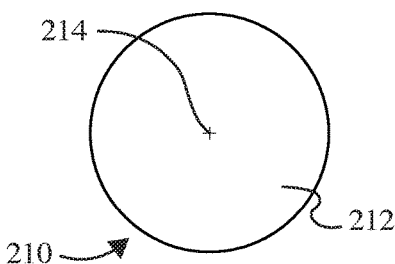
FIG. 18 is a front view of a cornea of an eye, according to yet another embodiment of the invention.

Yet another illustrative embodiment of a corneal lenslet implantation procedure with a cross-linked cornea is shown in FIGS. 18-23. In general, the procedure illustrated in these figures involves initially making an intrastromal square pocket surrounding the visual axis of the eye, and then, after forming the initial square pocket, a three-dimensional circular portion of diseased or weak stromal tissue is cut, removed, and replaced with a circular implant which fits into the circle that borders the four sides of the square. A front view of the cornea 212 of the eye 210 with the centrally-located visual axis 214 is illustrated in FIG. 18. Advantageously, in the illustrative embodiment of FIGS. 18-23, corneal tissue removal around the visual axis is greatly facilitated, and nearly perfect centration of the lens implant or inlay 220 about the visual axis is possible because the lens implant 220 fits within a depressed circular recess at the bottom of the pocket 216. As such, the undesirable decentering of the lens implant is prevented.

Figure 19:
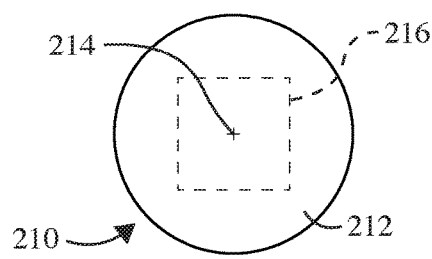
FIG. 19 is another front view of the cornea of the eye of FIG. 18, wherein a square-shaped intrastromal pocket has been formed in the cornea of the eye.

Initially, in FIG. 19, the forming of an intrastromal square-shaped pocket 216 surrounding the visual axis 214 (represented by a plus sign) in the cornea 212 of the eye 210 is diagrammatically illustrated. In particular, as shown in the illustrative embodiment of FIG. 19, the square-shaped pocket 216 is formed by making a two-dimensional intrastromal incision in the cornea 212 of the eye 210 using a femtosecond laser (i.e., the incision is cut in the cornea 212 using the laser beam(s) emitted from the femtosecond laser).

Figure 21:
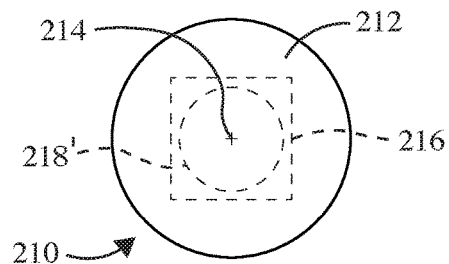
FIG. 21 is still another front view of the cornea of the eye of FIG. 18, wherein a circular three-dimensional portion of tissue having second diameter has been removed from the area within the square-shaped intrastromal pocket, the second diameter of the circular three-dimensional portion of tissue in FIG. 21 being larger than the first diameter of the circular three-dimensional portion of tissue in FIG. 20.
Figure 20:
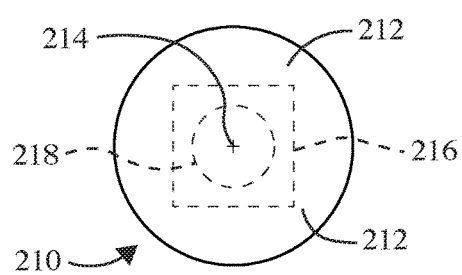
FIG. 20 is yet another front view of the cornea of the eye of FIG. 18, wherein a circular three-dimensional portion of tissue having a first diameter has been removed from the area within the square-shaped intrastromal pocket.

Then, in FIG. 20, the removal of a three-dimensional circular portion 218 of diseased or weak stromal tissue in the cornea 212 of the eye 210 is diagrammatically illustrated. In particular, as shown in the illustrative embodiment of FIG. 20, the three-dimensional circular stromal tissue portion 218 has a first diameter, which is less than a width of the square-shaped pocket 216 so that the three-dimensional circular stromal tissue portion 218 is disposed within the boundaries of the square-shaped pocket 216. The three-dimensional circular stromal tissue portion 218' depicted in FIG. 21 is generally similar to that illustrated in FIG. 20, except that the three-dimensional circular stromal tissue portion 218' depicted in FIG. 21 has a second diameter that is slightly larger than the first diameter of the three-dimensional circular stromal tissue portion 218 in FIG. 20. As such, the periphery of the three-dimensional circular stromal tissue portion 218' depicted in FIG. 21 is disposed closer to the square-shaped pocket 216, but still within the confines of the square-shaped pocket 216. In the illustrative embodiment, the three-dimensional circular stromal tissue portion 218, 218' may be removed using forceps or micro-forceps. In an exemplary embodiment, the diameter of the circular stromal tissue portion 218, 218' that is removed from the cornea 212 is between approximately 5 millimeters and approximately 8 millimeters, inclusive (or between 5 millimeters and 8 millimeters, inclusive).

In an alternative embodiment of the corneal lenslet implantation procedure, three (3) sequential cuts may be made in the stromal portion of the cornea 212 of the eye 210 using a femtosecond laser in order to form the pocket. First, a lower circular cut or incision centered about the visual axis (i.e., a lower incision with the patient in a supine position) is made using the femtosecond laser. Then, a second vertical cut is made above the lower incision using the femtosecond laser to form the side(s) of a circular cutout portion. Finally, a third square or circular cut (i.e., an upper incision) is made above the vertical cut using the femtosecond laser.

In the illustrative embodiment, the lower incision is parallel to the upper incision, and the vertical cut extends between lower incision and the upper incision. In this alternative embodiment, the three-dimensional circular stromal tissue cutout portion bounded by the lower incision on the bottom thereof, the vertical cut on the side(s) thereof, and the upper incision on the top thereof is removed from the cornea 212 of the eye 210 using a pair of forceps. A cavity formed by the upper incision facilitates the removal of the three-dimensional circular stromal tissue cutout portion. As described above, the third cut or incision formed using the femtosecond laser may be an upper circular cut that is larger than the lower circular cut, rather than an upper square cut that is larger than the lower circular cut.

Figure 22:
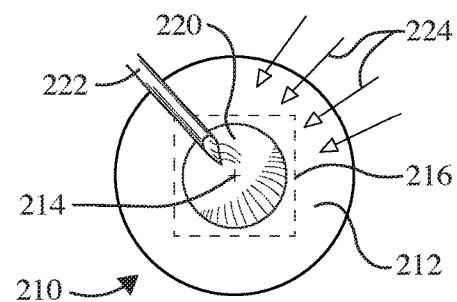
FIG. 22 is yet another front view of the cornea of the eye of FIG. 18, wherein a circular lens implant has been implanted in the area where the circular three-dimensional portion of tissue has been removed, and wherein a photosensitizer is being injected into the pocket in the cornea of the eye.

Turning to FIG. 22, after the three-dimensional circular stromal tissue portion 218, 218' is removed, a photosensitizer is applied inside the pocket 216 so that the photosensitizer permeates the tissue surrounding the pocket 216. The photosensitizer facilitates the cross-linking of the tissue surrounding the pocket 216. In the illustrative embodiment, the photosensitizer is injected with a needle 222 inside the stromal pocket 216. In one or more embodiments, the photosensitizer or cross-linker that is injected through the needle 222 inside the stromal pocket 216 comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 216 may be aspirated through the needle 222 until all, or substantially all, of the excess portion of the photosensitizer is removed from the pocket 216 (i.e., the excess cross-linker may be aspirated through the same needle 222 so that the pocket 216 may be completely emptied or substantially emptied).

Next, turning again to the illustrative embodiment of FIG. 22, shortly after the photosensitizer is applied inside the pocket 216, the cornea 212 of the eye 210 is irradiated from the outside using ultraviolet (UV) radiation 224 so as to activate cross-linkers in the portion of the tissue surrounding the three-dimensional pocket 216, and thereby stiffen the cornea 212, prevent corneal ectasia of the cornea 212, and kill cells in the portion of the tissue surrounding the pocket 216. In the illustrative embodiment, the ultraviolet light used to irradiate the cornea 212 may have a wavelength between about 370 nanometers and about 380 nanometers (or between 370 nanometers and 380 nanometers). Also, in the illustrative embodiment, only a predetermined anterior stromal portion of the cornea 212 to which the photosensitizer was applied is cross-linked (i.e., the surrounding wall of the corneal pocket 216), thereby leaving an anterior portion of the cornea 212 and a posterior stromal portion of the cornea 212 uncross-linked. That is, in the illustrative embodiment, the entire corneal area inside the cornea 212 exposed to the cross-linker is selectively cross-linked, thereby leaving the anterior part of the cornea 212 and the posterior part of the stroma uncross-linked. The portion of the cornea 212 without the cross-linker is not cross-linked when exposed to the UV radiation. In an alternative embodiment, the cornea 212 may be irradiated using wavelengths of light other than UV light as an alternative to, or in addition to being irradiated using the ultraviolet (UV) radiation 224 depicted in FIG. 22. Also, microwave radiation may be used synergistically or additively to correct non-invasively the remaining refractive error(s) of the cornea. In addition, in an alternative embodiment, the ultraviolet (UV) radiation may be applied after the implantation of the lens implant 220 to perform the crosslinking, rather than before the implantation of the lens implant 220 as described above. Further, rather than applying the ultraviolet (UV) radiation from outside the cornea 212, the stromal tissue of the pocket 216 may be irradiated from inside by means of a fiber optic, before or after the implantation of the lens implant 220.

Figure 23:
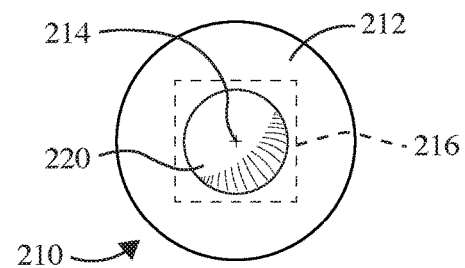
FIG. 23 is still another front view of the cornea of the eye of FIG. 18, wherein the circular lens implant is shown in the area where the circular three-dimensional portion of tissue was removed.

Now, with combined reference to FIGS. 22 and 23, it can be seen that, before or after the wall of the corneal pocket 216 has been stiffened and is devoid of cellular elements by the activation of the cross-linkers, a circular lens implant 220 is inserted into the circular recess at the bottom of the pocket 216 formed by the three-dimensional circular stromal tissue cutout portion 218, 218' that was removed. That is, the circular lens implant 220 fits within the periphery of the circular recess that borders the four sides of the squared-shaped pocket 216. In particular, in the illustrated embodiment, the circular lens implant 220 is inserted through a small incision, and into the circular recess at the bottom of the pocket 216 using forceps or microforceps. In the illustrative embodiment, the flexible lens implant 220 may be folded, inserted through the small incision, placed inside the circular recess at the bottom of the pocket 216, and finally unfolded through then small incision. In one or more embodiments, the lens implant 220 that is inserted inside the pocket 216 in the cornea 212 is flexible and porous. Also, in one or more embodiments, the lens implant 220 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymetacrylate, hydrogel, or a combination thereof.

Advantageously, the lens implant 220 of the aforedescribed illustrative embodiment always remains perfectly centered around the visual axis 214 of the eye 210, and will not move because it is disposed within the circular recess at the bottom of the pocket 216. As explained above, the lens implant 220 may be formed from an organic material, synthetic material, polymeric material, and combinations thereof. The lens implant 220 may replace either a diseased tissue or create a new refractive power for the eye 210, as explained hereinafter.

In the illustrative embodiment, the lens implant 220 may correct the refractive errors of the eye 210. The refractive error correction may be done by the lens implant 220 having a curvature that changes the corneal surface of the cornea 212. Alternatively, the lens implant 220 may have a different index of refraction that corrects the refractive power of the cornea 212. In the illustrative embodiment, the lens implant 220 may have the appropriate shape to reshape the cornea 212 or the dioptric power to nullify the remaining spheric or astigmatic error of the eye. More particularly, in one or more embodiments, the lens implant 220 may have one of: (i) a concave anterior surface to correct myopic refractive errors (i.e., a minus lens for correcting nearsightedness), (ii) a convex anterior surface to correct hyperopic refractive errors (i.e., a plus lens for correcting farsightedness), or (iii) a toric shape to correct astigmatic refractive errors.

In the illustrative embodiment, the irradiation of the cornea 212 using the ultraviolet (UV) radiation 224 only activates cross-linkers in the portion of the stromal tissue surrounding the three-dimensional pocket 216, and only kills the cells in the portion of the tissue surrounding the pocket 216, so as to leave only a thin layer of cross-linked collagen to prevent an immune response and rejection of the lens implant 220 and/or encapsulation by fibrocytes, while preventing post-operative dry eye formation. In addition to preventing encapsulation of the lens implant 220 by fibrocytes, the cross-linking of the stromal tissue surrounding the pocket 216 also advantageously prevents corneal haze formation around the lens implant 220. That is, the cross-linking of the stromal tissue surrounding the lens implant 220 prevents formation of myofibroblast from surrounding keratocytes, which then convert gradually to fibrocytes that appear as a haze, and then white encapsulation inside the cornea, thereby causing light scattering in front of the patient's eye.

It is readily apparent that the aforedescribed corneal transplant procedures offer numerous advantages. First, the implementation of the aforedescribed corneal transplant procedures reduces the likelihood that the implanted cornea will be rejected by the patient. Secondly, the aforedescribed corneal transplant procedures enable the clarity of the transplanted cornea to be preserved. Finally, the aforedescribed corneal transplant procedures reduce the likelihood that the transplanted cornea will be invaded by migrating cells, such as migrating cells that might initiate an immune response such as macrophage, lymphocytes or leucocytes or vascular endothelial cells. These types of migrating cells are discouraged by the cross-linked corneal collagen which does not provide an easily accessible tissue to invade. In addition, the use of abovedescribed tissue adhesives reduces the surgical procedure significantly. Moreover, the aforedescribed corneal lenslet implantation procedures modify the cornea so as to better correct ametropic conditions. Furthermore, the corneal lenslet implantation procedures described above prevent the lens implant from moving around inside the cornea once implanted, thereby ensuring that the lens implant remains centered about the visual axis of the eye.

With reference to the illustrative embodiment of FIGS. 24-29, an exemplary method of preventing capsular opacification and fibrosis utilizing an accommodative intraocular lens implant will be explained. In general, the procedure illustrated in FIGS. 24-29 involves treating patients in need of cataract surgery and a replacement intraocular lens.

Figure 24:
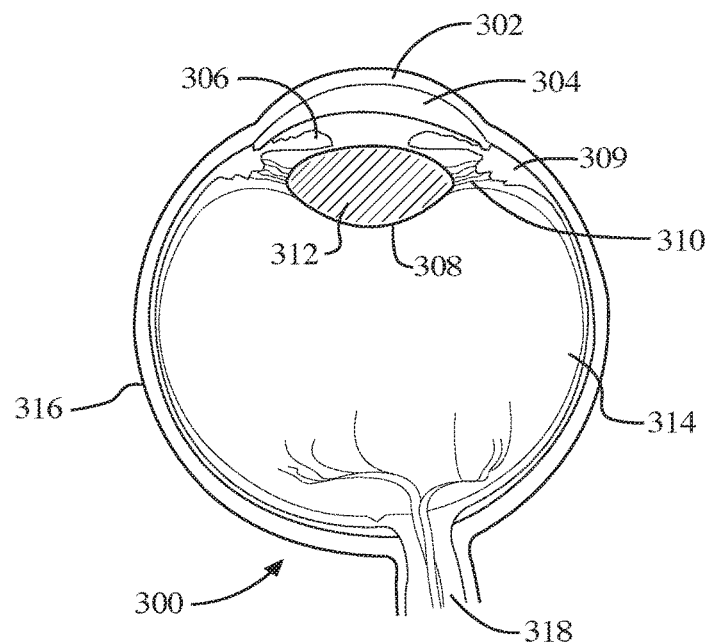
FIG. 24 is a side cross-sectional view illustrating an eye with a cataract, according to still another embodiment of the invention.

Initially, referring to FIG. 24, it can be seen that the eye 300 undergoing cataract surgery generally includes a cornea 302, an anterior chamber 304, an iris 306, a lens capsule or capsular bag 308, ciliary body 309, lens zonules 310, a vitreous cavity 314, a sclera 316, and an optic nerve 318. As shown in FIG. 24, the eye 300 has a cataract 312 (i.e., a cloudy lens), thereby requiring that cataract surgery be performed on the eye 300 of the patient.

Figure 25:
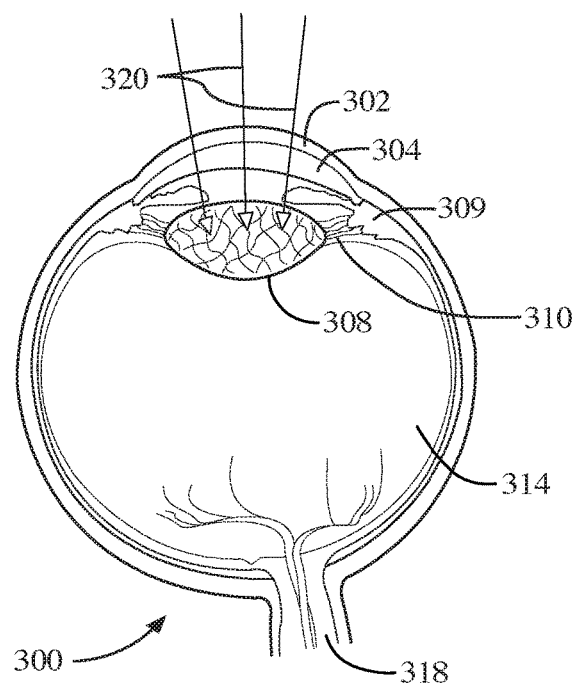
FIG. 25 is another side cross-sectional view of the eye of FIG. 24, which illustrates the breaking apart of the natural lens into lens fragments using a laser.

In FIG. 25, the first stage of the removal of the cortex and nucleus of the natural lens of the eye 300 containing the cataract 312 is diagrammatically illustrated. Specifically, in FIG. 25, the cloudy natural lens of the eye 300 is shown being broken apart into lens fragments by utilizing a femtosecond laser (i.e., the natural lens is broken apart by using the laser beam(s) 320 emitted from the femtosecond laser). The natural lens is initially broken apart into fragments so that it is capable of being more easily removed from the lens capsule 308 of the eye 300.

Figure 26:
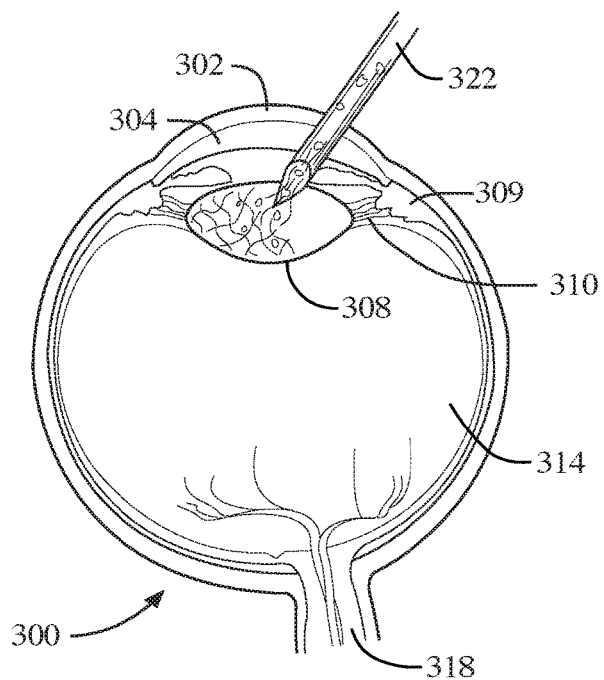
FIG. 26 is yet another side cross-sectional view of the eye of FIG. 24, which illustrates the irrigation and aspiration of the lens fragments of the natural lens using a probe.

Then, referring to FIG. 26, the second stage of the removal of the cortex and nucleus of the natural lens of the eye 300 containing the cataract 312 is diagrammatically shown. In particular, as depicted in FIG. 26, the lens fragments of the natural lens are being removed from the lens capsule 308 of the eye 300 using an ultrasonic probe 322. More particularly, the ultrasonic probe 322 irrigates and aspirates the lens fragments of the natural lens. In addition, the ultrasonic probe 322 may also be used to aspirate a substantial portion of the lens epithelium from the lens capsule 308 through an additional hole made in the lens capsule 308 and used as a bimanual system. That is, in the illustrative embodiment, the ultrasonic probe 322 may be used to aspirate as much of the lens epithelium as possible from the lens capsule 308 to prevent the undesirable propagation of lens epithelium cells following the cataract surgery.

Figure 27:
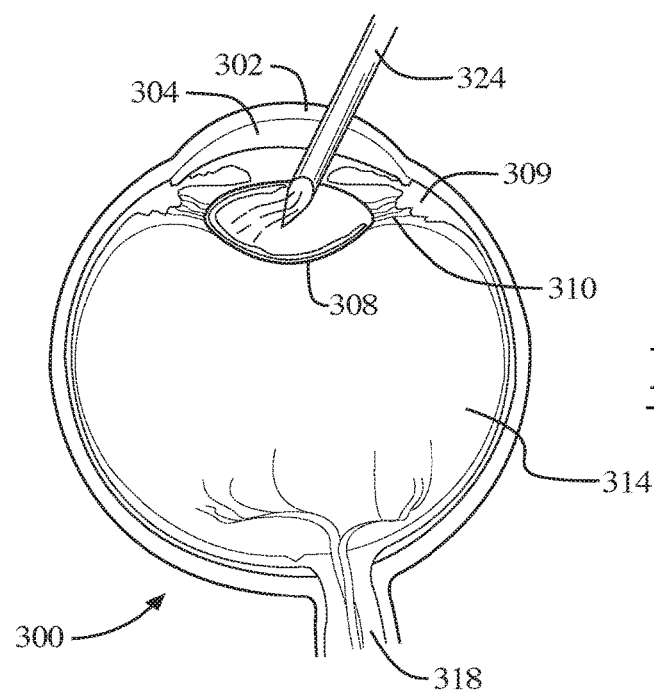
FIG. 27 is still another side cross-sectional view of the eye of FIG. 24, which illustrates the application of a photosensitizer to the capsular bag of the eye after the cataract has been removed.

Next, in FIG. 27, the injection of a cross-linker or photosensitizer (e.g., riboflavin) into the capsular bag 308 of the eye 300 is diagrammatically illustrated. In particular, as shown in the illustrative embodiment of FIG. 27, the cataract 312 has been removed from the capsular bag 308, which leaves the vast majority of the capsular bag 308 intact. Then, as shown in FIG. 27, a photosensitizer is applied inside the capsular bag 308 so that the photosensitizer permeates the tissue in both the anterior and posterior portions of the capsular bag 308. The photosensitizer facilitates the cross-linking of the tissue in the anterior and posterior portions of the capsular bag 308. In the illustrated embodiment of FIG. 27, the photosensitizer is injected with a needle 324 into the capsular bag 308 of the eye 300 by inserting the needle 324 through the anterior chamber 304 of the eye 300, and into the capsular bag 308 through the anterior wall of the capsular bag 308. In one or more embodiments, the photosensitizer or cross-linker that is injected through the needle 324 into the capsular bag 308 comprises riboflavin, and/or a biocompatible fluid having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the capsular bag 308 may be aspirated through the needle 324 until all, or substantially all, of the excess portion of the photosensitizer is removed from the capsular bag 308 (i.e., the excess cross-linker may be aspirated through the same needle 324 so that the capsular bag 308 may be completely emptied or substantially emptied). Also, in one or more embodiments, in order to kill the remaining lens epithelial cells that are generally attached to the rear side of the anterior portion of the lens capsule 308, the riboflavin may be in a relatively hypotonic solution that permits the lens cells to swell and makes them easier to remove or kill during the irradiation step described hereinafter.

Figure 28:
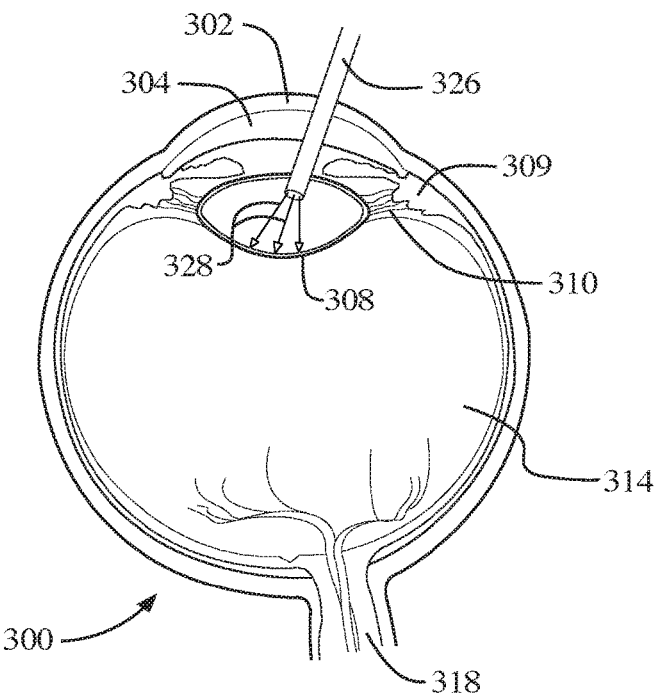
FIG. 28 is yet another side cross-sectional view of the eye of FIG. 24, which illustrates the irradiation of the capsular bag of the eye using a fiber optic so as to activate cross-linkers in the capsular bag.

Next, turning to FIG. 28, shortly after the photosensitizer is applied inside the capsular bag 308, the entire capsular bag 308 of the eye 300 (i.e., both the anterior portion and posterior portion of the lens capsule 308) is irradiated using a fiber optic 326 delivering ultraviolet (UV) radiation 328 so as to damage the remaining lens epithelial cells with UV laser light, thereby preventing capsular opacification and fibrosis. In the illustrative embodiment, the irradiation of the lens capsule 308 includes the anterior portion of the lens capsule 308 in order to prevent growth of the damaged lens epithelial cells and prevent cell migration and opacification because, in some cases, epithelial cells are still left in the lens capsule 308 after irrigation and aspiration of the lens fragments. Advantageously, the killing of the epithelial cells by irradiation prevents the further growth of the lens epithelial cells, and prevents their migration toward the posterior portion of the lens capsule 308 where they later become opaque. Also, in the illustrative embodiment, a painting technique may be utilized to deliver the ultraviolet light 328 to the capsular bag 308 of the eye 300 (i.e., the fiber optic 326 may be manipulated in such a manner by the surgeon so as to "paint" the ultraviolet light 328 on the capsular bag 308). Also, in the illustrative embodiment, ultraviolet (UV) radiation 328 may have a wavelength between about 370 nanometers and about 380 nanometers (or between 370 nanometers and 380 nanometers). In an alternative embodiment, the capsular bag 308 of the eye 300 may be irradiated using another wavelength of light as an alternative to, or in addition to being irradiated using ultraviolet (UV) radiation.

In an alternative embodiment, the anterior portion of the capsular bag 308 may be irradiated from outside the capsular bag 308 rather than from inside the capsular bag 308 as depicted in FIG. 28. In this embodiment, the fiber optic 326 may be disposed in the anterior chamber 304 of the eye 300 so that the ultraviolet (UV) light may be directed towards the anterior portion of the capsular bag 308. For example, the fiber optic 326 may be disposed at an acute angle relative to the capsular bag 308, but not perpendicular to the capsular bag 308 (so that the macula is protected and not damaged by the UV light emitted from the fiber optic 326).

Figure 29:
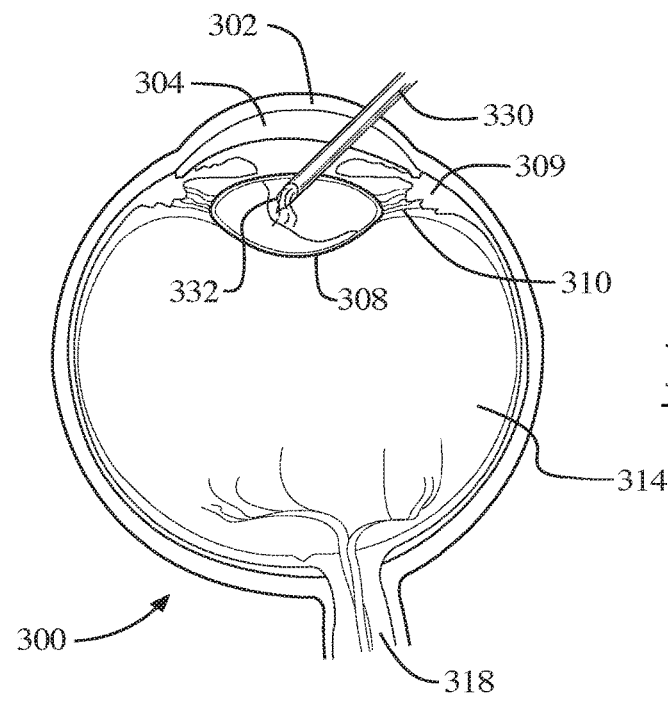
FIG. 29 is still another side cross-sectional view of the eye of FIG. 24, which illustrates the injection a transparent polymer into the lens capsule of the eye in order to form an accommodative intraocular lens for replacing the cortex and nucleus of the natural lens that was removed from the eye.

Finally, referring to FIG. 29, it can be seen that, after the tissue of the capsular bag 308 has been irradiated, a transparent polymer 332 is injected into the capsular bag 308 of the eye 300 using a needle 330 in order to form an accommodative intraocular lens implant for replacing the cortex and nucleus of the cloudy natural lens that was removed from the eye 300. In particular, in the illustrative embodiment, the needle 330 for injecting the transparent polymer 332 forming the accommodative intraocular lens is inserted into the capsular bag 308 of the eye 300 through an anterior hole or holes in the lens capsule 308. The hole or holes in the anterior chamber are plugged after the transparent polymer forming the accommodative intraocular lens hardens. In the illustrative embodiment, the transparent polymer that forms the accommodative intraocular lens remains flexible after the transparent polymer hardens or solidifies. Also, in the illustrative embodiment, after the transparent polymer that forms the accommodative intraocular lens is injected into the capsular bag 308 of the eye using the needle 330, the refractive power of the accommodative intraocular lens is adjusted using a wavefront technology unit intraoperatively so that the intraocular lens is able to be focused for a far distance without accommodation, and additionally is able to be focused for a near distance during accommodation by increasing the refractive power of the intraocular lens using the natural accommodative mechanism of the eye 300. Advantageously, intraoperative units utilizing wavefront technology are capable of indicating perfect refraction. During the injection process, both overfilling or under filling of the capsular bag 308 is not desirable because it does not provide proper refractive power for the lens and the eye 300.

In a further embodiment, the transparent polymer 332 that forms the accommodative intraocular lens implant is partially polymerized when injected into the capsular bag 308, and the transparent polymer becomes completely polymerized within a predetermined time period (e.g., within 5 to 20 minutes) after being injected into the capsular bag 308. In general, the polymerization time of the accommodative intraocular lens implant depends on the polymerization initiator that is used.

In one or more further embodiments, cataract surgery and glaucoma surgery with or without stent implantation may be done in a single session, wherein the photosensitizer is initially injected in the lens capsule after removal of the lens cortex and the nucleus. Then, a fiber optic is used to apply ultraviolet (UV) radiation so as to damage the lens epithelial cells and prevent their cellular proliferation. Immediately thereafter, the tissue around the surgical opening made in the eye wall during the glaucoma surgery with or without the shunt placement to drain the aqueous fluid outside the eye, is stained with the photosensitizer that was injected in the lens capsule. The photosensitizer migrates outside the eye through the surgical hole in the eye wall. The tissue, which is bathed by the photosensitizer (e.g., riboflavin), is then cross-linked with UV radiation applied through a fiber optic from the inside the eye or outside through the conjunctiva over the surgical hole or the shunt, regardless of the presence of a stent. The procedure achieves two goals simultaneously by preventing lens epithelial proliferation in the lens capsule, and by preventing fibroblast proliferation around the surgical hole of the tube.

Now, referring to the illustrative embodiment of FIGS. 30-41, an exemplary method for prevention of capsular opacification and fibrosis after cataract extraction, and for the prevention of fibrosis around a shunt or stent after glaucoma surgery will be explained. In general, the procedure illustrated in FIGS. 30-41 involves treating patients in need of both cataract surgery and glaucoma surgery. In the illustrative embodiment of FIGS. 30-41, the cataract and glaucoma surgeries are performed sequentially. However, as described hereinafter, the cataract and glaucoma surgeries may also be performed as two separate procedures. In these embodiments, the intraocular pressure (IOP) measurement is independent for a patient in need of cataract surgery and/or a glaucoma surgery.

Initially, referring to FIG. 30, it can be seen that the eye 400 undergoing cataract surgery generally includes a cornea 402, an anterior chamber 404, an iris 406, a lens capsule or capsular bag 408, lens zonules 410, a vitreous cavity 414, and a conjunctiva 416. As shown in FIG. 30, the eye 400 has a cataract 412 (i.e., a cloudy lens), thereby requiring that cataract surgery be performed on the eye 400 of the patient.

In FIG. 31, the injection of a photosensitizer (e.g., riboflavin) into the posterior portion of the capsular bag 408 of the eye 400 is diagrammatically illustrated. In particular, as shown in the illustrative embodiment of FIG. 31, the cataract 412 has been removed from the capsular bag 408, which leaves the posterior portion of the capsular bag 408 intact. Then, as shown in FIG. 31, a photosensitizer is applied inside the capsular bag 408 so that the photosensitizer permeates the tissue in the posterior portion of the capsular bag 408. The photosensitizer facilitates the cross-linking of the tissue in the posterior portion of the capsular bag 408. In the illustrated embodiment of FIG. 31, the photosensitizer is injected with a needle 418 into the capsular bag 408 of the eye 400 by inserting the needle 418 through the anterior chamber 404 of the eye 400, and into the capsular bag 408. In one or more embodiments, the photosensitizer or cross-linker that is injected through the needle 418 into the capsular bag 408 comprises riboflavin, and/or a biocompatible fluid having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the capsular bag 408 may be aspirated through the needle 418 until all, or substantially all, of the excess portion of the photosensitizer is removed from the capsular bag 408 (i.e., the excess cross-linker may be aspirated through the same needle 418 so that the capsular bag 408 may be completely emptied or substantially emptied).

Figure 32:
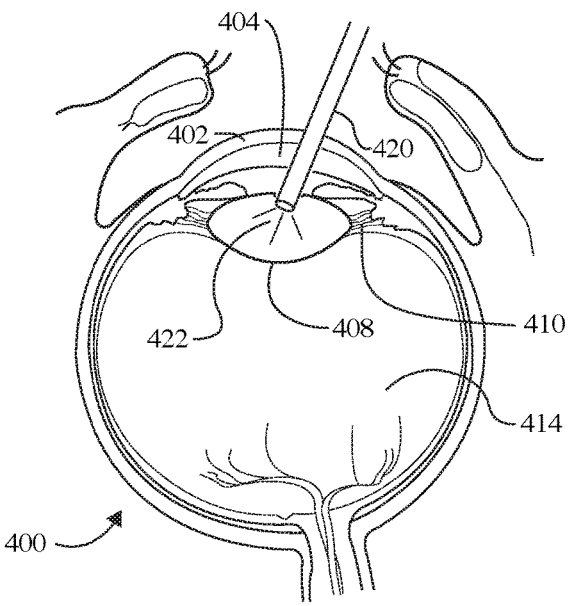
FIG. 32 is yet another side cross-sectional view of the eye of FIG. 30, which illustrates the irradiation of the posterior portion of the capsular bag of the eye so as to activate cross-linkers in the posterior portion of the capsular bag.

Next, turning to FIG. 32, shortly after the photosensitizer is applied inside the capsular bag 408, the remaining posterior portion of the capsular bag 408 of the eye 400 is irradiated using a fiber optic 420 delivering ultraviolet (UV) radiation 422 so as to damage the remaining lens epithelial cells with UV laser light, thereby preventing capsular opacification and fibrosis. In the illustrative embodiment, a painting technique may be utilized to deliver the ultraviolet light 422 to the posterior portion of the capsular bag 408 of the eye 400 (i.e., the fiber optic 420 may be manipulated in such a manner by the surgeon so as to "paint" the ultraviolet light 422 on the posterior portion of the capsular bag 408). Also, in the illustrative embodiment, ultraviolet (UV) radiation 422 may have a wavelength between about 370 nanometers and about 380 nanometers (or between 370 nanometers and 380 nanometers). In an alternative embodiment, the posterior portion of the capsular bag 408 of the eye 400 may be irradiated using another wavelength of light as an alternative to, or in addition to being irradiated using ultraviolet (UV) radiation.

Figure 33:
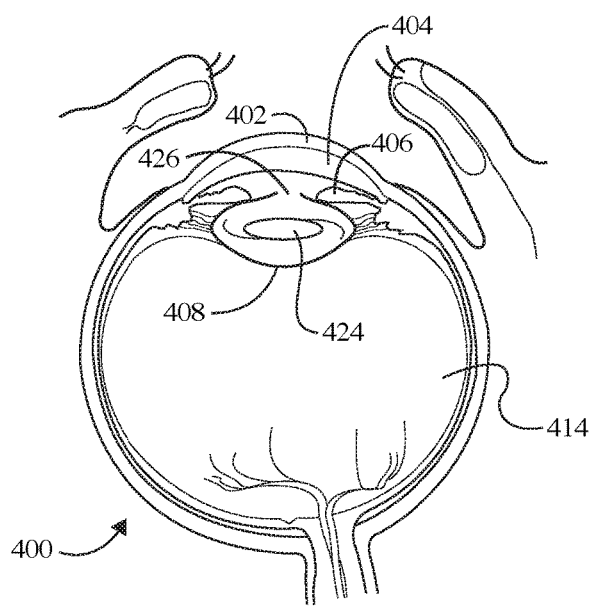
FIG. 33 is still another side cross-sectional view of the eye of FIG. 30, which illustrates the capsular bag of the eye after the removal of the cataract and the placement of an intraocular lens in the capsular bag.

Now, with reference to FIG. 33, it can be seen that, after the cataract 412 has been removed and the posterior portion of the capsular bag 408 has been irradiated, an intraocular lens 424 is implanted into the capsular bag 408 of the eye 400 in order to replace the cloudy natural lens that was removed. In particular, in the illustrative embodiment, the intraocular lens 424 is inserted into the capsular bag 408 of the eye 400 through the anterior opening 426 in the lens capsule 408.

Figure 34:
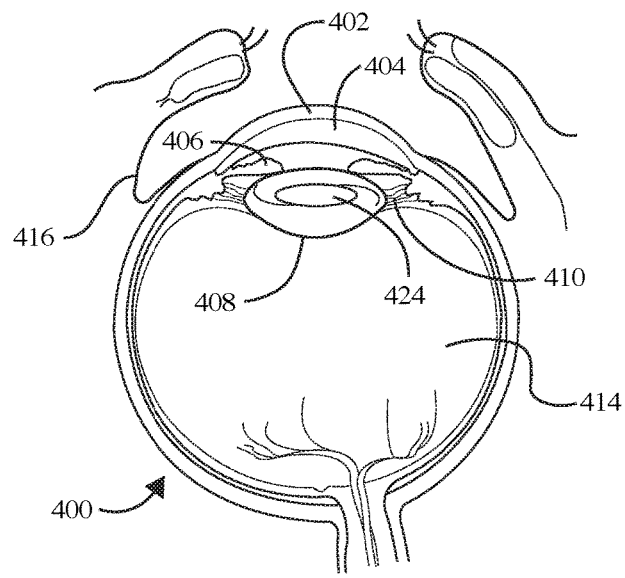
FIG. 34 is a yet another side cross-sectional view of the eye of FIG. 30, which illustrates the intraocular lens in the capsular bag of the eye prior to glaucoma surgery being performed on the eye.

Next, turning to FIGS. 34-38, the stent implantation and fibrosis prevention steps of the combined cataract extraction and glaucoma surgical procedure will be explained. Initially, the eye 400 with the implanted intraocular lens 424 therein is shown in FIG. 34.

Figure 35:
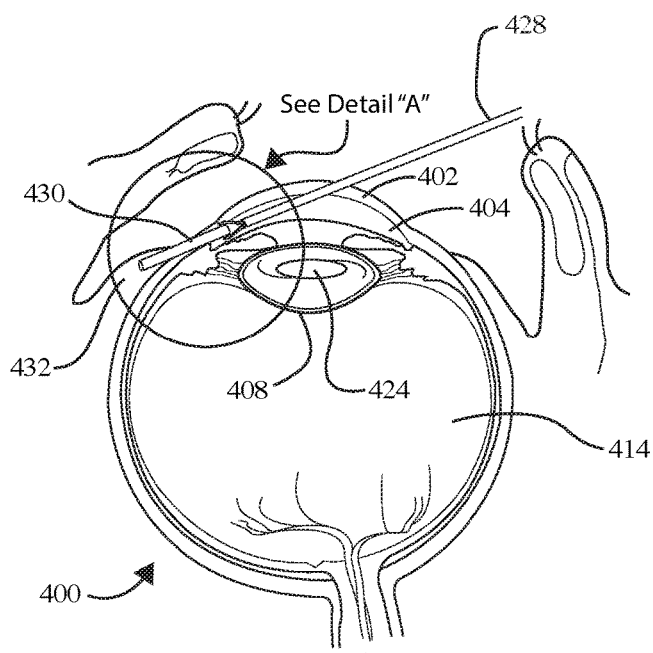
FIG. 35 is still another side cross-sectional view of the eye of FIG. 30, which illustrates the insertion of a stent through an anterior chamber of the eye and into the subconjunctival space.
Figure 36:
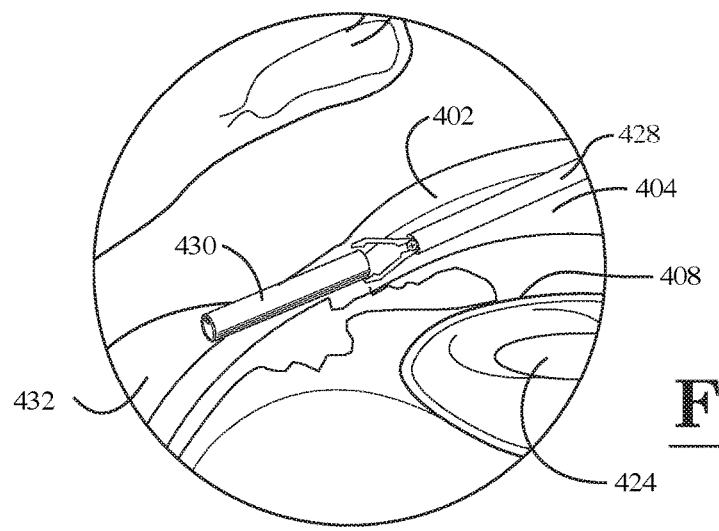
FIG. 36 is a partial, enlarged view illustrating the insertion of the stent in FIG. 35 (Detail "A")

In FIG. 35, the insertion of a glaucoma stent 430 through the anterior chamber 404, and into the subconjunctival space 432 of the eye 400 is diagrammatically illustrated. In particular, in the illustrated embodiment, the glaucoma stent 430 may be inserted into the subconjunctival space 432 of the eye 400 using a pair of forceps or microforceps 428. A detail view of the insertion of the glaucoma stent 430 is shown in FIG. 36. Once inserted, the glaucoma stent 430 extends from the anterior chamber 404 to the subconjunctival space 432.

Figure 37:
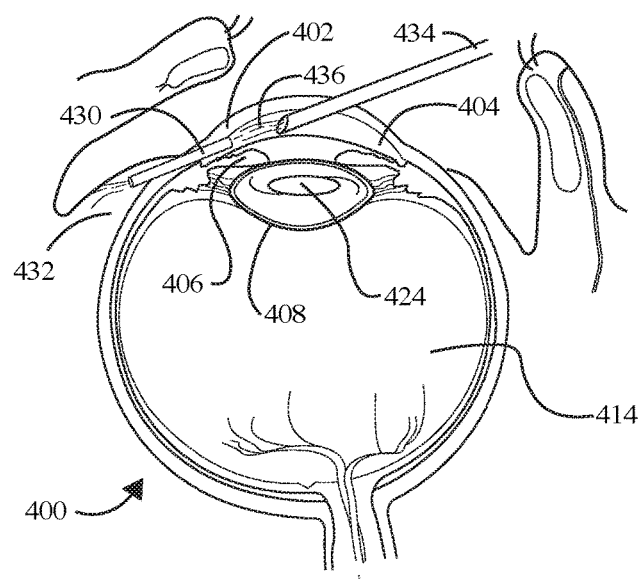
FIG. 37 is yet another side cross-sectional view of the eye of FIG. 30, which illustrates the application of a photo sensitizer to an anterior chamber of the eye so that the photosensitizer is capable of diffusing out of the stent and into the subconjunctival space.

Then, as shown in FIG. 37, the injection of a photosensitizer (e.g., riboflavin) into the anterior chamber 404 so that the photosensitizer diffuses into the tissue surrounding the glaucoma stent 430 is diagrammatically illustrated. In particular, as shown in the illustrative embodiment of FIG. 37, a photosensitizer is applied inside the anterior chamber 404 of the eye 400 and then a diffused stream 436 of the photosensitizer travels through the central opening of the glaucoma stent 430, and into the subconjunctival space 432 so that the photosensitizer permeates the tissue surrounding the glaucoma stent 430. The photosensitizer facilitates the cross-linking of the tissue surrounding the glaucoma stent 430. In the illustrated embodiment of FIG. 37, the photosensitizer is injected with a needle 434 into the anterior chamber 404 of the eye 400 by inserting the needle 434 into the anterior chamber 404 of the eye 400, and letting the photosensitizer diffuse through the central opening in the glaucoma stent 430. In one or more embodiments, the photosensitizer or cross-linker that is injected through the needle 434 into the anterior chamber 404 comprises riboflavin, and/or a biocompatible fluid having nanoparticles of riboflavin disposed therein. Preferably, the cross-linker has between about 0.1% riboflavin to about 100% riboflavin therein (or between 0.1% and 100% riboflavin therein).

Figure 38:
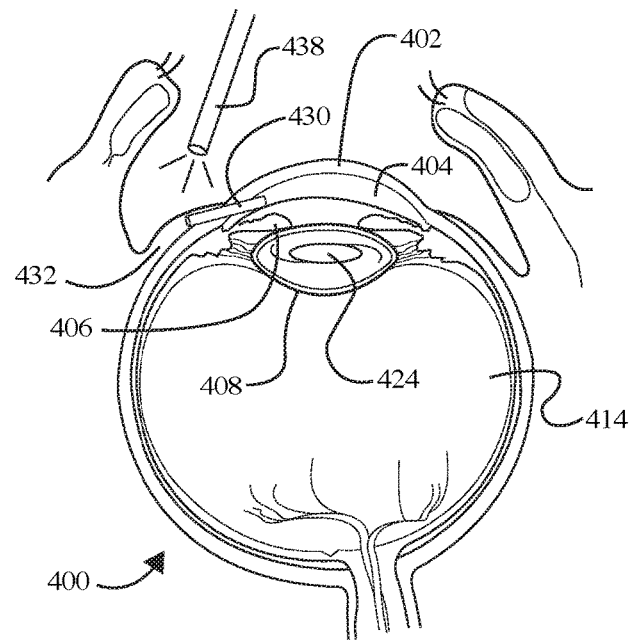
FIG. 38 is still another side cross-sectional view of the eye of FIG. 30, which illustrates the irradiation of the subconjunctival space so as to activate cross-linkers and prevent fibrosis around the stent outflow.

Next, turning to FIG. 38, shortly after the photosensitizer is applied inside the anterior chamber 404, the subconjunctival space 432 of the eye 400 is irradiated using a fiber optic 438 carrying ultraviolet (UV) light so as to cross-link the tissue surrounding the glaucoma stent 430, thereby preventing fibrosis around the stent 430 outflow. In the illustrative embodiment, a painting technique may be utilized to deliver the ultraviolet light to the subconjunctival space 432 of the eye 400 (i.e., the fiber optic 438 may be manipulated in such a manner by the surgeon so as to "paint" the subconjunctival space 432 with the ultraviolet light). Also, in the illustrative embodiment, ultraviolet (UV) radiation may have a wavelength between about 370 nanometers and about 380 nanometers (or between 370 nanometers and 380 nanometers). In an alternative embodiment, the subconjunctival space 432 of the eye 400 may be irradiated using another wavelength of light as an alternative to, or in addition to being irradiated using ultraviolet (UV) radiation.

Figure 39:
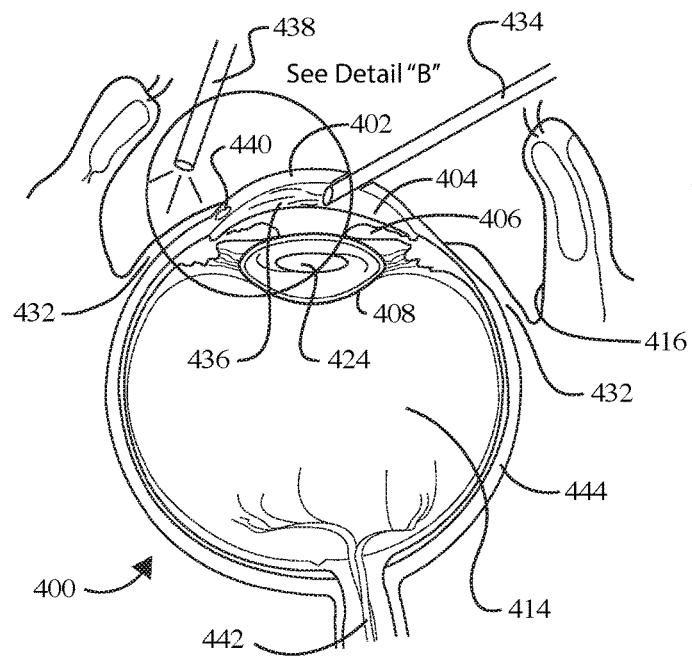
FIG. 39 is yet another side cross-sectional view of the eye of FIG. 30, which illustrates the application of a photo sensitizer to the anterior chamber of the eye and the irradiation of the subconjunctival space so as to activate cross-linkers and prevent fibrosis around a shunt or opening in the eye wall.
Figure 40:
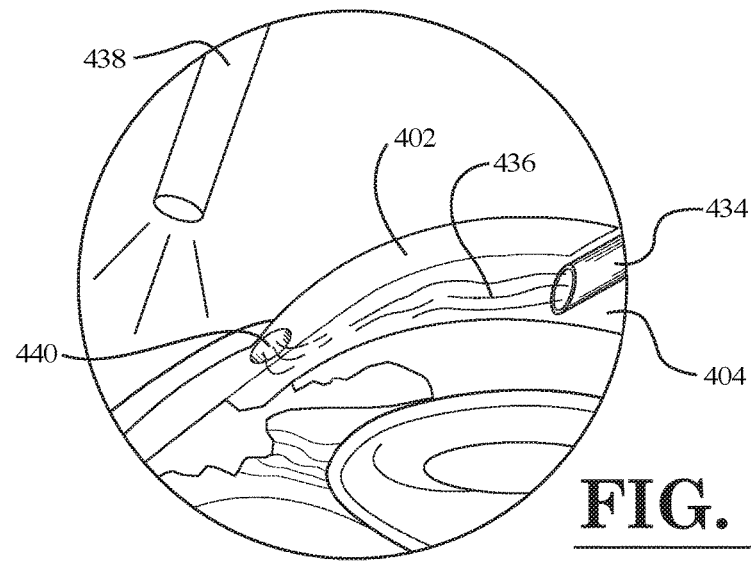
FIG. 40 is a partial, enlarged view illustrating the application of the photosensitizer and the irradiation of the space around the shunt or opening in the eye wall of FIG. 39 (Detail "B")

An alternative embodiment of the invention is depicted in FIG. 39. In particular, glaucoma drainage surgery is illustrated in FIG. 39. As shown in FIG. 39, the eye 400 undergoing glaucoma drainage surgery generally includes a cornea 402, an anterior chamber 404, an iris 406, a lens capsule or capsular bag 408 with an intraocular lens 424 disposed therein, a vitreous cavity 414, a conjunctiva 416, an optic nerve 442, and a sclera 444. Similar to the application of the photosensitizer described above with regard to FIG. 37, in the FIG. 39 embodiment, the photosensitizer (e.g., riboflavin in a biocompatible fluid) is injected into the anterior chamber 404 of the eye 400 using a needle 434. Then, a diffused stream 436 of the photosensitizer injected from the needle 434 travels through the opening or shunt 440 in the eye wall, and into the subconjunctival space 432 so that the photosensitizer permeates the tissue surrounding the opening or shunt 440. After which, with reference again to FIG. 39, the subconjunctival space 432 of the eye 400 is irradiated using a fiber optic 438 carrying ultraviolet (UV) light so as to cross-link the tissue surrounding the opening or shunt 440, thereby preventing fibrosis around the opening or shunt 440 outflow. A detail view of the application of the photosensitizer to the opening or shunt 440 is shown in FIG. 40. The opening or shunt 440 illustrated in FIGS. 39 and 40 is located in the angle of the eye between the iris 406 and the cornea 402. The opening or shunt 440 connects the anterior chamber 404 of the eye 400 to the subconjunctival space 432.

Figure 41:
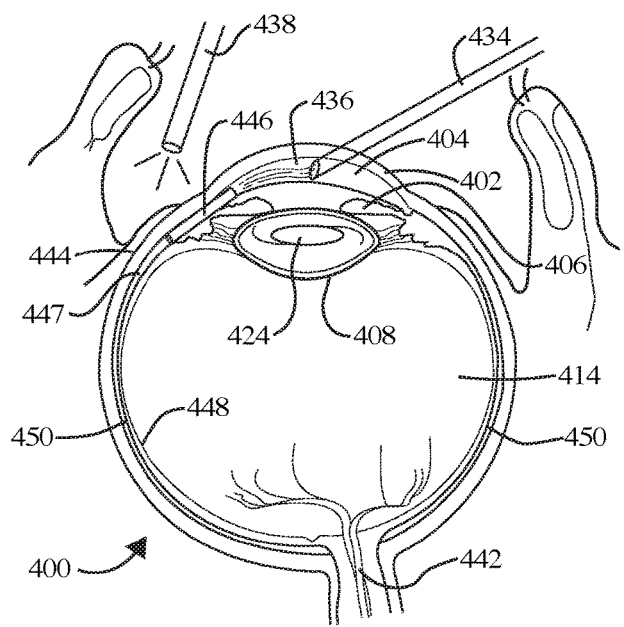
FIG. 41 is still another side cross-sectional view of the eye of FIG. 30, which illustrates the application of a photo sensitizer to the anterior chamber of the eye and the irradiation of the suprachoroidal space so as to activate cross-linkers and prevent fibrosis around a stent in the suprachoroidal space.
Figure 42:
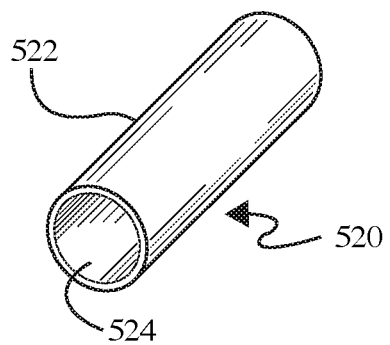
FIG. 42 is a perspective view illustrating a glaucoma stent having a coating provided thereon, according to an embodiment of the invention.

Another alternative embodiment of the invention is depicted in FIG. 41. In particular, a stent 446 positioned in the suprachoroidal space 447 of the eye 400 is illustrated in FIG. 41. More particularly, the glaucoma stent 446 in FIG. 41 extends from the angle of the anterior chamber 404 of the eye 400 to the suprachoroidal space 447. As shown in FIG. 41, the eye 400 undergoing glaucoma surgery generally includes a cornea 402, an anterior chamber 404, an iris 406, a lens capsule or capsular bag 408 with an intraocular lens 424 disposed therein, a vitreous cavity 414, an optic nerve 442, a sclera 444, a retina 448, and a choroid 450. Similar to the application of the photosensitizer described above with regard to FIG. 39, in the FIG. 41 embodiment, the photosensitizer (e.g., riboflavin in a biocompatible fluid) is injected into the anterior chamber 404 of the eye 400 using a needle 434. Then, a diffused stream 436 of the photosensitizer injected from the needle 434 travels through the glaucoma stent 446 in the suprachoroidal space 447 of the eye 400, and into the suprachoroidal space 447 so that the photosensitizer permeates the tissue surrounding the glaucoma stent 446. After which, with reference again to FIG. 41, the suprachoroidal space 447 of the eye 400 is irradiated using a fiber optic 438 carrying ultraviolet (UV) laser light so as to cross-link the tissue surrounding the glaucoma stent 446, thereby preventing fibrosis around the glaucoma stent 446 outflow.

In another embodiment, the application of the photosensitizer and the irradiation of the tissue surrounding the glaucoma stent 446 is repeated one or more additional times to cross-link the tissue surrounding the stent 446 again so as to prevent any cellular invasion in the area surrounding the stent 446.

In still another embodiment, the cataract surgery and the glaucoma surgery with or without stent implantation is done in two sessions. Initially, the photosensitizer is used to kill the lens epithelial cells using a fiber optic applying ultraviolet (UV) radiation, while in a subsequent glaucoma surgery with or without a stent, a photosensitizer (e.g., riboflavin) is injected in the anterior chamber after the glaucoma surgery with or without a stent and the wall of the outflow hole and the tissue in the subconjunctival space is then irradiated with ultraviolet (UV) light from the external side with a fiber optic in a painting fashion with the desired power to cross-link the collagenous tissue around the eye wall opening or around the stent to kill the cells, thereby preventing the cells from migrating in the surgical area and closing the outflow channel.

In yet another embodiment, in a previous glaucoma surgery involving a shunt or drainage tube, a minimal amount (e.g., 0.02 to 0.1 milliliters or less) of the photosensitizer (e.g., riboflavin) is injected in the anterior chamber of the eye so as to diffuse out of the surgically created hole or a shunt. Then, immediately thereafter, ultraviolet (UV) radiation is applied in an oscillatory painting fashion over the end of the drainage tube or stent, or over the surgically produced opening, at the desired power and duration in order to cross-link the tissue that comes into contact with the photosensitizer, etc.

In still another embodiment, the radiation is done shortly after injection of the photosensitizer (e.g., 5 to 60 seconds thereafter) or slightly longer after injection of the photosensitizer to prevent crosslinking or damage to the conjunctival superficial vessels or the conjunctival epithelial surface, so as to only cros slink the deeper laying tissue of the subtenon space or choroidal tissue immediately in contact with the photosensitizer over the pars plana. This process may be repeated to stabilize the tissue and further prevent tissue adhesion and encapsulation of the drainage shunt.

In one embodiment, the implant has a collagenous coating. The device may be in the form of a stent or a glaucoma drainage device connecting the fluid produced inside the eye to outside, either in the choroid or under the conjunctiva. The collagen coating can be conjugated with a photosensitizer that can be cross-linked after implantation with ultraviolet (UV) radiation or another wavelength of light that is applied to cross-link the collagen surrounding the implant, and to prevent cell growth or migration over the implant and encapsulation of the implant. Advantageously, by preventing cell growth or migration over the implant and the encapsulation of the implant, the aqueous fluid has unimpeded access to the subconjunctival space or the choroidal space.

In another embodiment, a collagen conjugated with a photosensitizer is injected surrounding the body of the implant after the stent or shunt implantation, and then the polymeric collagen and the surrounding tissue is cross-linked so as to provide an area for diffusion of fluid, and to kill the surrounding cells and prevent encapsulation of the implant or a part of it.

In yet another embodiment, the photosensitizer may be injected in the lens capsule after removal of the lens nucleus and the lens cortex so as to cross-link the remaining lens epithelial cells with ultraviolet (UV) light applied through a fiber optic in a painting fashion with an appropriate power to damage the epithelial cells prior to implantation of an intraocular lens (IOL), thereby preventing encapsulation and cell proliferation of the remaining epithelial lens cells in the lens capsule that create a fibrous-like encapsulation closing the space between the anterior and posterior leaflet of the remaining lens capsule or around an implanted intraocular lens. This cell proliferation causes a significant posterior capsular opacification about 3 to 12 months after cataract surgery in over 80% of the patients, or the implant may be tilted as a result of force applied to it, thus requiring laser surgery to cut the capsule open for the patient to have a clear view to the outside for uninterrupted light to reach the retina.

Now, referring to FIGS. 42-46, another embodiment of a glaucoma stent 520 and a surgical procedure using the stent 520 will be described. Initially, referring to the perspective view of the stent 520 in FIG. 42, it can be seen that the glaucoma stent 520 comprises a flexible tube with an external coating 522 disposed on the outside of the stent 520 and an internal coating 524 disposed on the inside of the stent 520. The external and internal stent coating 522, 524 is very important for the surgical procedure. Unless the external and internal stent coating 522, 524 is done with a substance, such as collagen, elastin, and/or polyethylene glycol (PEG), the stent 520 can irritate the surrounding tissue and excite cell migration and encapsulation. The coating may be applied to the stent 520 before or after the implantation of the stent 520. Preferably, the glaucoma stent 520 is formed from a solid, flexible, or semi-flexible material. For example, the stent material may be silicone-based or a mixture of polymers (e.g. acrylic and Hydroxyethyl methacrylate (HEMA), or HEMA alone, etc.) that preferably create a soft stent 520 for its placement under the conjunctiva of the eye. However, the stent 520 may also be implanted under the sclera of the eye. The glaucoma stent 520 may have a diameter between approximately 50 microns and approximately 700 microns (or between 50 microns and 700 microns), and the stent 520 may have a length between approximately 5 millimeters (mm) and approximately 15 millimeters (or between 5 millimeters and 15 millimeters). The diameter and the length of the stent 520 ultimately determine how much fluid is drained at a certain, desired intraocular pressure. This may also be decided by the doctor by him or her choosing a stent 520 that provides the desired pressure inside the patient's eye. In one embodiment, the glaucoma stent 520 may be three-dimensionally (3D) printed, and then coated as known in the art.

In one embodiment, the glaucoma stent 520 may be coated with a photosensitizer (e.g., riboflavin) before being implanted into the eye. Then, after the glaucoma stent 520 is implanted in the eye, the photosensitizer (e.g., riboflavin) may be released by the glaucoma stent 520 into the tissue surrounding the stent 520.

Figure 43:
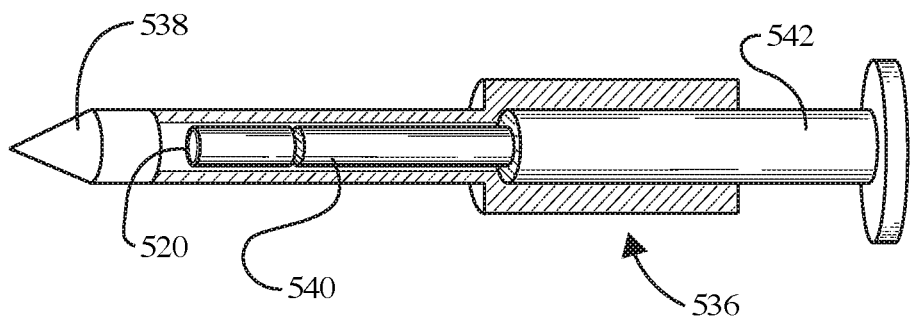
FIG. 43 is a side cross-sectional view illustrating a syringe used for the implantation of the stent of FIG. 42, according to an embodiment of the invention.

Next, turning to FIG. 43, a syringe 536 for implantation of the glaucoma stent 520 will be briefly described. As shown in FIG. 43, the syringe 536 comprises a sharp needle portion 538 for penetrating the tissue, a piston portion 540 for implanting the stent 520 into its desired location, and a plunger 542 for driving the piston 540, which in turn, drives the stent 520 into the tissue of the patient.

Now, referring to the illustrative embodiment of FIGS. 44-46, an exemplary surgical procedure using the stent 520 will be explained. Initially, referring to FIGS. 44-46, it can be seen that the eye 500 undergoing surgery generally includes a cornea 502, an anterior chamber 504, an iris 506, a lens capsule or capsular bag 508 with an intraocular lens 530 disposed therein, lens zonules 510, a vitreous cavity 512, a conjunctiva 514, a sclera 518, a retina 526, and an optic nerve 528.

Figure 44:
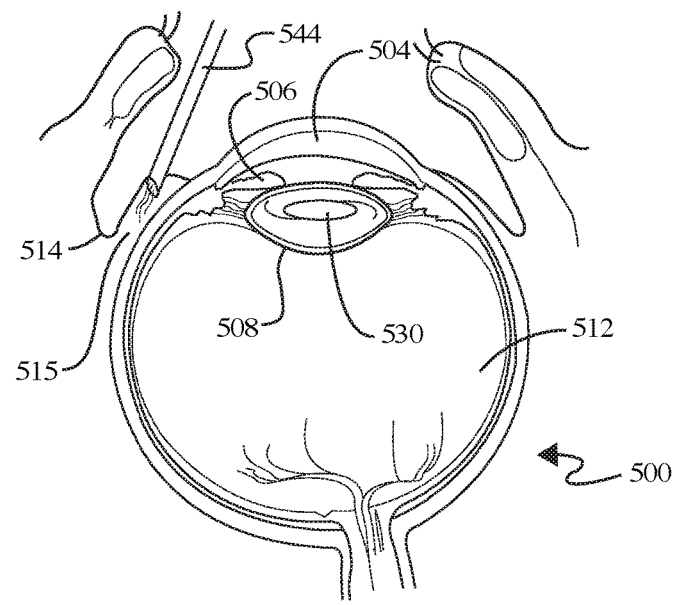
FIG. 44 is a side cross-sectional view of an eye, which illustrates the application of liquid collagen to the subconjunctival space, according to another embodiment of the invention.

In FIG. 44, liquid collagen and hyaluronic acid with or without a photosensitizer is initially injected in the subconjunctival space using a needle 544 so as to create a space (i.e., a bleb) for the stent 520. When the solution comprising the liquid collagen and the hyaluronic acid is subsequently cross-linked with ultraviolet light or another wavelength of light, a honeycomb structure is formed in the subconjunctival space around the stent outflow, thereby facilitating the draining of aqueous fluid from the stent. As such, when the stent 520 is subsequently positioned in liquid collagen that is cross-linked at the end of the surgery, the scar forming cells in the Tenon's capsule under the conjunctiva are killed, and the aqueous fluid is capable of diffusing through the stent 520.

Next, the glaucoma stent 520 is implanted into the conjunctiva 514 of the eye 500 using the syringe 536 described above. The syringe 536 is essentially loaded with the stent 520, and then the sharp needle portion 538 of the syringe 536 is used to penetrate the eye wall before the stent 520 is unloaded by the syringe 536. After the stent 520 is delivered into the tissue, the syringe 536 is withdrawn from the eye 500. Once inserted, the glaucoma stent 520 extends from the anterior chamber 504 to the subconjunctival space 515.

The cross-linked subconjunctival space or bleb may be created immediately before the implantation of the stent 520 during a single surgical procedure so as to prepare the space first so that the end of the stent 520 enters the cross-linked subconjunctival space during the surgery. Alternatively, the cross-linked subconjunctival space or bleb may be created during a first surgical procedure, and then the stent 520 may be implanted thereafter during a second, separate surgical procedure. In this alternative embodiment, the second surgical procedure may be performed a significant time after the first surgical procedure. The cross-linked subconjunctival space or bleb may be irradiated using either an external ultraviolet light or a handheld fiber optic connected to a laser that is placed close to the space or bleb and the tissue that will surround the stent 520 (i.e., the corneoscleral tissue). This tissue may be irradiated for 5 to 20 minutes so as to cross-link the tissue.

Figure 45:
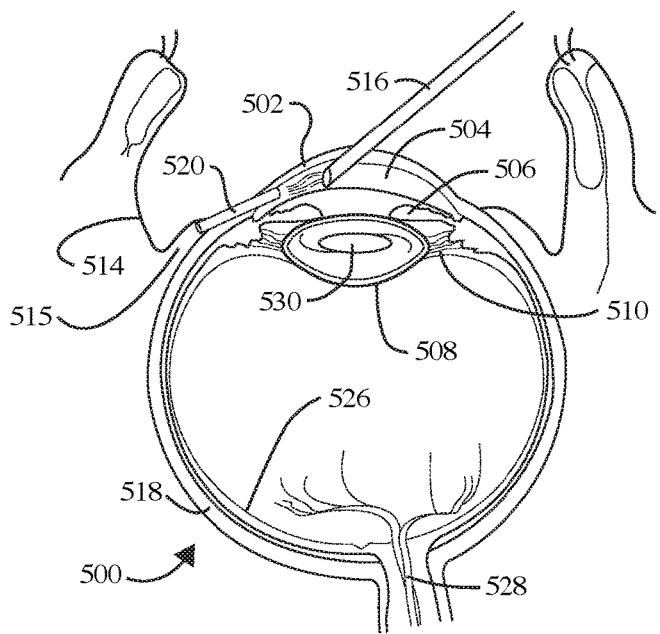
FIG. 45 is another side cross-sectional view of the eye of FIG. 44, which illustrates the application of a photosensitizer after the implantation of the glaucoma stent of FIG. 42 in the eye.
Figure 46:
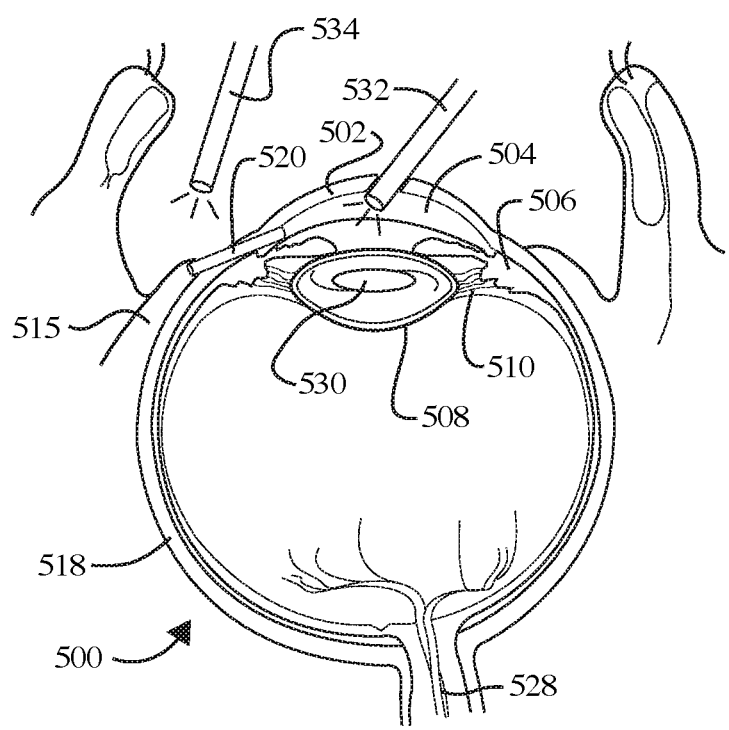
FIG. 46 is yet another side cross-sectional view of the eye of FIG. 44, which illustrates the irradiation of the glaucoma stent and the surrounding areas in the eye so as to activate cross-linkers and prevent fibrosis.
Figure 47:
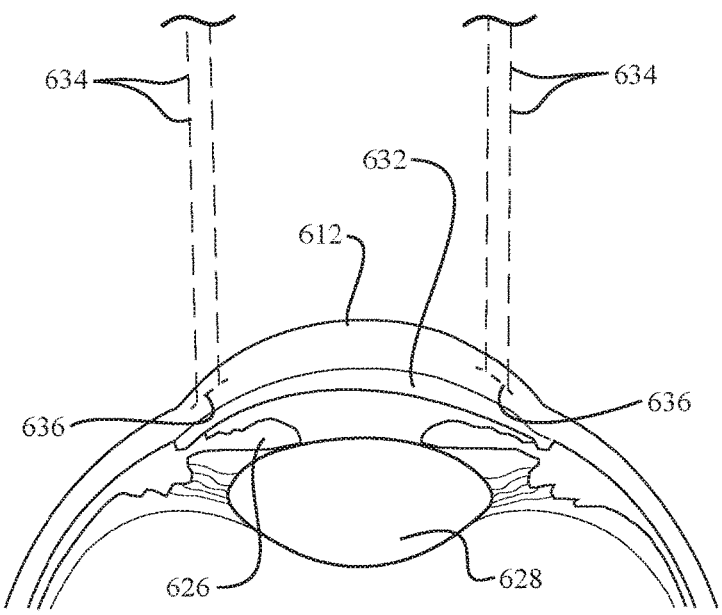
FIG. 47 is a partial side cross-sectional view illustrating the formation of an incision into a peripheral portion of a cornea of an eye so as to create a pocket for receiving a corneal intraocular pressure sensor, according to another embodiment of the invention.

Then, after the implantation of the stent 520 in the conjunctiva 514 of the eye, the photosensitizer (e.g., riboflavin in a biocompatible fluid) is injected into the eye 500 using a needle 516 (see FIG. 45). That is, similar to that described above, the photosensitizer or cross-linker is injected using the needle 516 into the anterior chamber 504 of the eye 500 after the implantation of the stent 520. The photosensitizer injected from the needle 516 travels through the glaucoma stent 520, and into the subconjunctival space 515 of the eye 500 so that the photosensitizer permeates the tissue surrounding the glaucoma stent 520. After which, at the end of the surgical procedure, the stent 520 and the areas surrounding the stent 520, both inside and outside, are cross-linked. In particular, with reference to FIG. 46, an inflow end of the glaucoma stent 520 proximate to the anterior chamber 504 of the eye 500 is irradiated using a fiber optic 532 carrying ultraviolet (UV) laser light so as to cross-link the tissue surrounding the glaucoma stent 520, thereby preventing fibrosis around the glaucoma stent 520. Also, as shown in FIG. 46, an outflow end of the glaucoma stent 520 in the subconjunctival space 515 of the eye 500 is irradiated using a fiber optic 534 carrying ultraviolet (UV) laser light so as to cross-link the tissue surrounding the glaucoma stent 520, thereby preventing fibrosis around the glaucoma stent 520 outflow.

Next, an illustrative embodiment of a method of implanting a corneal intraocular pressure sensor in an eye of a patient will be described below with reference to FIGS. 47-53. In general, the procedure involves the steps of forming a pocket in a cornea of an eye so as to gain access to tissue surrounding the pocket, applying a photosensitizer inside the pocket so that the photosensitizer permeates at least a portion of the tissue surrounding the pocket, irradiating the cornea so as to activate cross-linkers in the portion of the tissue surrounding the pocket, and inserting an intracorneal implant comprising a pressure sensor into the pocket after the tissue has been cross-linked. The pressure sensor of the intracorneal implant is configured to measure the intraocular pressure of the eye of the patient. As shown in FIGS. 47-53, the eye 610 undergoing the implantation of the pressure sensor generally includes a cornea 612, an iris 626, a lens 628, and an anterior chamber 632.

Initially, a pocket is formed in the cornea of the eye so as to gain access to tissue surrounding the pocket. In the illustrative embodiment, referring to FIG. 47, a two or three-dimensional portion of stromal tissue is first cut out from the cornea of the eye using a femtosecond laser (i.e., an incision 636 is first cut in the cornea 612 of the eye 610 using the laser beam(s) 634 emitted from the femtosecond laser). Then, the three-dimensional cut portion of the cornea 612 is removed using forceps so as to create a three-dimensional pocket for receiving the intracorneal implant. The formation of the three-dimensional pocket creates a cavity so that, when the intracorneal implant is placed in it, the implant will not exert any pressure on the stromal tissue of the cornea.

In one or more embodiments, an intrastromal corneal pocket is created in the peripheral part of the cornea involving 1 to 4 millimeter (mm) areas in width located between the cornea and the anterior sclera using a femtosecond laser. Prior to the laser application, if needed, the peripheral conjunctival capillaries are bleached out with a low dose of vasoconstrictive medication, such as 0.5% to 1% phenylephrine applied locally with a cotton swab applicator, and/or a low dose (0.1 to 2%) hyaluronic acid in a fluid is applied to make the corneal limbus area transparent.

In one or more embodiments, the three-dimensional pocket 624 formed in the peripheral portion of the cornea extends between 1 degree and 360 degrees around the corneal periphery (refer to the front view of FIG. 51), and the three-dimensional pocket is located at a predetermined distance from the Bowman's membrane in the corneal periphery of the eye.

In one or more embodiments, one or two incisions are used depending on the size of the pocket to access the intrastromal incision. Then, a curved probe is used to separate the remaining corneal adhesion between the walls of the incision, so as to create a pocket for the injection of a photosensitizer (i.e., a cross-linker).

Figure 48:
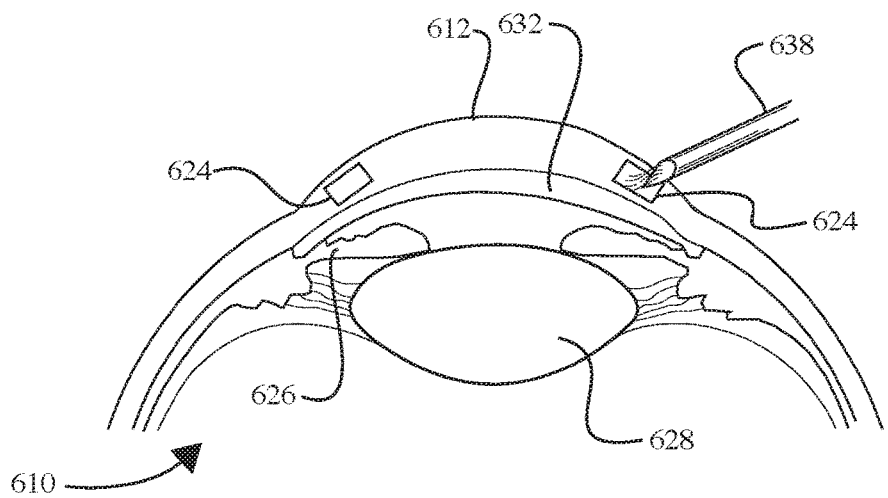
FIG. 48 is another partial side cross-sectional view of the eye of FIG. 47, which illustrates the injection of a photo-sensitizer into the pocket in the peripheral portion of the cornea of the eye.
Figure 49:
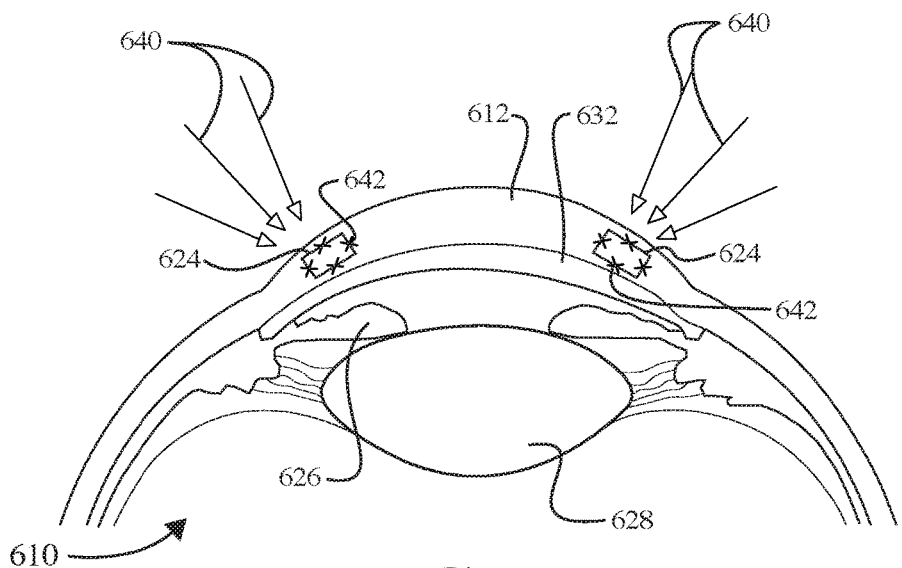
FIG. 49 is yet another partial side cross-sectional view of the eye of FIG. 47, which illustrates the irradiation of the stromal tissue surrounding the pocket in the peripheral portion of the cornea of the eye using ultraviolet radiation delivered from outside of the cornea.
Figure 50:
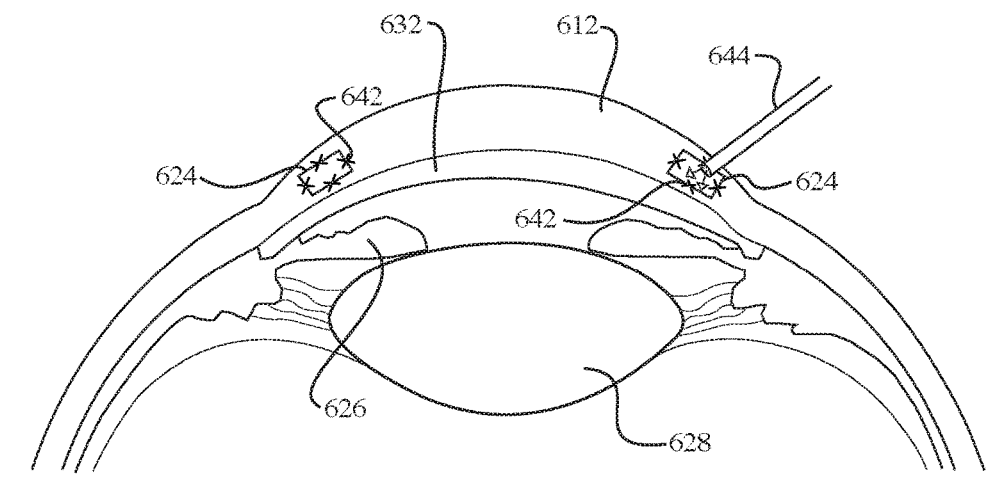
FIG. 50 is still another partial side cross-sectional view of the eye of FIG. 47, which illustrates the irradiation of the stromal tissue surrounding the pocket in the peripheral portion of the cornea of the eye using a fiber optic delivering ultraviolet radiation inside the pocket, according to an alternative embodiment of the invention.

After the three-dimensional pocket 624 is formed, a photosensitizer is applied inside the three-dimensional pocket 624 so that the photosensitizer permeates the tissue surrounding the pocket (refer to FIG. 48). The photosensitizer facilitates the cross-linking of the tissue surrounding the pocket 624. In the illustrative embodiment, a photosensitizer (i.e., a cross-linker), such as riboflavin, is injected with a needle 638 (see FIG. 48) at a concentration of about 0.5% to 4% in a biocompatible fluid, such as a physiological saline solution, etc., in a volume of 0.01 milliliters (ml) to 1 milliliters (ml) as needed for the extent of the pocket 624 to cover the internal walls of the corneal pocket 624 for a desired duration for the photo sensitizer to penetrate at least 20 microns beyond the corneal pocket 624 in the corneal stroma. This will take about a few seconds to about 30 seconds, while avoiding the crosslinking of the entire remaining wall of the cornea 612. In the illustrative embodiment, an effort is made to limit the corneal staining with the photosensitizer to the wall of the pocket 624 so that the photosensitizer never reaches the anterior or posterior full thickness of the cornea 612.

In one or more embodiments, 0.01 milliliters (ml) to 0.1 milliliters (ml) of 0.02 to 2% concentration lidocaine or bupivacaine solution may be injected alone or along with the photosensitizer in the corneal pocket 624 to anesthetize the cornea for a duration of 10 to 15 hours, thereby eliminating pain sensation or discomfort of the surgery.

In one or more embodiments, the width of the corneal pocket 624 may be 1 to 3 millimeters (mm), as needed. The pocket may be circular, semi-circular, C-shaped, doughnut-shaped, rectangular, or any other suitable shape.

Next, in the illustrative embodiment, shortly after the photosensitizer is applied inside the pocket 624, the cornea 612 of the eye 610 is irradiated from the outside using ultraviolet (UV) radiation 640 so as to activate cross-linkers in the portion of the tissue surrounding the three-dimensional pocket 624, and thereby stiffen a wall of the pocket and kill cells in the portion of the tissue surrounding the pocket.

In the illustrative embodiment, ultraviolet (UV) radiation 640 at a desired power of 0.5 to 50 mW/cm2 and a duration 1 to 15 minutes is applied to the cornea 612 of the eye 610 from outside in a stationary manner (see FIG. 49), or using a continuous painting or oscillatory technique with a focused small-sized spots of 1 to 4 millimeters (mm) and high energy to cover the width of the pocket, and to activate the photosensitizer in the corneal pocket 624, and thereby cross link the collagen of the corneal stroma 642 surrounding the corneal pocket 624, kill all cells located within the cross-linked corneal area while providing a physical stability to the wall of the corneal pocket and preventing the wall from adhering to itself or to a future implant. In other embodiments, if a photosensitizer other than riboflavin is used, radiation with another wavelength of light may be applied to the cornea 612 of the eye 610 to cross-link the collagen of the corneal stroma 642 surrounding the corneal pocket 642.

In one or more embodiments, ultraviolet (UV) radiation at the desired power in a form of stationary or focused light for a duration of 1 to 5 minutes is applied, as needed, depending on the size of the pocket 624, and when using the painting method, the ultraviolet radiation is applied for 1 to 20 minutes depending on the size of the pocket 624. The power used for the UV radiation and the focal spot size of the laser that is used depends on the power of the radiation and the length of the pocket 624. The radiation may be applied externally, or via a fiber optic 644 inserted inside the pocket 624 in a painting fashion (see FIG. 50), so as to activate the photosensitizer and cross-link the collagen of the corneal stroma 642 surrounding the corneal pocket 624, thereby killing all cells located within the cross-linked cornea 642 while preventing encapsulation, cell migration, or rejection of the implant, and also providing an amorphous wall between the implant and the rest of the corneal stroma creating a vascular free zone only to the extent that the cross-linker has penetrated in the cornea surrounding the implant. The radiation is applied a short time after the cross-linker is injected in the pocket 624.

In one or alternative embodiments, the cornea is cross-linked from outside by dropping a cross-linker, such as riboflavin, at concentration of 1-2% in a physiological solution having dextran or hyaluronic acid or chondroitin sulfate over the corneal epithelium or denuded corneal epithelium for a period of time of 15 to 30 minutes. After which, the cornea 612 is cross-linked with the UV laser light for 10 to 50 minutes depending on the power of the UV laser applied, then waiting after cross-linking for a period of 3-4 weeks to implant the intraocular pressure sensor in the cross-linked cornea as described above.

Figure 51:
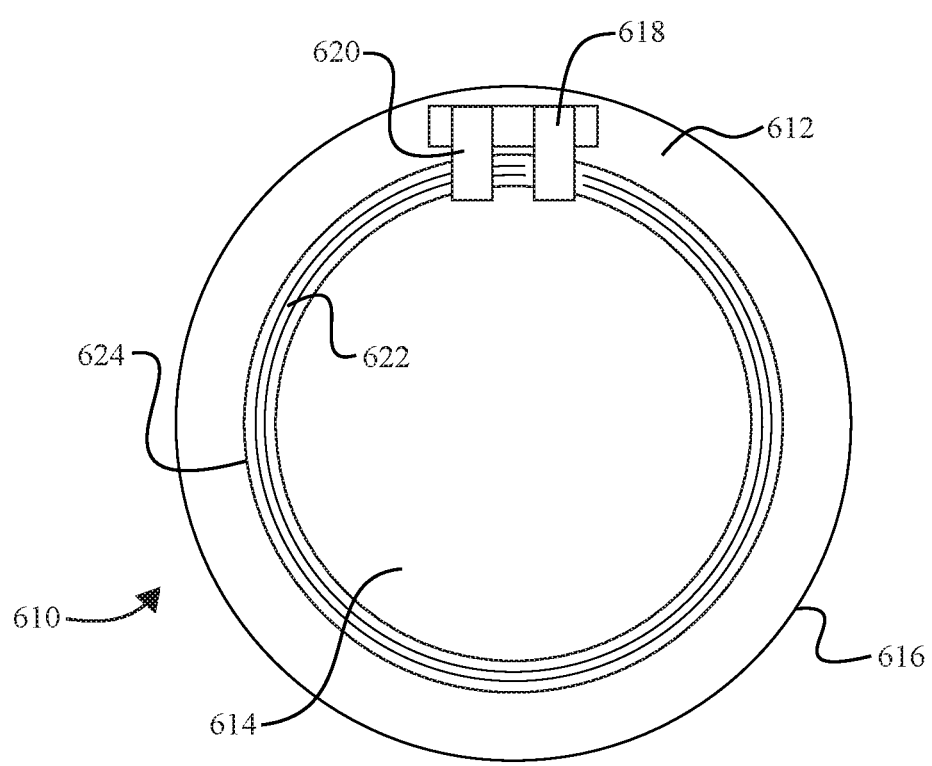
FIG. 51 is a front view of the eye of FIG. 47, which illustrates the components of a corneal intraocular pressure sensor disposed in the pocket in the peripheral portion of the cornea of the eye.
Figure 52:
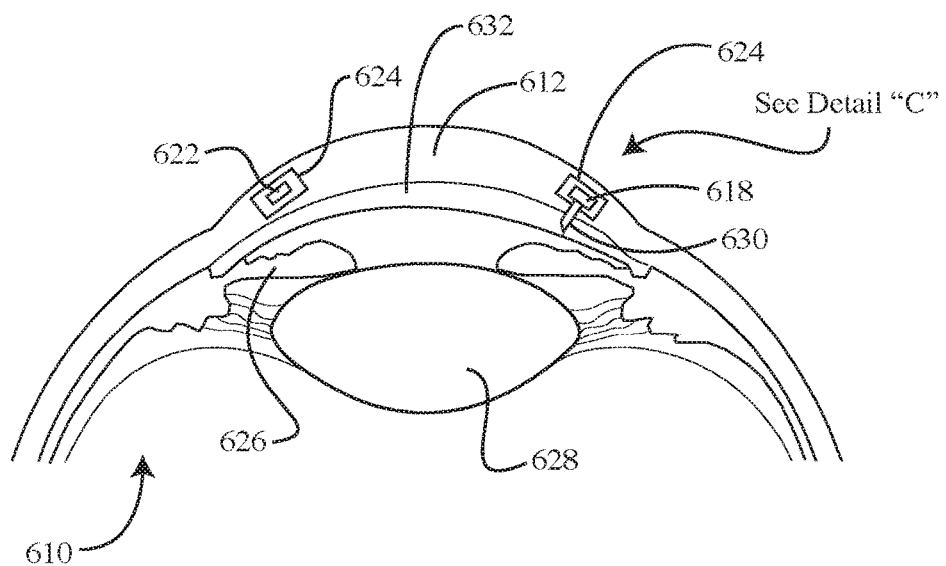
FIG. 52 is still another partial side cross-sectional view of the eye of FIG. 47, which illustrates the peripheral cross-linked corneal pocket with the components of the corneal intraocular pressure sensor disposed therein.
Figure 53:
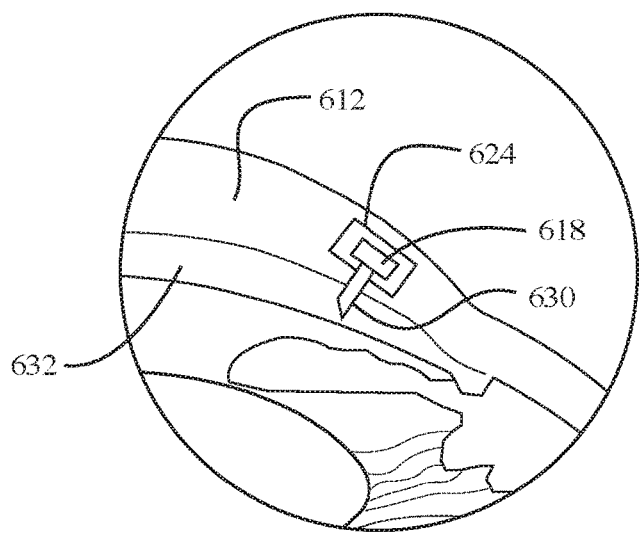
FIG. 53 is a partial, enlarged side cross-sectional view of the eye of FIG. 52 (Detail "C"), which illustrates the needle of the corneal intraocular pressure sensor extending into the anterior chamber of the eye.

Now, with reference to FIGS. 51-53, it can be seen that, after the portion of the tissue surrounding the pocket 624 has been stiffened and is devoid of cellular elements by the activation of the cross-linkers, an intracorneal implant comprising a pressure sensor 618 is inserted into the three-dimensional pocket 624 formed in the cornea 612 of the eye 610, which is in a location anteriorly disposed relative to the iris 626 and the lens 628. As shown in these figures, in the illustrative embodiment, the intracorneal implant is equipped with a pressure sensor 618, such as a capacitor, located in the corneal periphery of the eye 610. Also, as best shown in the sectional view of FIG. 53, the pressure sensor 618 of the intracorneal implant is equipped with a needle 630 that penetrates the rest of the cornea 612 and opens in the anterior chamber 632 of the eye 610 to measure the intraocular pressure directly by a portion of the sensor 618 being disposed inside the needle 630 without obstructing the central vision through the central cornea 614 (e.g., refer to FIG. 51). Turning to FIGS. 51 and 52, it can be seen that the sensor 618 is equipped with an antenna 622 that can transmit the information about the intraocular pressure for a duration of 24 hours and beyond while a receiver located outside of the eye 610 (e.g, a receiver on a regular eyeglass frame) receives the information and records and/or transmits the information to another remote device. The information is transmitted to a processor that transmits the information on the intraocular pressure uninterruptedly for years after implantation over a substantial distance to a doctor's computer or the patient's computer. The capabilities of the present invention are in stark contrast to the aforedescribed conventional contact lenses that can be carried only for 24 hours on the cornea to measure the intraocular pressure (IOP). If the conventional contact lenses are left on the cornea for a long time (i.e., greater than 24 hours), they can affect the integrity of the cornea, interfere with the oxygen and nutrition of the cornea, and ultimately lead to corneal abrasion or an infection.

In one or more embodiments, two-dimensional or three-dimensional stromal tissue is cut and/or removed with a femtosecond laser depending on the thickness of the sensor 618 and the antenna 622 and the location where the implant will be placed. As such, a pocket space 624 is created for the intracorneal implant to stay in place without exerting pressure on the remaining cornea 612 (see FIG. 52). As described above, after the pocket 624 is formed, it is followed by the cross-linking of the wall of the pocket so that the corneal pocket is cross-linked.

In one or more embodiments, the surface of the intraocular implant is coated with albumin or collagen, or another organic polymer, etc. that can absorb the photosensitizer after the implant is dipped in the photosensitizer and implanted in the corneal pocket. The photosensitizer leaks out of the polymeric coating of the implant into the corneal stroma, and then ultraviolet (UV) radiation at the desired power and duration is applied externally to activate the photosensitizer in the corneal pocket 624 and the implant coating to cross-link the collagen surrounding the implant, while killing all cells located within the cross-linked cornea, providing physical stability to the cornea, preventing the adhesion or gluing of the implant to the surrounding tissue, and preventing fibrous ingrowth or encapsulation, which can lead to an implant rejection. Also, advantageously, the cross-linking of the corneal pocket 624 makes it possible to exchange the implant when needed without the occurrence of much trauma to the cornea 612, because the prior cross-linking eliminates the cells that cause adhesion between the cornea 612 and the implant.

In one or more embodiments, if needed in the postoperative period, the cross-linking of the wall of the intraocular implant can be repeated by injection of riboflavin with a 33 gauge needle in the space between the implant and the wall of the cavity in which the implant resides, and then the cornea 612 with the implant may be subsequently cross-linked with ultraviolet (UV) radiation to prevent encapsulation of the implant that makes the inspection of the implant in the post-operative period difficult.

In one or more embodiments, the intraocular implant has a small diameter needle 630 (see FIG. 53) of 23 to 34 gauge with a capacitor sensor or a nanocomposite pressure sensor disposed in the inside thereof, positioned at a 90 degree angle relative to the body of the implant, and exposed to the aqueous fluid so as to measure the intraocular pressure (IOP) of the eye 610.

The pressure sensor 618 of the intraocular implant is operatively connected to the processor of the implant, and to the antenna 622 and radio frequency (RF) generator 620 of the implant (see FIG. 51). The electrical energy for the radio frequency (RF) generator is provided by a small battery that can be charged from outside as it is done with inductive coupling using an electromagnetic field that transfers energy from a transmitter to a receiver, as known in the art. The needle 630 with the capacitor sensor inside it, penetrates the remaining corneal stroma located in the corneal periphery with minimal pressure, and is open to the inside of the anterior chamber 632 (see FIG. 53). In one or more embodiments, the needle 630 is less than 500 microns in length and less than 200 microns in diameter, and remains permanently in the anterior chamber 632 of the eye 610, without exciting a tissue response due to its cross-linked surface and its size, but can also be removed or replaced with ease. The intraocular pressure (IOP) values measured by the capacitor sensor are transmitted to a processor (e.g., a microprocessor), which is operatively coupled with the radio frequency (RF) generator 620, which transmits the information to remote devices by the means of the antenna 622. Because the wall of the corneal pocket 624 is cross-linked, it will not produce a scar around the implant and its sensor 618, radio frequency (RF) generator 620, and antenna 622, thus permitting direct visual inspection of the implant, which is capable of being removed and/or replaced if needed.

In one or more embodiments, the intraocular implant may be assembled during the surgery after the cross-linked pocket 624 is created. Initially, the antenna 622 is placed in the cross-linked pocket 624 that is disposed radially inward from the limbus 616 of the eye 610 (see FIG. 51), and then the sensor 618 and the radio frequency (RF) generator 620 are placed in the corneal pocket 624 and connected to the antenna 622 as a part of a minimally invasive surgery in the corneal periphery. The capacitor sensor is located inside the needle 630, and the tip of the needle 630 is pushed gently in the anterior chamber 632 of the eye 610 so as to measure the intraocular pressure (IOP) directly, continuously, and precisely from the inside of the eye 610. The sensor 618 with small needle 630 and the radio frequency (RF) generator 620 are located in the corneal periphery avoiding interfering with the patient's vision. In contrast to the other aforementioned conventional technologies, this implant does not need an intraocular surgery for its implantation and the natural crystalline lens 628 of the eye 610 does not need to be removed in order to obtain permanent intraocular pressure (IOP) information for the eye 610.

In one or more embodiments, prior to the insertion of the intracorneal implant into the pocket 624 of the eye 610, a predetermined amount of hyaluronic acid or a viscous biocompatible material is injected into the pocket 624 so as to simplify the insertion of the intracorneal implant in the cross-linked pocket 624.

In one or more embodiments, the pressure sensor and transmitter of the intraocular implant are located inside the peripheral cross-linked pocket 624 of the cornea 612 of the eye 610 that does not occupy the central corneal region 614 of the eye 610. Because the central corneal region 614 of the eye 610 remains open with the intracorneal implant, the intraocular pressure (IOP) may also be measured by a Goldmann applanation tonometer placed on the central part 614 of the cornea 612 that is exposed. Because the implant described herein is peripherally disposed, the central corneal region 614 of the eye 610 is not covered by a conventional contact lens pressure sensor, as described above. Therefore, the intraocular pressure (IOP) can be measured by an ophthalmologist in two ways using a Goldman applanation tonometer and by means of the pressure sensor of the intracorneal implant located in the anterior chamber 632 of the eye 610. Advantageously, the ability to take these dual intraocular pressure (IOP) measurements provides a means of comparison between the values obtained by the intraocular pressure sensor and the Goldmann applanation tonometer to correlate or properly adjust the values obtained from the corneal intraocular pressure (IOP) sensor so as to ensure that measurements by the corneal intraocular pressure (IOP) sensor represent the true intraocular pressure (IOP) of the eye 610, and so the corneal intraocular pressure (IOP) sensor is capable of being properly adjusted using the software of the processor of the corneal intraocular pressure (IOP) sensor. The information obtained with the corneal intraocular pressure (IOP) sensor is also capable of being transmitted remotely via the radio frequency (RF) generator 620, and recorded and forwarded to an ophthalmologist who, in turn, can control the intraocular pressure (IOP) by medication or surgery.

In one or more embodiments, the transmitter of the intracorneal implant may be implanted separately from the pressure sensor 618 during the surgery, but then reconnected during the implantation.

Advantageously, the surgical implantation method and the corneal intraocular pressure (IOP) sensor described herein is capable of measuring the intraocular pressure (IOP) all day and night for a long period of time (e.g., weeks, months, or years), and then recording the intraocular pressure data that is measured so that an ophthalmologist can control the intraocular pressure (IOP) of the patient's eye by medication or surgery.

Any of the procedures described herein can be used alone, or in conjunction with, simultaneously with, before or after any other procedure, method or device that would treat or monitor glaucoma, prevent capsular opacification and fibrosis after cataract extraction during cataract surgery and/or prevent fibrosis around a shunt or stent after glaucoma surgery. Additionally, any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method of implanting a corneal intraocular pressure sensor in an eye of a patient, said method comprising:
   forming a pocket in the cornea of the eye so as to gain access to tissue surrounding the pocket;
   after the pocket in the cornea has been formed, applying a photosensitizer so that the photosensitizer permeates at least a portion of the tissue surrounding the pocket, the photosensitizer facilitating cross-linking of the tissue surrounding the pocket;
   irradiating the cornea so as to activate cross-linkers in the portion of the tissue surrounding the pocket, and thereby stiffen a wall of the pocket and kill cells in the portion of the tissue surrounding the pocket; and before or after the portion of the tissue surrounding the pocket has been stiffened and is devoid of cellular elements by the activation of the cross-linkers, inserting an intracorneal implant comprising a pressure sensor into the pocket, the pressure sensor of the intracorneal implant configured to measure the intraocular pressure of the eye of the patient.

2. The method according to claim 1, wherein the step of forming a pocket in the cornea of the eye further comprises:
cutting out a three-dimensional portion of stromal tissue from the cornea of the eye using a femtosecond laser; and
removing the three-dimensional cut portion of the cornea using forceps so as to create a three-dimensional pocket for receiving the intracorneal implant so that the intracorneal implant does not exert any pressure on the stromal tissue of the cornea, the three-dimensional pocket being formed in a peripheral portion of the cornea between the cornea and the anterior sclera of the eye.

3. The method according to claim 2, further comprising the step of:
prior to forming the pocket in the cornea of the eye, bleaching out any peripheral conjunctival capillaries that are present with a low dose of a vasoconstrictive medication and/or a low dose of hyaluronic acid in a fluid in order to make the corneal limbus area transparent prior to applying the femtosecond laser.

4. The method according to claim 2, wherein the three-dimensional pocket formed in the peripheral portion of the cornea extends between 1 degree and 360 degrees around the corneal periphery, and the three-dimensional pocket is located at predetermined distance from the Bowman's membrane of the cornea of the eye, and the three-dimensional pocket has a width between approximately 1 millimeters and approximately 4 millimeters, inclusive.

5. The method according to claim 1, wherein the step of forming a pocket in the cornea of the eye further comprises:
forming one or two incisions in the stromal tissue of the cornea of the eye using a femtosecond laser; and
using a curved probe to separate a remaining corneal adhesion between walls of the incisions so as to create a three-dimensional pocket for the application of the photosensitizer.

6. The method according to claim 5, wherein the step of applying the photosensitizer comprises injecting the photosensitizer inside the three-dimensional pocket using a needle such that the photosensitizer penetrates at least 20 microns beyond a wall of the three-dimensional pocket in the stromal tissue of the cornea, the photosensitizer comprising riboflavin.

7. The method according to claim 6, further comprising the step of:
injecting 0.01 milliliters to 0.1 milliliters of a 0.02 to 2% lidocaine or bupivacaine solution alone or together with the photosensitizer so as to anesthetize the cornea for between 10 to 15 hours, thereby eliminating a pain sensation or discomfort during the surgical procedure.

8. The method according to claim 5, wherein the step of applying the photosensitizer comprises applying the photosensitizer in drop form to the epithelium or denuded epithelium of the cornea, the photosensitizer comprising riboflavin at a concentration of 1-2% in a physiological solution that additionally includes dextran, hyaluronic acid, or chondroitin sulfate;
wherein the step of irradiating the cornea so as to activate cross-linkers in the portion of the tissue surrounding the pocket comprises irradiating the cornea with ultraviolet light from outside the cornea; and
wherein the method further comprises the step of waiting for a period of 3 to 4 weeks prior to inserting the intracorneal implant comprising the pressure sensor into the pocket.

9. The method according to claim 1, wherein the step of creating a pocket in the cornea of the eye further comprises forming a circular-shaped pocket, a semi-circular-shaped pocket, a C-shaped pocket, a doughnut-shaped pocket, or a rectangular-shaped pocket in the cornea of the eye, and removing the tissue inside the circular-shaped pocket, the semi-circular-shaped pocket, the C-shaped pocket, the doughnut-shaped pocket, or the rectangular-shaped pocket.

10. The method according to claim 1, wherein the step of irradiating the cornea so as to activate cross-linkers in the portion of the tissue surrounding the pocket comprises irradiating the cornea with ultraviolet light, another wavelength of light, microwaves, or combinations thereof.

11. The method according to claim 1, wherein the step of irradiating the cornea so as to activate cross-linkers in the portion of the tissue surrounding the pocket comprises inserting a fiber optic into the pocket and irradiating the cornea with light emitted from the fiber optic so as to activate the cross-linkers in the portion of the tissue surrounding the pocket.

12. The method according to claim 1, wherein the step of irradiating the cornea so as to activate cross-linkers in the portion of the tissue surrounding the pocket comprises irradiating the cornea from outside the eye.

13. The method according to claim 1, further comprising the step of:
prior to the insertion of the intracorneal implant into the pocket, injecting a predetermined amount of hyaluronic acid or a viscous biocompatible material into the pocket so as to simplify the insertion of the intracorneal implant in the pocket.

14. The method according to claim 1, wherein the intracorneal implant further comprises a needle and the pressure sensor of the intracorneal implant comprises a capacitor; and
wherein the method further comprises the step of:
penetrating a posterior portion of the cornea using the needle, an open end of the needle opening into the anterior chamber of the eye so as to measure the intraocular pressure of the eye without obstructing vision through the central cornea of the eye.

15. The method according to claim 14, wherein the needle of the intracorneal implant is a 23-34 gauge needle with the pressure sensor disposed inside the needle; and wherein the needle is disposed generally perpendicularly with respect to a body portion of the intracorneal implant and the needle has a length that is less than 500 microns and a diameter that is less than 200 microns.

16. The method according to claim 1, wherein the intracorneal implant further comprises an antenna; and wherein the method further comprises the step of:
transmitting intraocular pressure data acquired by the pressure sensor wirelessly to a remote receiver located outside of the eye.

17. The method according to claim 16, wherein the remote receiver is located on an eyeglass frame of the patient; and wherein the method further comprises the step of:
continuously receiving the intraocular pressure data transmitted by the antenna of the intracorneal implant at the remote receiver during a period of time selected from the group consisting of weeks, months, and years.

18. The method according to claim 16, further comprising the step of:
- after receiving the intraocular pressure data at the remote receiver, further transmitting the intraocular pressure data to a remote computing device for processing and analyzing the intraocular pressure data.

19. The method according to claim 1, further comprising, prior to inserting the intracorneal implant with the pressure sensor into the pocket, the steps of:
- coating an outer surface of the intracorneal implant with an organic polymer configured to absorb the photosensitizer;
- immersing the intracorneal implant in a biocompatible solution comprising the photosensitizer so that the photosensitizer is able to diffuse out of the organic polymer coating of the intracorneal implant after the intracorneal implant is inserted into the pocket; and
- after the intracorneal implant is inserted into the pocket, irradiating the cornea so as to activate cross-linkers in the portion of the tissue surrounding the pocket, and thereby stiffen a wall of the pocket and kill cells in the portion of the tissue surrounding the pocket.

20. The method according to claim 1, further comprising the step of:
- after the implantation of the intracorneal implant, applying the photosensitizer one or more additional times inside the space between the intracorneal implant and the surrounding corneal tissue by injecting the photosensitizer inside the space between the intracorneal implant and the surrounding corneal tissue using a 33 gauge needle, and irradiating the cornea one or more additional times with ultraviolet radiation to cross-link the tissue surrounding the intracorneal implant so as to prevent encapsulation of the intracorneal implant and cellular migration towards the intracorneal implant.

21. The method according to claim 20, wherein the intracorneal implant further comprises an antenna, a radio frequency generator, and a needle containing the pressure sensor;
- and wherein the step of inserting the intracorneal implant into the pocket further comprises:
- placing the antenna of the intracorneal implant into the cross-linked pocket;
- placing the radio frequency generator and the pressure sensor into the cross-linked pocket;
- connecting the radio frequency generator and the pressure sensor to the antenna; and
- pushing the needle with the pressure sensor into the anterior chamber of the eye so that the pressure sensor is capable of measuring the intraocular pressure directly in a continuous manner.

22. The method according to claim 1, further comprising the steps of:
- taking a first measurement of the intraocular pressure of the eye of the patient using the pressure sensor of the intracorneal implant disposed in the cross-linked pocket at a periphery of the cornea;
- taking a second measurement of the intraocular pressure of the eye using a Goldmann applanation tonometer placed on a central portion of the outer cornea surface; and
- comparing the first measurement of the intraocular pressure determined using the pressure sensor of the intracorneal implant to the second measurement of the intraocular pressure determined using the Goldmann applanation tonometer in order to validate the accuracy of the pressure sensor of the intracorneal implant.

* * * * *